(12) United States Patent
Pedersen et al.

(10) Patent No.: US 12,396,953 B2
(45) Date of Patent: *Aug. 26, 2025

(54) SOLID COMPOSITIONS COMPRISING A GLP-1 AGONIST AND A SALT OF N-(8-(2-HYDROXYBENZOYL)AMINO)CAPRYLIC ACID

(71) Applicant: Novo Nordisk A/S, Bagsvaerd (DK)

(72) Inventors: Betty Lomstein Pedersen, Glostrup (DK); Birgitte Nissen, Ballerup (DK)

(73) Assignee: Novo Nordisk A/S, Bagsvaerd (DK)

( * ) Notice: Subject to any disclaimer, the term of this patent is extended or adjusted under 35 U.S.C. 154(b) by 0 days.

This patent is subject to a terminal disclaimer.

(21) Appl. No.: 18/386,839

(22) Filed: Nov. 3, 2023

(65) Prior Publication Data
US 2024/0099981 A1    Mar. 28, 2024

Related U.S. Application Data

(63) Continuation of application No. 16/570,723, filed on Sep. 13, 2019, now Pat. No. 11,833,248, which is a continuation of application No. PCT/EP2019/052487, filed on Feb. 1, 2019.

(30) Foreign Application Priority Data

Feb. 2, 2018 (EP) .................... 18154913

(51) Int. Cl.
| | |
|---|---|
| *A61K 9/20* | (2006.01) |
| *A61K 38/26* | (2006.01) |
| *A61P 3/04* | (2006.01) |
| *A61P 3/10* | (2006.01) |
| *C07K 14/605* | (2006.01) |

(52) U.S. Cl.
CPC ............ *A61K 9/2013* (2013.01); *A61K 38/26* (2013.01); *A61P 3/04* (2018.01); *A61P 3/10* (2018.01); *C07K 14/605* (2013.01)

(58) Field of Classification Search
None
See application file for complete search history.

(56) References Cited

U.S. PATENT DOCUMENTS

| | | |
|---|---|---|
| 5,545,618 A | 8/1996 | Buckley et al. |
| 5,574,010 A | 11/1996 | McFadden |
| 5,604,203 A | 2/1997 | Balasubramaniam |
| 5,650,386 A | 7/1997 | Leone-Bay et al. |
| 5,773,647 A | 6/1998 | Leone-Bay et al. |
| 5,866,536 A | 2/1999 | Leone-Bay et al. |
| 5,968,899 A | 10/1999 | Sekine et al. |
| 6,046,167 A | 4/2000 | Balasubramaniam |
| 6,071,510 A | 6/2000 | Leone-Bay et al. |
| 6,268,343 B1 | 7/2001 | Knudsen et al. |
| 6,458,924 B2 | 10/2002 | Knudsen et al. |
| 7,049,283 B2 | 5/2006 | Ault et al. |
| 7,235,627 B2 | 6/2007 | Knudson et al. |
| 7,271,149 B2 | 9/2007 | Glaesner et al. |
| 7,417,028 B2 | 8/2008 | Ewing et al. |
| 7,829,123 B2 | 11/2010 | Sundholm et al. |
| 8,022,035 B2 | 9/2011 | Schwartz et al. |
| 8,039,018 B2 | 10/2011 | Majuru et al. |
| 8,053,429 B2 | 11/2011 | Cumming et al. |
| 8,097,698 B2 | 1/2012 | Knudsen et al. |
| 8,536,122 B2 | 9/2013 | Lau et al. |
| 8,648,041 B2 | 2/2014 | Garibay et al. |
| 8,895,694 B2 | 11/2014 | Spetzler et al. |
| 8,901,073 B2 | 12/2014 | Bloom |
| 9,067,977 B2 | 6/2015 | Spetzler et al. |
| 9,085,637 B2 | 7/2015 | Oestergaard et al. |
| 9,186,392 B2 | 11/2015 | Klein et al. |
| 9,266,940 B2 | 2/2016 | Wieczorek et al. |
| 9,278,123 B2 | 3/2016 | Sauerberg et al. |
| 9,527,900 B2 | 12/2016 | Linderoth et al. |
| 9,993,430 B2 | 6/2018 | Jensen et al. |
| 10,005,827 B2 | 6/2018 | Spetzler et al. |
| 10,086,047 B2 | 10/2018 | Sauerberg et al. |
| 10,246,497 B2 | 4/2019 | Oestergaard et al. |
| 10,278,923 B2 | 5/2019 | Nielsen et al. |
| 10,335,369 B2 | 7/2019 | Vilhelmsen |
| 10,689,429 B2 | 6/2020 | Linderoth et al. |
| 10,888,605 B2 | 1/2021 | Moeller et al. |
| 10,933,120 B2 | 3/2021 | Vilhelmsen et al. |
| 10,960,052 B2 | 3/2021 | Sauerberg et al. |
| 11,033,499 B2 | 6/2021 | Jensen et al. |

(Continued)

FOREIGN PATENT DOCUMENTS

| | | |
|---|---|---|
| AR | 112015 A1 | 9/2019 |
| AR | 112480 A1 | 10/2019 |

(Continued)

OTHER PUBLICATIONS

Kusher IV et al., "Scale-up model describing the impact of lubrication on tablet tensile strength," International Journal of Pharmaceutics, 2010, vol. 399, Nos. 1-2, pp. 19-30.
Lieberman et al., Pharmaceutical Dosage Forms: Tablets, 2nd Edition, 1989, Chapter 5, pp. 247-284.
Parikh, Handbook of Pharmaceutical Granulation Technology, 3rd Edition, 2010, Informa Healthcare, pp. 2-3.
Remington, The Science and Practice of Pharmacy, 21st Edition, 2005, Lippincott, Williams & Wilkins, pp. 677, 892-893, 896, and 1040.
Sakr et al., "Oral Solid Dosage Forms," Remington, Essentials of Pharmaceutics, 1st Edition, Chapter 30, 2012, pp. 581-610.
Valtrex 500mg Tablets—Summary of Product Characteristics (SmPC), Sep. 26, 2019, pp. 1-10.

(Continued)

*Primary Examiner* — Thea D' Ambrosio
(74) *Attorney, Agent, or Firm* — Leon Y. Lum

(57) ABSTRACT

The invention relates to pharmaceutical compositions comprising a peptide, such as a GLP-1 peptide and a salt of N-(8-(2-hydroxybenzoyl)amino)caprylic acid. The invention further relates to processes for the preparation of such compositions, and their use in medicine.

56 Claims, 2 Drawing Sheets
Specification includes a Sequence Listing.

(56) References Cited

U.S. PATENT DOCUMENTS

| | | |
|---|---|---|
| 11,034,746 B2 | 6/2021 | Wieczorek et al. |
| 11,117,947 B2 | 9/2021 | Wieczorek et al. |
| 11,167,014 B2 | 11/2021 | Vegge et al. |
| 11,833,248 B2 * | 12/2023 | Pedersen .............. A61K 9/2013 |
| 2001/0011071 A1 | 8/2001 | Knudsen et al. |
| 2002/0141985 A1 | 10/2002 | Pittner et al. |
| 2004/0053819 A1 | 3/2004 | Dodd et al. |
| 2005/0009748 A1 | 1/2005 | Dinh et al. |
| 2005/0148497 A1 | 7/2005 | Khan |
| 2005/0176630 A1 | 8/2005 | Cowley et al. |
| 2006/0078622 A1 | 4/2006 | Majuru et al. |
| 2006/0078623 A1 | 4/2006 | Dhoot et al. |
| 2006/0135747 A1 | 6/2006 | Levy et al. |
| 2006/0211610 A1 | 9/2006 | Dong |
| 2006/0286129 A1 | 12/2006 | Sarubbi |
| 2007/0049557 A1 | 3/2007 | Ahmed et al. |
| 2007/0135351 A1 | 6/2007 | Conde-Knape et al. |
| 2007/0197445 A1 | 8/2007 | Balasubramaniam |
| 2007/0203058 A1 | 8/2007 | Lau et al. |
| 2007/0224262 A1 | 9/2007 | Majuru et al. |
| 2008/0076705 A1 | 3/2008 | Kodra et al. |
| 2008/0153779 A1 | 6/2008 | Liao et al. |
| 2008/0194486 A1 | 8/2008 | Bridon et al. |
| 2008/0194676 A1 | 8/2008 | Abbas et al. |
| 2008/0207507 A1 | 8/2008 | Lau et al. |
| 2008/0221038 A1 | 9/2008 | Balasubramaniam |
| 2008/0255250 A1 | 10/2008 | Gomez-Orellana et al. |
| 2008/0269114 A1 | 10/2008 | Schwartz |
| 2009/0088369 A1 | 4/2009 | Steiness |
| 2009/0099074 A1 | 4/2009 | Bridon et al. |
| 2009/0111730 A1 | 4/2009 | Dorwald et al. |
| 2009/0124639 A1 | 5/2009 | Oyewumi et al. |
| 2009/0143330 A1 | 6/2009 | Levchik et al. |
| 2009/0156478 A1 | 6/2009 | Lau et al. |
| 2009/0186811 A1 | 7/2009 | Schwartz |
| 2009/0215682 A1 | 8/2009 | Moore et al. |
| 2010/0016229 A1 | 1/2010 | Sarubbi |
| 2010/0069307 A1 | 3/2010 | Danho et al. |
| 2010/0069410 A1 | 3/2010 | Majuru et al. |
| 2010/0151009 A1 | 6/2010 | Levchik |
| 2010/0210470 A1 | 8/2010 | Citerone et al. |
| 2010/0210526 A1 | 8/2010 | Joshi |
| 2010/0239658 A1 | 9/2010 | Majuru et al. |
| 2010/0292133 A1 | 11/2010 | Spetzler et al. |
| 2010/0317057 A1 | 12/2010 | Lau et al. |
| 2010/0331245 A1 | 12/2010 | Dong |
| 2011/0142800 A1 | 6/2011 | Kidron et al. |
| 2011/0166321 A1 | 7/2011 | Garibay et al. |
| 2011/0218148 A1 | 9/2011 | Azria et al. |
| 2011/0275559 A1 | 11/2011 | Ostergaard et al. |
| 2012/0040893 A1 | 2/2012 | Cowley et al. |
| 2013/0040877 A1 | 2/2013 | Kofoed et al. |
| 2013/0053311 A1 | 2/2013 | Kalthoff et al. |
| 2013/0096055 A1 | 4/2013 | Kofoed et al. |
| 2013/0240587 A1 | 9/2013 | Buchhalter |
| 2013/0345134 A1 | 12/2013 | Sauerberg et al. |
| 2014/0011732 A1 | 1/2014 | Spetzler et al. |
| 2014/0296131 A1 | 10/2014 | Spetzler et al. |
| 2015/0025003 A1 | 1/2015 | Spetzler et al. |
| 2015/0031606 A1 | 1/2015 | Vilhelmsen |
| 2015/0072926 A1 | 3/2015 | Vilhelmsen et al. |
| 2015/0141336 A1 | 5/2015 | Joergensen et al. |
| 2015/0150811 A1 | 6/2015 | Jensen et al. |
| 2016/0067184 A1 | 3/2016 | Nielsen et al. |
| 2016/0151462 A1 | 6/2016 | Sauerberg et al. |
| 2016/0263197 A1 | 9/2016 | Oestergaard et al. |
| 2016/0289283 A1 | 10/2016 | Oestergaard et al. |
| 2017/0312225 A1 | 11/2017 | Nielsen et al. |
| 2017/0313750 A1 | 11/2017 | Oestergaard et al. |
| 2018/0021272 A1 | 1/2018 | Burshtein et al. |
| 2018/0028622 A1 | 2/2018 | Burshtein et al. |
| 2018/0036234 A1 | 2/2018 | Burshtein et al. |
| 2018/0036382 A1 | 2/2018 | Burshtein et al. |
| 2018/0050096 A1 | 2/2018 | Burshtein et al. |
| 2018/0235888 A1 | 8/2018 | Jensen et al. |
| 2018/0251512 A1 | 9/2018 | Wieczorek et al. |
| 2018/0263915 A1 | 9/2018 | Nybo et al. |
| 2018/0360918 A1 | 12/2018 | Sauerberg et al. |
| 2019/0216739 A1 | 7/2019 | Nielsen et al. |
| 2019/0231876 A1 | 8/2019 | Pedersen et al. |
| 2019/0314283 A1 | 10/2019 | Vilhelmsen |
| 2020/0000728 A1 | 1/2020 | Pedersen et al. |
| 2020/0079834 A1 | 3/2020 | Wieczorek et al. |
| 2020/0147179 A1 | 5/2020 | Vegge et al. |
| 2021/0162012 A1 | 6/2021 | Vilhelmsen et al. |
| 2021/0177944 A1 | 6/2021 | Sauerberg et al. |
| 2021/0275458 A1 | 9/2021 | Bjerregaard et al. |
| 2022/0265777 A1 | 8/2022 | Pedersen et al. |

FOREIGN PATENT DOCUMENTS

| | | | |
|---|---|---|---|
| CN | 1190893 | A | 8/1998 |
| CN | 1487825 | A | 4/2004 |
| CN | 1867360 | A | 11/2006 |
| CN | 101005857 | A | 7/2007 |
| CN | 101010339 | A | 8/2007 |
| CN | 101133082 | A | 2/2008 |
| CN | 101268099 | A | 9/2008 |
| CN | 101463081 | A | 6/2009 |
| CN | 102946875 | A | 2/2013 |
| CN | 106132985 | A | 11/2016 |
| CN | 107205949 | A | 9/2017 |
| EP | 0708179 | A2 | 4/1996 |
| EP | 0908515 | A2 | 4/1999 |
| EP | 1364967 | A2 | 11/2003 |
| EP | 2565202 | A1 | 3/2013 |
| EP | 2651398 | A1 | 10/2013 |
| EP | 3028709 | A1 | 6/2016 |
| EP | 3746111 | A1 | 12/2020 |
| JP | 05-506427 | | 9/1993 |
| JP | H05-506427 | A | 9/1993 |
| JP | 2001-504105 | A | 3/2001 |
| JP | 2004131398 | A | 4/2004 |
| JP | 2004521093 | | 7/2004 |
| JP | 2006-520818 | A | 9/2006 |
| JP | 2007-536268 | A | 12/2007 |
| JP | 2008-509933 | A | 4/2008 |
| JP | 2009542711 | A | 12/2009 |
| JP | 2010-530962 | A | 9/2010 |
| JP | 4585037 | B2 | 11/2010 |
| JP | 2011509077 | A | 3/2011 |
| JP | 2012-121923 | A | 6/2012 |
| JP | 2013543814 | A | 12/2013 |
| JP | 2014503526 | A | 2/2014 |
| JP | 2015-515459 | A | 5/2015 |
| KR | 20060100428 | A | 9/2006 |
| KR | 102072202 | | 1/2020 |
| NZ | 219575 | A | 4/1990 |
| RU | 2158138 | C2 | 10/2000 |
| RU | 2226402 | C2 | 4/2004 |
| RU | 2275207 | C2 | 4/2006 |
| WO | 9111457 | | 8/1991 |
| WO | 9614854 | A1 | 5/1996 |
| WO | 96/29342 | | 9/1996 |
| WO | 9725064 | | 7/1997 |
| WO | 9808871 | A1 | 3/1998 |
| WO | 9820885 | A1 | 5/1998 |
| WO | 9820895 | | 5/1998 |
| WO | 99/43705 | A1 | 9/1999 |
| WO | 99/43707 | A1 | 9/1999 |
| WO | 99/43708 | A1 | 9/1999 |
| WO | 99043706 | A1 | 9/1999 |
| WO | 9964060 | | 12/1999 |
| WO | 9964394 | A1 | 12/1999 |
| WO | 00/07617 | A1 | 2/2000 |
| WO | 00/16797 | A2 | 3/2000 |
| WO | 00/34331 | | 6/2000 |
| WO | 200048589 | A1 | 8/2000 |
| WO | 200050012 | A1 | 8/2000 |
| WO | 00/69911 | | 11/2000 |
| WO | 0066629 | A1 | 11/2000 |
| WO | 01/04156 | | 1/2001 |
| WO | 0124777 | A1 | 4/2001 |
| WO | 200141737 | A2 | 6/2001 |

(56) References Cited

FOREIGN PATENT DOCUMENTS

| | | |
|---|---|---|
| WO | 02/46227 A2 | 6/2002 |
| WO | 0247712 | 6/2002 |
| WO | 0248192 A2 | 6/2002 |
| WO | 03/002158 A1 | 1/2003 |
| WO | 2003005944 A1 | 1/2003 |
| WO | 03/011892 A2 | 2/2003 |
| WO | 03063838 A1 | 8/2003 |
| WO | 03/072195 A2 | 9/2003 |
| WO | 2004/067548 A2 | 8/2004 |
| WO | 04066966 A2 | 8/2004 |
| WO | 2004093823 | 11/2004 |
| WO | 2004/104018 A2 | 12/2004 |
| WO | 2005/005667 A2 | 1/2005 |
| WO | 2005004900 A1 | 1/2005 |
| WO | 2005/014035 A2 | 2/2005 |
| WO | 2005014049 A2 | 2/2005 |
| WO | 2005/027978 A2 | 3/2005 |
| WO | 2005/028516 A2 | 3/2005 |
| WO | 2005027978 | 3/2005 |
| WO | 2005/058954 A1 | 6/2005 |
| WO | 2005/058958 A2 | 6/2005 |
| WO | 2005049061 A2 | 6/2005 |
| WO | 2005/077072 A2 | 8/2005 |
| WO | 2005/077094 A2 | 8/2005 |
| WO | 2005/089786 A2 | 9/2005 |
| WO | 2005/089789 A2 | 9/2005 |
| WO | 2005/089790 A2 | 9/2005 |
| WO | 2005099672 A1 | 10/2005 |
| WO | 2005107462 A2 | 11/2005 |
| WO | 2005107773 A2 | 11/2005 |
| WO | 2005/117984 A2 | 12/2005 |
| WO | 2005/121090 A1 | 12/2005 |
| WO | 2006/005667 A2 | 1/2006 |
| WO | 2006005667 | 1/2006 |
| WO | 2006/017251 A2 | 2/2006 |
| WO | 06020207 A2 | 2/2006 |
| WO | 2006/037810 | 4/2006 |
| WO | 06/049681 A2 | 5/2006 |
| WO | 2006/077035 A1 | 7/2006 |
| WO | 2006/082204 A1 | 8/2006 |
| WO | 2006084164 A2 | 8/2006 |
| WO | 2006/097535 A2 | 9/2006 |
| WO | 2006/097536 A2 | 9/2006 |
| WO | 2006/097538 | 9/2006 |
| WO | 2006/097538 A1 | 9/2006 |
| WO | 2006096515 A2 | 9/2006 |
| WO | 2006097537 A2 | 9/2006 |
| WO | 2006103661 A2 | 10/2006 |
| WO | 2006/127948 A2 | 11/2006 |
| WO | 2006124047 | 11/2006 |
| WO | 2006124047 A2 | 11/2006 |
| WO | 2007/009894 A2 | 1/2007 |
| WO | 2007008778 A2 | 1/2007 |
| WO | 2007011958 A2 | 1/2007 |
| WO | 2007024700 A2 | 3/2007 |
| WO | 2007/038943 A1 | 4/2007 |
| WO | 2007038942 A1 | 4/2007 |
| WO | 2007061434 A2 | 5/2007 |
| WO | 2007/068718 A1 | 6/2007 |
| WO | 07065808 A2 | 6/2007 |
| WO | 2007067964 A2 | 6/2007 |
| WO | 2007093226 A1 | 8/2007 |
| WO | 07109354 A2 | 9/2007 |
| WO | 2007117706 A2 | 10/2007 |
| WO | 2007121318 A2 | 10/2007 |
| WO | 2007/128817 A2 | 11/2007 |
| WO | 2007146234 A2 | 12/2007 |
| WO | 2008/003947 A1 | 1/2008 |
| WO | 2008003050 | 1/2008 |
| WO | 2008003050 A2 | 1/2008 |
| WO | 2008020096 A1 | 2/2008 |
| WO | 2008028859 A1 | 3/2008 |
| WO | 2008033888 A2 | 3/2008 |
| WO | 2008039351 A2 | 4/2008 |
| WO | 08/053360 A2 | 5/2008 |
| WO | 2008/087186 A2 | 7/2008 |
| WO | 2008/087190 A2 | 7/2008 |
| WO | 2008109385 A2 | 9/2008 |
| WO | 2008132435 A1 | 11/2008 |
| WO | 2008/154619 A1 | 12/2008 |
| WO | 2009007714 A2 | 1/2009 |
| WO | 2009/030771 A1 | 3/2009 |
| WO | 2009030738 A1 | 3/2009 |
| WO | 2009032749 A2 | 3/2009 |
| WO | 2009033710 A1 | 3/2009 |
| WO | 2009/042922 A2 | 4/2009 |
| WO | 2009/050738 A2 | 4/2009 |
| WO | 09042922 A2 | 4/2009 |
| WO | 2009059188 A1 | 5/2009 |
| WO | 2009/083549 A1 | 7/2009 |
| WO | 2009/138511 A1 | 11/2009 |
| WO | 2010020978 A1 | 2/2010 |
| WO | 2010/029159 A1 | 3/2010 |
| WO | 10031707 A1 | 3/2010 |
| WO | 2010031521 A2 | 3/2010 |
| WO | 2010/043319 A1 | 4/2010 |
| WO | 2010052144 A2 | 5/2010 |
| WO | 2010/092163 A2 | 8/2010 |
| WO | 2010096175 A1 | 8/2010 |
| WO | 2011/029551 A2 | 3/2011 |
| WO | 11033068 A1 | 3/2011 |
| WO | 2011033068 A1 | 3/2011 |
| WO | 11045232 A2 | 4/2011 |
| WO | 2011058165 A1 | 5/2011 |
| WO | 2011080103 A1 | 7/2011 |
| WO | 2011084618 A2 | 7/2011 |
| WO | 2011094531 A1 | 8/2011 |
| WO | 2011109787 A1 | 9/2011 |
| WO | 2011116139 A2 | 9/2011 |
| WO | 2011131646 A1 | 10/2011 |
| WO | 2011138421 A1 | 11/2011 |
| WO | 2012080471 A1 | 6/2012 |
| WO | 2012140117 A1 | 10/2012 |
| WO | 2013009545 A1 | 1/2013 |
| WO | 2013139624 A1 | 9/2013 |
| WO | 2013139694 | 9/2013 |
| WO | 2013139694 A1 | 9/2013 |
| WO | 2013139695 A1 | 9/2013 |
| WO | 2013189988 A1 | 12/2013 |
| WO | 2014005858 A1 | 1/2014 |
| WO | 2014177683 A1 | 11/2014 |
| WO | 2014178018 A1 | 11/2014 |
| WO | 2015071355 A1 | 5/2015 |
| WO | 2016111971 | 7/2016 |
| WO | 2016128970 A1 | 8/2016 |
| WO | 2016128971 A1 | 8/2016 |
| WO | 2016128972 A1 | 8/2016 |
| WO | 2016128973 A1 | 8/2016 |
| WO | 2016128974 A1 | 8/2016 |
| WO | 2016198682 A1 | 12/2016 |
| WO | 2017060500 A1 | 4/2017 |
| WO | 2019149880 A1 | 8/2019 |
| WO | 2019215063 A1 | 11/2019 |

OTHER PUBLICATIONS

Teng et al., "Systematical approach of formulation and process development using roller compaction," European Journal of Pharmaceutics and Biopharmaceutics, 2009, vol. 73, pp. 219-229.
Parikh, "Drugs and the Pharmaceutical Sciences", Handbook of Pharmaceutical Granulation Technology, 2010, Third Edition, vol. 198, Chapter 2 Theory of Granulation: An Engineering Perspective, Chapter 8 Roller Compaction Technology and Chapter 9 Wes Granulation in Low- and high—Shear Mixers.
Uros Markoja, Semaglutide-Experiment report for opposition against EP2827845B1, dated Sep. 24, 2019, pp. 1-6.
Valtrex prescribing information (valacyclovir hydrochloride caplets), GlaxoSmithKline, Oct. 2007, pp. 1-20.
Venables et al., "Powder Mixing," Drug Development and Industrial Pharmacy, 2001, vol. 27, No. 7, pp. 599-612.
Tyagi et al., "Oral peptide delivery: Translational challenges due to physiological effects," J. Controlled Release, 2018, vol. 287, pp. 167-176.

(56) References Cited

OTHER PUBLICATIONS

Dahlgren et al., "Intestinal absorption-modifying excipients: A current update on preclinical in vivo evaluations," European J. of Pharm. and Biopharmaceutics, 2019, vol. 142, pp. 411-420.
Figures presenting plasma concentration, described in EU Patent No. 2991671, issued Aug. 15, 2018.
FDA News Release, "FDA approved first oral GLP-1 treatment for type 2 diabetes," Sep. 20, 2019.
Carly Helfand, "Novo Nordisk wins FDA green light for "holy grail" diabetes drug Rybelsus," Fierce Pharma, Sep. 20, 2019, https://www.fiercepharma.com/pharma/novo-nordisk-wins-fda-green-light-for-holy-grail-oral-semaglutide, accessed Oct. 4, 2019.
Runge et al., "Crystal Structure of the Ligand-Bound Glucagon-Like Peptide-1 Receptor Extracellular Domain," J Biol Chem 2008, vol. 283, No. 17, pp. 11340-11347.
Adelhorst, K et al Journal of Biological Chemistry Structure Activity Studies of GLP-1 1994 269 9 6275-6278.
Knudsen, L.B. Journal of Medicinal Chemistry Glucagon-Like Peptide-1: The Basis of a New Class of Treatment for Type 2 Diabetes 2004 47 17 4128-4134.
Leger et al., "Identification of CJC-1131-Albumin Bioconjugate as a Stable and Bioactive GLP-1 (7-36) Analog," Bioorganic and Medicinal Chemistry Letters, vol. 14, pp. 4395-4398 (2004).
Pan et al., Design of a Long Acting Peptide Functioning as both a Glucagon-like Peptide-1 Receptor Agonist and a Glucagon Receptor Antagnist, "The Journal of Biological Chemistry", May 2006, vol. 281, No. 18, pp. 12506-12515.
The Medical Dictionary Online. http://cancerweb.ncl.ac.uklomd/about.html. 2005.
Nauck, M A. Regulatory Peptides. "Glucagon-Like Peptide 1 and its Derivatives in the Treatment od Diabetes." 2005. vol. 128(2). pp. 135-148.
David M. Irwin, Trout and chicken Proglucagon: Alternative Splicing Generates mRNA Transcripts Encoding Glucagon-Like Peptide 2, Molecular Endocrinology, 1995, vol. 9 No. 3, 267-277.
Full European prosecution file of EP 2 827 885 BI. Published Jan. 28, 2015, Available at the EPO Register, https://register.epo.org/application?number=EP13709231&Ing=en&tab=doclist, accessed May 31, 2019.
Post-published details of trial NCT01037582. First posted Dec. 23, 2009 https://clinicaltrials.gov/ct2/show/NCT01037582, accessed May 31, 2019.
Published details of trial NCT01037582 First Version Dec. 21, 2009 https://clinicaltrials.gov/ct2/history/NCT01037582?A=1&B=1&C=merged#StudyPageTop, accessed May 31, 2019.
Table summarizing the components of the tablet compositions B to F, described in EP Patent No. 2827885, issued Aug. 15, 2018.
Schematic drawing of tablets E and F described in EP Patent No. 2827885, issued Aug. 15, 2018,.
Overview of claim 1 of the main and auxiliary requests, European Application No. EP2651398, filed May 14, 2013.
GenScript, "Peptide YY (PYY) (3-36), human," https://www.genscript.com/peptide/RP10354-Peptide_YY_PYY_3_36_human.html, accessed Jan. 27, 2020.
Banakar et al., Critical Considerations in Pharmaceutical Bioequivalence Testing, Journal of Pharmacy of University of Marmara, 1995, vol. 11 Nos. 1-2, pp. 55-80.
Emisphere Technologies, Inc., Form 10-K, 2013 Annual Report, Published Mar. 31, 2014.
American Veterinary Medical Association, "The Veterinarian-Client-Patient Relationship (VCPR)," https://www.avma.org/policies/veterinarian-client-patient-relationship, accessed Mar. 11, 2020.
National Institute of Diabetes and Digestive and Kidney Diseases, "Prescription Medications to Treat Overweight and Obesity," Jul. 2016, 10 pages, retrieved on Apr. 13, 2020., URL: https://www.niddk.nih.gov/health-information/weight-management/prescription-medications-treat-overweight-obesity.
W.K. Sietsema, "The absolute oral bioavailability of selected drugs." Mar. 1989, International Journal of Clinical Pharmacology, Therapy and Toxicology, vol. 27, No. 4, pp. 179-211.

Declaration of Doctor Peter Rue, for EP2827885 dated Jul. 29, 2020.
Declaration of Professor Leon Aarons for EP2827885 dated Jul. 29, 2020.
Shajahan et al., A flexible technology for modified-release drugs: Multiple-unit pellet system (MUPS) May 2009, Journal of Controlled Release, vol. 147, No. 1, pp. 2-16.
Physicians' Desk Reference, 54th Edition, 2000, p. 1291.
Physicians' Desk Reference, 63rd Edition, 2009, p. 1638.
Arbit et al. "Oral heparin: status review". Thrombosis J, May 2006, vol. 4, No. 6, pp. 1-7.
Emisphere Announces License Agreement With Novo Nordisk to Develop Oral Formulation of GLP-1 Receptor Agonists for Diabetes, Jun. 23, 2008 retrieved from https://www.biospace.com/article/releases/emisphere-technologies-inc-announces-license-agreement-with-novo-nordisk-inc-to-develop-oral-formulation-of-glp-1-receptor-agonists-for-diabetes-/, 5 pages, retrieved on Dec. 16, 2020.
European Medicines Agency, Rybelsus EPAR Public Assessment Report, Jan. 30, 2020, pp. 1-152, p. 72.
Notice of Opposition by Galenicum, filed Dec. 9, 2020 in European Patent 3326620.
Notice of Opposition by Hexal Ag, filed Dec. 8, 2020 in European Patent 3326620.
Novo Nordisk starts phase 1 trial with long-acting oral GLP-1 analogue, Jan. 13, 2010, 2 pages retrieved from https://pipelinereview.com/index.php/2010011332046/Small-Molecules/Novo-Nordisk-starts-phase-1-trial-with-long-acting-oral-GLP-1-analogue.html, retrieved on Dec. 16, 2020.
Novo Nordisk, "Novo Nordisk to acquire Emisphere Technologies and obtain ownership of the Eligen® SNAC oral delivery technology", Nov. 6, 2020 retrieved from <https://www.novonordisk.com/content/nncorp/global/en/news-and-media/news-and-ir-materials/news-details.html?id=33374>, 3 pages retrieved on Dec. 16, 2020.
Notice of Opposition by Teva filed Dec. 4, 2020 in European Patent 3326620.
Full prosecution file of the opposed patent EP 3 326 620 B1, filed on Nov. 29, 2017 that can be found in European Patent register, 1,596 pages, https://reqister.epo.org/application?number=EP17204363&InQ=en&tab=doclist.
Granhall, Charlotte et al., "Safety and Pharmacokinetics of Single and Multiple Ascending Doses of the Novel Oral Human GLP-1 Analogue, Oral Semaglutide, in Healthy Subjects and Subjects with Type 2 Diabetes" Clinical Pharmacokinetics, published Dec. 18, 2018.
Hellriegel, Edward T. et al., "Interpatient variability in bioavailability is related to the extent of absorption: Implications for bioavailability and bioequivalence studies" Clinical Pharmacology & Therapeutics, Dec. 1996, vol. 60, No. 6, pp. 601-607.
King, Simon, "ViewPoints: Novo Nordisk R&D chief predicts an oral revolution for biologics" Nov. 14, 2018, Available from: [http://www.firstwordpharma.com/print/1604592?tsid=17].
Lee, Hye J., "Protein Drug Oral Delivery: The Recent Progress" Archives of Pharmacal Research, 2002, vol. 25, No. 5, pp. 572-584.
Madsen, Kjeld et al., "Structure—Activity and Protraction Relationship of Long-Acting Glucagon-like Peptide-1 Derivatives: Importance of Fatty Acid Lenght, Polarity, and Bulkiness" J. Med. Chem., 2007, vol. 50, pp. 6126-6132.
Morishita, Mariko et al., "Is the oral route possible for peptide and protein drug delivery?" Drug Discovery Today, Oct. 2006, vol. 11, No. 19/20, pp. 905-910.
Novo Nordisk Company announcement No. 14/2015, Novo Nordisk announces positive results for phase 2 trial with oral semaglutide in people with type 2 diabetes, www.novonordisk.com CVR No. 24256790, dated Feb. 20, 2015, p. 1-2.
Novo Nordisk Company announcement No. 52/2015, Novo Nordisk to initiate phase 3a development of oral semaglutide, a once-daily oral GLP-1 analogue, www.novonordisk.com CVR No. 24256790, dated Aug. 26, 2015, p. 1-2.
Novo Nordisk Company announcement No. 17/2018, Novo Nordisk successfully completes the first phase 3a trial, Pioneer 1, with oral semaglutide, www.novonordisk.com CVR No. 24256790, dated Feb. 22, 2018, p. 1-3.

(56) References Cited

OTHER PUBLICATIONS

Novo Nordisk Company announcement No. 47/2018, Oral semaglutide shows superior improvement in HbA1C vs empagliflozin in the Pioneer 2 trial, www.novonordisk.com CVR No. 24256790, dated May 29, 2018, p. 1-3.
Novo Nordisk Company announcement No. 51/2018, Oral semaglutide shows statiistically significantly greater reductions in HbA1c and weight compared to Victoza® and sitagliptin in the Pioneer 4 and 7 trials, www.novonordisk.com CVR No. 24256790, dated Jun. 20, 2018, p. 1-4.
Novo Nordisk Company announcement No. 53/2018, Oral semaglutide shows superior reductions in HbA1c and weight compared to sitagliptin in the long-term safety and efficacy trial, Pioneer 3, www.novonordisk.com CVR No. 24256790, dated Jun. 28, 2018, p. 1-3.
Novo Nordisk Company announcement No. 66/2018, Oral semaglutide provides superior HbA1c and weight reductions versus placebo in people with type 2 diabetes and renal impairment in the Pioneer 5 trial, www.novonordisk.com CVR No. 24256790, dated Aug. 20, 2018, p. 1-3.
Novo Nordisk Company announcement No. 74/2018, Oral semaglutide demonstrates greater reductions in HbA1c and body weight and comparable number of adverse events vs dulaglutide in Japanese people with type 2 diabetes, www.novonordisk.com CVR No. 24256790, dated Sep. 20, 2018, p. 1-3.
Novo Nordisk Company announcement No. 81/2018, Oral semaglutide demonstrates statistically significant reductions in HbA1c and body weight in people with long duration of type 2 diabetes treated with insulin, www.novonordisk.com CVR No. 24256790, dated Oct. 26, 2018, p. 1-3.
Novo Nordisk Company announcement No. 89/2018, Oral semaglutide demonstrates greater reductions in both HbA1c and body weight compared to Victoza® in Japanese people with type 2 diabetes, www.novonordisk.com CVR No. 24256790, dated Nov. 22, 2018, p. 1-2.
Novo Nordisk Company announcement No. 90/2018, Oral semaglutide demonstrates a favourable cardiovascular safety profile and a significant reduction in cardiovascular death and all-casue mortality in people with type 2 diabetes in the Pioneer 6 trial, www.novonordisk.com CVR No. 24256790, dated Nov. 23, 2018, p. 1-3.
Owens, D.R. et al., "Alternative routes of insulin delivery" Diabetic Medicine, 2003, vol. 20, pp. 886-898.
Thepharmaletter, "'8-10 years ahead' of field in oral delivery, senior execs say Novo is becoming a GLP-1 company" May 16, 2018, [cited Jan. 24, 2019] Available from: [https://www.thepharmaletter.com/article/8-10-years-ahead-of-field-in-oral-delivery-senior-execs-say-novo-nordisk-is-becoming-a-glp-1-company].
Watson, Estelle et al., "Population Pharmacokinetics of Liraglutide, a Once-Daily Human Glucagon-Like Peptide-1 Analog, in Healthy Volunteers and Subjects With Type 2 Diabetes, and Comparison to Twice-Daily Exenatide" J. Clin Pharmacology, 2010, vol. 50, pp. 886-894.
Antony J Hickey et al., Pharmaceutical Process Engineering (Second edition) (2010) p. 155-168.
Bruce J. Aungst, "Absorption enhancers: applications and advances," The MPS Journal, 2011, vol. 14, No. 1, pp. 10-18.
Diabetes Close Up, Baby Steps, Mar./Apr. 2011, No. 106, pp. 1-50.
Dilip M. Parikh, Handbook of Pharmaceutical Granulation Technology (Second edition) (2005), Process-related variables, pp. 7-19 and 311-331.
EP Application 12160743, filed Mar. 22, 2012.
EP Application 13153459, filed Jan. 31, 2013.
Full European prosecution file of EP 2 827 885 BI. Available at the EPO Register, https://register.epo.org/application?number=EP13709231&Ing=en&tab=doclist, accessed May 31, 2019.
Handbook of Pharmaceutical Granulation Technology, Drugs and pharmaceutical sciences, Second Edition, 2005, vol. 154, Introduction, pp. 1-6.
Post-published details of trial NCT01037582 https://clinicaltrials.gov/ct2/show/NCT01037582, accessed May 31, 2019.
Published details of trial NCT01037582 (Dec. 2009) https://clinicaltrials.gov/ct2/history/NCT01037582?A=1&B=1&C=merged#StudyPageTop, accessed May 31, 2019.
R. F. Witkamp, "Current and Future Drug Targets in Weight Management," Pharm Res, 2011, vol. 28, pp. 1792-1818.
Salem et al., "Approaches to the pharmacological treatment of obesity," Expert Rev Clin Pharmacol, 2010, vol. 3, No. 1, pp. 73-88.
Barrera-Medrano et al., The Handbook of Powder Technology "Granulation", Chp. 25 granule structure, vol. 11, 2007, p. 1189-1212.
U.S. Appl. No. 61/748,840, filed Jan. 4, 2013.
Steinert et al., Oral administration of glucagon-like peptide 1 or peptide 3-36 affect food intake in healthy male subjects, "American Society for Nutrition", Am J Clin Nutr, 2010, vol. 92, pp. 810-817.
Nauck et al., 2012, Abstracts of the 48th European Association for the Study of Diabetes Annual Meeting of the EASD, Oct. 1-5, 2012, Berlin, Germany, Diabetologia, 2012, vol. 55, Suppl, S7.
Fonseca et al., "Efficacy and Safety of the Once-Daily GLP-1 Receptor Agonist Lixisenatide in Monotherapy," Diabetes Care, Jun. 2012, vol. 35, pp. 1225-1231.
Study NCT02014259, version 1, published Dec. 18, 2013, accessed Jun. 5, 2019.
"Drug Absorption, Distribution and Elimination; Pharmacokinetics" http://www.columbia.edu/itc/gsas/g9600/2004/GrazianoReadings/Drugabs.pdf, available since at least Apr. 24, 2006, accessed on Jun. 3, 2019.
Standards of Medical Care in Diabetes-2010, "Diabetes Care", vol. 33, supplement 1, Jan. 2010, pp. S11-S61, care.diabetesjournals.org.
Andrew D. Morris, MD, "Addressing dosing frequency in diabetes: a simple approach to improving adherence to therapy and clinical outcomes," The Diabetes Educator, 2003, vol. 29, No. 3, pp. 440-453.
B.J. Aungst, "Absorption Enhancers: Applications and Advances," The AAPS Journal, 2012, vol. 14, No. 1, pp. 10-18.
ClinicalTrials.gov archive: History of Changes for Study NCT01686945, trackchange of version of Apr. 15, 2013 (published Apr. 16, 2013) as compared to version of Sep. 13, 2012 (published Sep. 18, 2012).
ClinicalTrials.gov archive: History of Changes for Study NCT01923181 (NN9924-3790), Jan. 31, 2018, 14 Pages.
Clinicaltrials.gov, NCT01686945, page as viewed in Apr. 2013, https://clinicaltrials.gov/ct2/history/NCT01686945?A=5&B=5&C=merged#StudyPageTop.
Coskun et al., "LY3298176, a novel dual GIP and GLP-1 receptor agonist for the treatment of type 2 diabetes mellitus: From discovery to clinical proof of concept," Molecular Metabolism, 2018, vol. 18, pp. 3-14.
David J. Edmonds et al., "Oral GLP-1 Modulators for the Treatment of Diabetes". Annual Reports in Medicinal Chemistry, 2013, 1st edition, vol. 48, Chapter 9, pp. 119-130.
DJ. Birkett, "Pharmacokinetics made easy 11 Designing dose regimens," Australian Prescriber, 1996, vol. 19, No. 3, pp. 76-88.
E. Mutschler et al., Mutschler Arzneimittelwirkungen, Lehrbuch der Pharmakologie und Toxikologie, 8th edition 2001, pp. 48-51.
Emisphere Annual Report and Proxy 2013, publicly available at the latest on Apr. 17, 2014, 127 pages.
Araujo et al., "Oral Delivery of Glucagon-Like Peptide-1 and Analogs: Alternatives for Diabetes Control?", Journal of Diabetes Science and Technology, Nov. 2012, vol. 6, No. 6, pp. 1486-1497.
Aungst, "Absorption Enhancers: Applications and Advances," The AAPS Journal, 2012, vol. 14, No. 1, pp. 10-18.
Baekdal et al., "Pharmacokinetics, Safety, and Tolerability of Oral Semaglutide in Subjects With Hepatic Impairment" The Journal of Clinical Pharmacology, Apr. 2018, vol. 58, pp. 1314-1323.
Buckley, Stephen T. et al., "Transcellular stomach absorption of a derivatized glucagon-like peptide-1 receptor agonist" Science Translational Medicine, Nov. 14, 2018, vol. 10, No. 14, eaar7047 pp. 1-13.
Decision of Case No. T 1777/21, dated Dec. 5, 2023.
Drucker, "Mechanisms of Action and Therapeutic Application of Glucagon-like Peptide-1", Cell Metabolism Review, Apr. 2018, vol. 27, pp. 740-756.
Drucker, "Advances in oral peptide therapeutics", Nat. Rev. Drug Discov., Dec. 17, 2019, vol. 19, pp. 277-289.

(56) References Cited

OTHER PUBLICATIONS

Edmonds et al., "Oral GLP-1 Modulators for the Treatment of Diabetes", Annual Reports in Medicinal Chemistry, 2013, 1st edition, vol. 48, Chapter 9, pp. 119-130.
FDA Approval Letter for Ozempic®, Dec. 5, 2017.
Granhall et al., "Pharmacokinetics, Safety and Tolerability of Oral Semaglutide in Subjects with Renal Impairment" Clinical Pharmacokinetics, Apr. 2018, vol. 57, pp. 1571-1580.
Granhall et al., "Safety and Pharmacokinetics of Single and Multiple Ascending Doses of the Novel Oral Human GLP-1 Analogue, Oral Semaglutide, in Healthy Subjects and Subjects with Type 2 Diabetes," Clinical Pharmacokinetics, Dec. 2018, pp. 1-11.
International Preliminary Report on Patentability issued in Application No. PCT/EP2019/052487, mailed Aug. 4, 2020, 7 pages.
Karandule et al., "Tablet Binders" International Journal for Research in Applied Science & Engineering Technology (IJRASET), Jan. 2023, vol. 11, No. 1, pp. 675-681.
Knudsen et al., "The discovery and development of liraglutide and semaglutide," Frontiers in Endocrinology, Apr. 2019, vol. 10, Article 155, pp. 1-32.
Li et al., "Impact of Sodium N-[8-(2-Hydroxybenzoyl)amino]-caprylate on Intestinal Permeability for Notoginsenoside R1 and Salvianolic Acids in Caco-2 Cells Transport and Rat Pharmacokinetics", Molecules, Nov. 2018, vol. 23, No. 2990, pp. 1-14.
Morin et al., "The Effect of Lubricants on Powder Flowability for Pharmaceutical Application", AAPS PharmSciTech, Sep. 2013, vol. 14, No. 3, pp. 1158-1168.
NCT01037582 Trial ID: Clinical Trial Report NN9924-3691 Investigation on Safety, Tolerability and Bioavailability of Oral Semaglutide in Healthy Male Subjects, Apr. 6, 2011, 761 pages.
Rowe et al., "Handbook of Pharmaceutical Excipients", Pharmaceutical Press, 2009, Ed. Sixth edition, p. 286-288, 404-407, 651-653.
Search Report issued in EP Application No. 23182039.0, mailed Feb. 29, 2024, in 8 pages.
Twarog et al., "Intestinal Permeation Enhancers for Oral Delivery of Macromolecules: A Comparison between Salcaprozate Sodium (SNAC) and Sodium Caprate (C 10)", Feb. 2019, vol. 11, No. 2, p. 78, 21 pages.
Voigt, R., "Lehrbuch der pharmazeutischen Technologie", Verlag Chemie, Weinheim 1984, pp. 156-158, 162, 178-179, 645-646 and 659-660.
Maher et al., "Intestinal permeation enhancers for oral peptide delivery", Adv. Drug Deliv. Rev., Accepted Manuscript, Jun. 2016, vol. 106, pp. 277-319.
Full prosecution file of the parent patent EP2651398B1, filed May 14, 2013 that can be found in European Patent register, 4309 pages, accessed Dec. 3, 2021, https://register.epo.org/application?No. EP11805824&Ing=en&tab=doclist.
Kapitza et al., "Safety, tolerability, pharmacokinetics (PK)/pharacodynamics (PD) of single escalating doses of semaglutide, a unique once weekly GLP1 analogue, in healthy male subjects," Presentation at: 48th EASD Annual Meeting. Berlin, Germany, Oct. 1-5, 2012.
DRA. Carmen Gloria Aylwin H., Nuevos Fármacos en Diabetes Mellitus (New Drugs for Treatment of Diabetes Mellitus), Rev. Med. Clin. Condes, 2016, vol. 27, No. 2, pp. 235-256.
Declaration of Tine. A Bækdal, dated Apr. 28, 2021.
Product label for Rybelsus™ as issued by the FDA, Sep. 2019.
Bryan J. Ennis, "Theory of Granulation: An Engineering Perspective," Handbook of Pharmaceutical Granulation Technology, 2005, pp. 7-78.
Pechenov et al., "Development of an orally delivered GLP-1 receptor agonist through peptide engineering and drug delivery to treat chronic disease," Scientific Reports, Nov. 2021, vol. 11, No. 22521, pp. 1-15.
Wong et al., "Estimation of clinical trial success rates and related parameters," Biostatistics, Jan. 2018, vol. 20, No. 2, pp. 273-286.
Novo Nordisk Reply to Office Action dated Jul. 3, 2008 in EP1863839.

Gomez-Orella, "Strategies to Improve Oral Drug Bioavailability," Expert Opin Drug Deliv, 2005, vol. 2, No. 3: pp. 419-433.
Humphrey, M. J., "The Oral Bioavailability of Peptides and Related Drugs. In Delivery Systems for Peptide Drugs," Davis, S.S., Illum, L., Tomlinson, E., Eds.; Springer: Boston, MA, 1986; pp. 139-151.
Novo Nordisk's reply to the examination division dated Nov. 18, 2016 in EP Application 13729743.8, 3 pages.
Novo Nordisk' s reply to the opposition grounds of WO2012/080471, corresponding to EP2651398, dated Feb. 15, 2019, 40 pages.
Kwan et al., "Factors Affecting Tablet Disintegration," Journal of the American Pharmaceutical Association, Scientific Edition, Apr. 1957, vol. XLVI, No. 4, pp. 236-239.
Viscasillas i Clerch, "Aportacion al diseno de un nuevo excipiente tipo "coprocessed product" para compresion directa," Universitat de Barcelona, 2008, pp. 159-160.
Pharmaceutical Binders and Their Function in Directly Compressed Tablets, Mechanistic Studies on the Effect of Dry Binders on Mechanical Strength, Pore Structure and Disintegration of Tablets, Dissertation for the Degree of Doctor of Philosophy (Faculty of Pharmacy) in Pharmaceutics presented at Uppsala University in 2000 By Sofia Mattsson, pp. 32-34.
Extract of the opposed patent EP2863895, 2 pages, full prosecution file can be found in European Patent register https://register.epo.org/application?number=EP13729743&Ing=en&tab=doclist.
Anne Mari Juppo, "Porosity parameters of lactose, glucose and mannitol tablets obtained by mercury porosimetry," International Journal of Pharmaceutics, 1996, vol. 129, pp. 1-12.
Michael E. Aulton., "Aulton's Pharmaceutics. The design and manufacture of medicines" Churchill Livingstone Elsevier, 2007, Ed. 3rd, Chapter 21, pp. 286-303.
Linda Felton, "Remington Essentials of Pharmaceutics," Pharmaceutical Press, 2012, Chapter 6, pp. 63-80 and Chapter 30, pp. 581-610.
Qiu et al., "Developing Solid Oral Dosage Forms" Pharmaceutical Theory and Practice, Academic Press, 2009, 1st Edition, pp. 175-186.
James Swarbrick, "Encyclopedia of Pharmaceutical Technology. vol. 1," Informa Healthcare USA, Inc., 2007, Ed. 3rd, pp. 164-175 and 988-1000.
EP application No. 12160743.6, filed Mar. 22, 2012.
Betts et al., Chapter 14, "Amino Acid Properties and Consequences of Substitutions," Bioinformatics for Geneticists (2003) ed. By Barnes and Gray, John Wiley & Sons, Ltd., pp. 289-316.
Kojima S et al. A role for pancreatic polypeptide in feeding and body weight regulation, "Peptides", Year 2007, vol. 28, No. 2, pp. 459-463.
Lin Shu et al. Critical Role of Arcuate Y4 Receptors and the Melanocortin System in Pancreatic Polypeptide-Induced Reduction in Food Intake in Mice, "PLOS One" Year 2009, vol. 4, No. 12, pp. e8488-e8488.
Ito T et al, Effects of peripheral administration of PYY3-36 on feed intake and; plasma acyl-ghrelin levels in pigs, Journal of Endocrinology, Year 2006, vol. 191, pp. 113-119.
Ortiz A et al, A Novel Long-Acting Selective Neuropeptide Y2 Receptor Polyethylene Glycol-Conjugated Peptide Agonist Reduces Food Intake and Body Weight and Improves Glucose Metabolism in Rodents , The Journal of Pharmacology and Experimental Therapeutics (2007), vol. 323, No. 2, pp. 692-700.
Roger Reidelberger et al., Effects of Glycine-Extended and Serine 13-Phosphorylated Forms of Peptide YY on Food Intake in Rats, Peptides, Year 2011; vol. 32, No. 4, pp. 770-775.
Søren L. Pedersen et al., Peptide hormone isoforms: N-terminally branched PYY3-36 isoforms give improved lipid and fat-cell metabolism in diet-induced obese mice, Journal of Peptide Science, Year 2010, vol. 16, Issue 11, pp. 664-673.
Van den Hoek A. et al., Chronic PYY3-36 treatment promotes fat oxidation and ameliorates insulin resistance in C57BL6 mice, American Journal of Physiology-Endocrinology and Metabolism, Year 2007, 292, pp. E238-E245.
Adrian et al., Gut, 1978, vol. 19, No. 10, pp. 907-909.

(56) References Cited

OTHER PUBLICATIONS

Heizmann et al., Peptide Research, "Synthesis of an N-3-guanidinopropylglycine (Narg) Derivative as a Versatile Building Block for Solid-Phase Peptide and Peptoid Synthesis", 1994, vol. 7, No. 6, pp. 328-332.
Batterham, R.L. et al., "Gut Hormone PYY3-36 Physiologically Inhibits Food Intake", Nature, 2002, vol. 418, pp. 650-654.
Bowie et al. (Science, 1990, 247:1306-1310).
Burgess et al. (J. Cell Biol. 111:2129-2138, 1990).
Lazar et al. (Mol. Cel. Biol., 8:1247-1252, 1988).
Bork (Genome Research, 2000, 10:398-400).
T.W. Schwartz., "Pancreatic Polypeptide: A Hormone Under Vagal Control", Gastroenterology. 1983, vol. 85, pp. 1411-1425.
Whitcomb. Am. J. Physiol. "Characterization of saturable binding sites for circulating pancreatic polypeptide in rat brain." 1990 vol. 259 G687-G691.
Jorgensen, J. Ch et al. Euro. J. Pharmacol. "Structure-function studies on neuropeptide Y and pancreatic polypeptide—evidence for two PP-fold receptors in vas deferens" 1990 vol. 186: 105-114.
Cooke, D et al. Nature Reviews. "The obesity pipeline: current strategies in the development of anti-obesity drugs" 2006 vol. 5: 919-930.
Kamiji, M.M et al. Current Topics in Medical Chemistry "NPY Y2 and Y4 receptors selective ligands: promising anti-obesity drugs?" 3008 vol. 7: 1734-1742.
Sainsbury, A. et al. Mol Nad Cell Biol "Synergistic Effects of Y2 and Y4 Receptors on Adiposity and Bone Mass Revealed in Double Knockout Mice" vol. 23: 5225-5233.
Sampson, W.R. J. Pep. Sci. "The Synthesis of 'Difficult' Peptides Using 2-Hydroxy-4-Methoxybenzyl or Pseudoproline Amino Acid Building Blocks: a Comparative Study" 1999 vol. 5: 403.
Knudsen et al. J Med Chem. "Potent Derivatives of Glucagon-Like Peptide-1 with Pharmacokinetic Properties Suitable for Once Daily Administration" 2000. vol. 43(9). p. 1664-1669.
Boggiano, M.M. et al., "PYY3-36 as an anti-obesity drug target", Obesity Reviews. 2005 vol. 6: 307-322.
Dodson, Shontelle et al "Muscle Wasting in Cancer Cachexia: Clinical Implications, Diagnosis, and Emerging Treatment Strategies" Annu. Rev. Med. 2011 vol. 62 pp. 265-279.
Chatterjee et al., "Glucagon-like peptide-1 receptor agonists favorably address all components of metabolic syndrome", World Journal of Diabetes, Oct. 2016, vol. 7, No. 18, pp. 441-448.
EU Clinical Trials Register Summary EudraCT No. 2012-004994-16 (NN9924-3790), published Jul. 30, 2013, accessed Jun. 7, 2019.
EU Leaflet of Linagliptin, 1st authorization in EU: Aug. 24, 2011 (p. 2, 3 & 13).
EU Leaflet of Linagliptin-Metformin, 1st authorization in EU:Jul. 20, 2012 (p. 2, 3 & 21).
EU Leaflet of Metformin, 1st authorization in EU: Jul. 31, 2001 (p. 1, 2 & 11).
EU Leaflet of Saxagliptin, 1st authorization in EU: Oct. 1, 2009 (p. 1 & 18).
EU Leaflet of Sitagliptin, 1st authorization in EU: Mar. 21, 2007 (p. 2, 3 & 16).
EU Leaflet of Sitagliptin-Metformin, 1st authorization in EU: Jul. 16, 2008 (p. 2, 3 & 20).
EU Leaflet of Vildagliptin, 1st authorization in EU: Sep. 26, 2007(p. 2, 3 & 18).
EU Leaflet of Vildagliptin-Metformin, 1st authorization in EU: Nov. 14, 2007 (p. 2, 3 & 21).
European Patent Application 13166205, filed May 2, 2013.
Geiser et al., "Clinical Pharmacokinetics of Dulaglutide in Patients with Type 2 Diabetes: Analyses of Data from Clinical Trials". Clinical Pharmacokinetics, 2016, vol. 55, pp. 625-634.
Granhall et al., Safety and Pharmacokinetics of Single and Multiple Ascending Doses of the Novel Oral Human GLP-1 Analogue, Oral Semaglutide, in Healthy Subjects and Subjects with Type 2 Diabetes, Clinical Pharmacokinetics, Dec. 2018.
Leon Shargel, Applied Biopharmaceutics and Pharmacokinetics, 6th edition, 2012, Chapter 8, Multiple-Dosage Regimens, pp. 153-175.
Linda Felton, Remington, Essentials of Pharmaceutics, 2012, Chapter 37, pp. 708-709 and 712-713.
M. Gonzalez Brao, "48th Annual Meeting of the European Association for the Study of Diabetes (EASD)," Drugs of the Future, 2012, vol. 37, No. 12, pp. 871-878.
Malcolm Rowland et al., "Clinical Pharmacokinetics and Pharmacodynamics : Concepts and Applications," Chapter 11—Multiple-Dose Regimens (pp. 293-329); 4th ed.; Philadelphia: Wolters Kluwer Health/Lippincott William & Wilkins, 2011.
Product details regarding David J. Edmonds et al., "Oral GLP-1 Modulators for the Treatment of Diabetes". Annual Reports in Medicinal Chemistry (2013), 1st edition, vol. 48, chapter 9, pp. 119-130, from amazon.com, accessed on May 3, 2019.
Prosecution file of EP2991671B1, available at the EPO Register, the pdf is not attached. https://register.epo.org/application?number=EP14721834&lng=en&tab=doclist, accessed Jun. 14, 2019.
Quianzon et al., "Lixisenatide—Once daily glucagon-like peptide-1 receptor agonist in the management of type 2 diabetes," 2011, US Endocrinology, Diabetes Management, vol. 7, No. 2, pp. 104-109.
Rosenstock et al., "Potential of albiglutide, a long-acting GLP-1 receptor agonist, in type 2 diabetes: a randomized controlled trial exploring weekly, biweekly, and monthly dosing". Diabetes Care, 2009, vol. 32, No. 10, pp. 1880-1886.
S. Dhillon et al., "Basic Pharmacokinetics," Clinical Pharmacokinetics, 2006, Pharmaceutical Press, London; Chapter 1, pp. 1-44.
Sarfaraz K. Niazi, Handbook of Bioequivalence Testing, 2007, p. 13-15.
Schematic overview of sequences and plasma half-life in humans of "GLP-1 peptides" in Sanofi Opposition in EP2991671, dated May 22, 2019, 1 Page.
Sisson, "Liraglutide: clinical pharmacology and considerations for therapy," Pharmacotherapy, 2011, vol. 31, pp. 896-911.
Study NCT01686945, version 1, published Sep. 18, 2012, accessed Jun. 6, 2019.
Study NCT01866748, version 1, published May 31, 2013, accessed Jun. 6, 2019.
Study NCT01923181, version 1, published Aug. 15, 2013, accessed Jun. 5, 2019.
Submission of Novo Nordisk dated Feb. 15, 2019 in response to oppositions against EP2651398B1.
Chae S Y et al., Journal Title: Journal of The Controlled Release, Title: The Fatty Acid Conjugated Exendin-4 Analogs for Type 2 Antidiabetic Therapeutics , Year: 2010, vol. 144, pp. 10-16.
EP09179390.1 Priority Application Filed on Dec. 16, 2009 by Novo Nordisk. Double-Acylated GLP-1 Derivatives, 100 pages.
EP10190515.6 Priority Application Filed on Nov. 9, 2010 by Novo Nordisk. Double-Acylated GLP-1 Derivatives, 162 pages.
Dolensky et al., "New Building Blocks for Fluorinated Imidazole," Jorunal of Organic Chemistry, vol. 66(13), pp. 4687-4691 (2001).
Knudsen et al., "Potent Derivatives of Glucagon-Like Peptide-1 With Pharmacokinetic Properties Suitable for Once Daily Administration," Journal of Medicinal Chemistry, 2000, vol. 43(9), pp. 1664-1669.
Dumelin et al.., "A Portable Albumin Binder From a Dna-Encoded Chemical Library", Angewandte Chemie (International Edition in English), vol. 47(17), pp. 3196-3201 (2008).
Rawlay SS et al. Journal of Organic Chemistry. "Oxidation of Primary, Secondary, and Tertiary Amines With Neutral Permanganate. A Simple Method for Degrading Amines to Aldehydes and Ketones." 1967. vol 32(10). pp. 3129-3131.
Travis B R et al. Organic Letters. "Facile Oxidation of Aldehydes to Acids and Esters With Oxone." 2003. vol. 5(7). pp. 1031-1034.
Murage E N et al. Bioorganic & Medicinal Chemistry. "Search for ¿-Helical Propensity in the Receptor-Bound Conformation of Glucagon-Like Peptide-1." 2008. vol. 16. pp. 10106-10112.
Guohu et al "Progress of Pharmaceutical Studies on Diabetes" Practical Pharmacy and Clinic, 2007, vol. 10, No. 1, pp. 56-57.
Zheng, "Formulation and Analytical Development for Low-Dose Oral Drug Products," John Wiley & Sons, Inc., 2009, p. 194.

(56) References Cited

OTHER PUBLICATIONS

"International Nonproprietary Names for Pharmaceutical Substances (INN)," Who Drug Information, 2009, vol. 23, No. 2, p. 129.
Rowe et al., "Sodium Lauryl Sulfate," Handbook of Pharmaceutical Excipients, 6th Edition, 2009, pp. 651-653.
Ajaz S. Hussain, "A Collaborative Search for Efficient Methods of Ensuring Unchanged Product Quality and Performance During Scale-Up of Immediate-Release Solid Oral Dosage Forms," Pharmaceutical Process Scale-Up, 2002, 1st Edition, Chapter 11, pp. 325-352.
Bai et al., Excipient Development for Pharmaceutical, Biotechnology, and Drug Delivery Systems, 2006, Chapter 12, pp. 181-185.
C. M. Keck et al., "Moderne Pharmazeutische Technologie—Lehbuch fur Studierende," 1. Auflage (2009), Kapitel 1.2 H. J. Ji.inginger, "Delivery Systeme fur die perorale Applikation van Peptiden," pp. 1-14.
European Application No. 12172739.0, filed Jun. 20, 2012.
File History of European Patent 2827845, filed Mar. 15, 2013.
File History of U.S. Appl. No. 61/662,456, filed Jun. 21, 2012.
Rowe et al., "Magnesium Stearate" and "Sodium Lauryl Sulfate", Handbook of Pharmaceutical Excipients, 6th Edition, 2009, pp. 404-407 and 651-653.
History of changes for clinical trial NCT01037582, from Mar. 17, 2011, https://clinicaltrials.gov/ct2/history/NCT01037582?A=5&C=merged#StudyPageTop.
Kikuta et al., "Effect of Mixing Time on the Lubricating Properties of Magnesium Stearate and the Final Characteristics of the Compressed Tablets," Drug Development and Industrial Pharmacy, 1994, vol. 20, No. 3, pp. 343-355.
Aulton., "Chapter 16—The gastrointestinal tract—physiology and drug absorption", Pharmaceutics The Science of Dosage Form Design, 2002, 2nd Ed,, pp. 217-218.
"Food's journey through the digestive system" Science Learning Hub, Jul. 2011, in 7 pages, retrieved from: <https://www.sciencelearn.org.nz/resources/1849-food-s-journey-through-the-digestive-system>.
Saigal et al., "Microcrystalline Cellulose as a Versatile Excipient in Drug Research", Journal of Young Pharmacists, Jan. 2009, vol. 1, pp. 6-12.
European Patent Application 18171046.8, filed May 7, 2018 in 55 pages.
"Rote Liste 1999", Arzneimittelverzeichnis des Bundesverbandes der Pharmazeutischen Industrie e.V. (BPI), Edition Cantor Verlag, section: "Alphabetisches Verzeichnis der Fertigarzneimittel", item 84 026,"Nicotinsaureamid 200 mg".
Muscaritoli, Maurizio et al "Prevention and Treatment of Cancer Cachexia: New Insights into an Old Problem." European Journal of Cancer, 2006 vol. 42 pp. 31-41.
Soeren L. Pedersen et al., Peptide hormone isoforms: N-terminally branched PYY3-36 isoforms give improved lipid and fat-cell metabolism in diet-induced obese mice, Journal of Peptide Science, Year 2010, vol. 16, Issue 11, pp. 664-673.
Van den Hoek A. et al., Chronic PYY3-36 treatment promotes fat oxidation and ameliorates insulin resistance in C57BL6 mice, American Journal of Physiology-Endocrinology and Metabolism, Year 2007, vol. 292, No. 1 pp. E238-E245.
Kouki Kitagawa et al: Solution synthesis of human peptide YY(hPYY), Chemical & Pharmaceutical Bulletin, Year Jun. 1, 1990 vol. 38, No. 6, pp. 1731-1734.
Ortiz A. et a lA Novel Long-Acting Selective Neuropeptide Y2 Receptor Polyethylene Glycol-Conjugated Peptide Agonist Reduces Food Intake and Body Weight and Improves Glucose Metabolism in Rodents, The Journal of Pharmacology and Experimental Therapeutics Year 2007, vol. 323 No. 2, pp. 692-700.
Roger Reidelberger et al: "Effects of glycine-extended and serine-phosphorylated forms of peptide YY on food Intake in rats", Peptides, Peptides Year 2011,vol. 32, No. 4, pp. 770-775.
Van den Hoek A. et al Chronic PYY3-36 treatment promotes fat oxidation and ameliorates insulin resistance in C57BL6 mice American Journal of Physiological Endocrinology and Metabolism Year 2006, vol. 292, No. 1 pp. E238-E245.
Balasubramaniam et al., "Structure-Activity Studies Including a psi(CH2-NH) Scan of Peptide YY (PYY) Active Site, PYY(22-36), for Interaction with Rat Intestinal PYY Receptors: Development of Analogues with Potent in Vivo Activity in the Intestine," J. Med. Chem., 2000, vol. 43, pp. 3420-3427.
Atherosclerosis, from http://www.merckmanuals.com/professional/cardiovascular-disorders/arteriosclerosis/atherosclerosis, pp. 1-14, accessed Dec. 29, 2015.
Diabetes, from http://www.merckmanuals.com/professional/endocrine-and-metabolic-disorders/ . . . , pp. 1-34, accessed Sep. 2, 2016.
Dyslipidemia, from http://www.merckmanuals.com/professional/endocrine-and-metabolic-disorders/lipid-dis . . . , pp. 1-11, accessed Dec. 29, 2015.
Fatty Liver Disease, from http://www.webmd.com/hepatitis/fatty-liver-disease?page=2&print=true, pp. 1-4, accessed Dec. 29, 2015.
Nabel, "Cardiovascular Disease," New Engl. J. Med., 2003, vol. 349, pp. 60-72.
Neary et al., "Peptide YY: Food for thought," Physiology & Behavior 97: 616-619 (2009).
Nonatheromatous Arteriosclerosis, from http://www.merckmanuals.com/professional/cardiovascular-disorders/arteriosclerosis/non . . . , pp. 1-2, accessed Dec. 29, 2015.
Sam et al., "Selective Ablation of Peptide YY Cells in Adult Mice Reveals Their Role in Beta Cell Survival," Gastroenterology, 143:459-468 (2012).
Vincent et al., "The satiety hormone peptide YY as a regulator of appetite," J Clin Pathol 61 :548-552 (2008).
Zhao Na et al., "PYY and obesity (summary)," Sports and Research Education, 2012, vol. 27, No. 3, pp. 102-107.
Huang Lan et al., "Relationship between Peptide Tyrosine-Tyrosine 3-36 and Ingestion Regulation," Hubei Agriculture Sciences, 2009, vol. 48, No. 10, pp. 2591-2594.
Zhao Biqian et al., "Regulation of PYY on Animal Food Intakes," Feed Industry, 2010, vol. 31, No. 18, pp. 51-55.
Beglinger et al. "Pharmacokinetics and pharmacodynamic effects of oral GLP?1 and PYY3?36: a proof?of?concept study in healthy subjects." Clinical Pharmacology & Therapeutics, Oct. 2008, vol. 84, No. 4, pp. 468-474.
Schmidt et al., "Effects of PYY3-36 and GLP-1 on energy intake, energy expenditure, and appetite in overweight men." American Journal of Physiology-Endocrinology and Metabolism, Apr. 2014, vol. 306, No. 11, pp. E1248-E1256.
Steinert et al., "Oral administration of glucagon-like peptide 1 or peptide YY 3-36 affects food intake in healthy male subjects." The American journal of clinical nutrition, Oct. 2010, vol. 92, No. 4, p. 810-817.
Cox Gad, Shayne, "Pharmaceutical Manufacturing Handbook Production and Processes," Hoboken, New Jersey: Wiley-Interscience A John Wiley & Sons, Inc., 2008, pp. 235-265 and 881-1222.
Hancock et al., "The Relative Densities of Pharmaceutical Powders, Blends, Dry Granulations, and Immediate-Release Tablets," Pharmaceutical Technology, Apr. 2003, p. 64-80.
Hoffman et al., "Eligen insulin—a system for the oral delivery of insulin for diabetes," IDrugs, 2008, vol. 11, pp. 433-441.
Lowenthal, Werner, "Disintegration of Tablets" Journal of Pharmaceutical Sciences, Nov. 1972, vol. 61, No. 11, pp. 1695-1711.
Poole, John W., "Effects of Formulation and Dosage Form on Drug Bioavailability" Principles and Perspectives in Drug Bioavailability, Chapter 3, Karger, 1979, pp. 59-89.
Rudnic et al., "Oral Solid Dosage Forms," Chapter 45, Remington—The Science and Practice of Pharmacy, Philadelphia, PA: Lippincott Williams & Wilkins, 2006, Ed. 21st, pp. 889-927.
Tong, W.Q., "Molecular and Physicochemical Properties Impacting Oral Absorption of Drugs" Biopharmaceutics Applications in Drug Development, Chapter 2, Springer, 2008, pp. 26-46.
Study protocol of trial NCT01037582 of Dec. 2009, 7 pages.
U.S. Appl. No. 17/628,459, filed Jan. 19, 2022, 56 pages.
Excerpt from Wikipedia titled "Beagle" dated Apr. 30, 2014.
Tokuriki et al., "Stability effects of mutations and protein evolvability", Current Opinion in Structural Biology, Oct. 2009, vol. 19, No. 5, pp. 596-604.

(56) References Cited

OTHER PUBLICATIONS

Victor et al., "Chapter 18: Eligen® Technology for Oral Delivery of Proteins and Peptides", Mucosal Delivery of Biopharmaceuticals, 2014, pp. 407-422.

Steinert et al., "Orally Administered Glucagon-Like Peptide-1 Affects Glucose Homeostasis Following an Oral Glucose Tolerance Test in Healthy Male Subjects", Clinical Pharmacology and Therapeutics, 2009, vol. 86, No. 6, pp. 644-650.

Khodzhava M.V., "Influence of Glidants on the Quality of Tablet Drugs", Pharmacy, 2011, vol. 7, pp. 31-33.

Setkina et al., "Biopharmaceutical Aspects of Drug Technology and Ways to Modify Bioavailability", VSMU Bulletin, 2014, vol. 13, No. 4, pp. 162-172.

Verbeeck et al., "Generic substitution: The use of medicinal products containing different salts and implications for safety and efficacy", European Journal of Pharmaceutical Sciences, May 2006, vol. 28, No. 1-2, pp. 1-6.

Galstyan et al., "Evolution of glucagon-like peptide-1 receptor agonists in type 2 diabetes therapy", Diabetes, 2017, vol. 20, No. 4, pp. 286-298.

Moon et al., "The development of non-peptide glucagon-like peptide-1 receptor agonist for the treatment of type 2 diabetes", Arch Pharm Res, Jul. 2011, vol. 34, No. 7, pp. 1041-1043.

Melanie Davies et al., "Effect of Oral Semaglutide Compared With Placebo and Subcutaneous Semaglutide on Glycemic Control in Patients With Type 2 Diabetes: A Randomized Clinical Trial," JAMA The Journal of The American Medical Association, 2017, vol. 318, No. 15, p. 1460.

Steinert et al., "Oral Administration of Glucagon-Like Peptide 1 or Peptide YY 3-36 Affects Food Intake in Healthy Male Subjects," Am J Clin Nutr, Oct. 2010, vol. 92, No. 4, pp. 810-817.

He Xiaorong et al., Mechanistic Study of the Effect of Roller Compaction and Lubricant on Tablet Mechanical Strength, Journal: Journal of Pharmaceutical Sciences, Year: 2007, vol. 96, No. 5, pp. 1342-1355.

Mollan Jr. Matthew J. et al., The effects of lubrication on the compaction and post-compaction properties of directly compressible maltodextrins, Journal: International Journal of Pharmaceutics, Year: 1996, vol. 144, Issue 1, pp. 1-9.

Rowe Raymond C et al., Book: Handbook of Pharmaceutical Excipients, Title: Acesulfame Potassium, Edition—5th, Year: 2006, Complete book.

Steinert R E et al., Orally Administered Glucagon-Like Peptide-1 Affects Glucose Homeostasis Following an Oral Glucose Tolerance Test in Healthy Male Subjects, Journal: Clinical Pharmacology and Therapeutics, Year: 2009, vol. 36, No. 6, pp. 644-650.

Von Eggelkraut-Gottanka Stephan G. et al., Roller Compaction and Tabletting of St. John's Wort Plant Dry Extract Using a Gap Width and Force Controlled Roller; Compactor. II. Study of Roller Compaction Variables on Granule and Tablet Properties by a 33 Factorial Design, Journal: Pharmaceutical Development and Technology, Year: 2002, vol. 7, No. 4, pp. 447-455.

Beglinger C et al., Clinical Pharmacology and Therapeutics,"Pharmacokinetics and Pharmacodynamic Effects of Oral GLP-1 and PYY3-36: A Proof-of-Concept Study in Healthy Subjects"., 2008, vol. 84, No. 4, pp. 468-474.

Steinert RE et al, American Journal of Clinical Nutrition, "Oral Administration of Glucagon-Like Peptide 1 or Peptide YY 3-36 Affects Food Intake in Healthy Male Subjects", 2010, vol. 92, pp. 810-817.

Beglinger C et al., Pharmacokinetics and Pharmacodynamic Effects of Oral GLP-1 and PYY3-36: A Proof-of-concept Study in Healthy Subjects, Journal: Clinical Pharmacology & Therapeutics, Nature Publishing Group, Year: 2008. vol. 84, No. 4, pp. 468-474.

Leonard Thomas W et al., Promoting absorption of drugs in humans using medium-chain fatty acid-based solid dosage forms:GIPET™, Journal: Expert Opinion Drug Delivery, Year: 2006, vol. 3(5), pp. 685-692.

Maher Sam et al., Overcoming poor permeability: translating permeation enhancers for oral peptide delivery, Journal: Drug Discovery Today: Technologies, Year: 2011, vol. 9, No. 2, pp. e113-e119.

Maher Sam et al., Safety and efficacy of sodium caprate in promoting oral drug absorption: from in vitro to the clinic, Journal: Advanced Drug Delivery Reviews, Year: 2009, vol. 61, pp. 1427-1449.

Michel Marre et al., GLP-1 receptor agonists today, Journal: Diabetes Research; and Clinical Practice, Year: 2011, vol. 93, No. 3, pp. 317-327.

Walsch Edwin G et al., Oral delivery of macromolecules: rationale underpinning Gastrointestinal Permeation Enhancement Technology (GIPET®), Journal: Therapeutic Delivery, Year: 2011, vol. 2, No. 12, pp. 1595-1610. OTH.

Makoto Otsuka, Chemoinformetrical evaluation of granule and tablet properties of pharmaceutical preparations by near-infrared spectroscopy, "Chemometrics and Intelligent Laboratory Systems" Year 2006, vol. 82, No. 1-2, pp. 109-114.

Shah R. B et al. Process Analytical Technology: Chemometric Analysis of Raman and Near Infra-red Spectroscopic Data for Predicting Physical Properties of Extended Release Matrix Tablets, "Journal of Pharmaceutical Sciences" Year 2007, vol. 96, No. 5, pp. 1356-1365.

Aenugu H.P.R et al. Near Infra Red Spectroscopy—An Overview, "International Journal of ChemTech Research" Year 2011, vol. 3, No. 2, pp. 825-836.

Donoso M et al. Prediction of Tablet Hardness and Porosity Using Near-Infrared Diffuse Reflectance Spectroscopy as a Nondestructive Method, "Pharmaceutical Development and Technology" Year 2003, vol. 8, No. 4, pp. 357-366.

Jeckel et al. Importance of particle size knowledge for tablet porosity determination by NIRS, "Tablet Tech Seminar, FMC Biopolymer" Year 2007, retrieved from the Internet: URL:http://www.pharmtech.uni-bonn.de/forschung/arbeitskreis-porf-steffens/download-16, the whole document.

Remington, The Science and Practice of Pharmacy, 22nd Edition, 2012.

Felix Kratz "A Clinical Update of Using Albumin as a Drug Vehicle—A Commentary" Journal of Controlled Release 2014 vol. 190 pp. 331-336.

Rivera et al. Oral Delivery of Heparin in Combination with Sodium N-[8-(2-Hydroxybenzoyl)amino]caprylate: Pharmacological Considerations. Pharmaceutical Research 1997 vol. 14 No. 12 pp. 1830-1834.

Su Young Chae et al. "Preparation, Characterization and Application of Biotinylated and Biotin-PEGylated Glucagon-Like Peptide-1 Analogues for Enhanced Oral Delivery." Bioconjugate Chemistry 2008 vol. 19 No. 1 pp. 334-341.

Emisphere Technologies. "Carriers Enhance Drug Delivery" Manufacturing Chemistry 1999 vol. 70 No. 6 pp. 25-26.

Adam W. G. Alani et al., "Mechanistic Understanding of Oral Drug Absorption Enhancement of Cromolyn Sodium by an Amino Acid Derivative," Pharmaceutical Research, 2008, vol. 25, No. 1, pp. 48-54.

Granulation Handbook, Chapter 4. Compression Granulation Method, May 30, 1975, 1st Edition First Press, p. 173-197.

Design and evaluation of formulation for oral administration, Problem arising from industrialization and process scale-up and corresponding solutions, Feb. 10, 1995, p. 264-279.

Bhansali et al., "Historical Overview of Incretin Based Therapies," Supplement to JAPI, 2010, vol. 58, pp. 10-14.

Valentino et al., "Central and Peripheral Molecular Targets for Antiobesity Pharmacotherapy," Clinical Pharmacology and Therapeutics, 2010, vol. 87, No. 6, pp. 652-662.

Bastin et al., "Salt Selection and Optimisation Procedures for Pharmaceutical New Chemical Entities," Org Proc Res & Devt, 2000, vol. 4, pp. 427-435.

Drug Data Report, 2006, vol. 28, p. 933.

Anonymous, "Eligen@ Technology. Summary and Value Proposition", Emisphere, Feb. 24, 2017, pp. 1-10, URL: https://www.emisphere.com/wp-content/uploads/2017/02/Eligen-Technology-Presentation_2.15-Update.pdf, XP055520567.

Keck et al., Moderne Pharmazeutische Technologie, 2009, pp. 8-14.

(56) References Cited

OTHER PUBLICATIONS

Kidron et al., "A Novel Per-Oral Insulin Formulation: Proof of Concept Study in Non-Diabetic Subjects," Diabetic Medicine, 2004, vol. 21, pp. 354-357.
Letter to Sandoz International GmbH regarding English translation of claim of patent JP4585037, dated Aug. 29, 2018.
Mullins, "Statistics for the Quality Control Chemistry Laboratory," 2003, Chapter I, pp. 10-17.
SNAC, Synchem, http://www.synchem.de/product/snac, accessed Aug. 16, 2018.
Valentino et al., "Current Trends in Targeting the Hormonal Regulation of Appetite and Energy Balance to Treat Obesity," Expert Rev Endocrinol Metab, 2010, vol. 5, pp. 765-783.
WHO Drug Information, "International Nonproprietary Names for Pharmaceutical Substances," 2009, vol. 23, No. 2, p. 164.
U.S. Appl. No. 61/425,087, filed Dec. 20, 2010.
EP Application No. 10195285.1, filed Dec. 16, 2010.
Wang et al., "Non-peptidic glucose-like peptide-1 receptor agonists: aftermath of serendipitous discovery," Acta Pharmacol. Sinica, 2010, vol. 31, pp. 1026-1030.
Baynes, Kevin C. R., "The evolving world of GLP-1 agonist therapies for type 2 diabetes" Therapeutic Advances in Endocrinology and Metabolism, 2010,, vol. 1, No. 2, pp. 61-67.
Buckley, Stephen T. et al., "Transcellular stomach absorption of a derivatized glucagon-like peptide-1 receptor agonist" Science Translational Medicine, Nov. 14, 2018, vol. 10, pp. 1-14.
Christensen, Mikkel et al., "Once-Weekly GLP-1 Agonists: How Do They Differ from Exenatide and Liraglutide?" Curr Diab Rep, 2010, vol. 10, pp. 124-132.
Davies, Melanie et al., "Effect of Oral Semaglutide Compared with Placebo and Subcutaneous Semaglutide on Glycemic Control in Patients with Type 2 Diabetes" JAMA, 2017, vol. 318, pp. 1460-1470.
Declaration by the Inventor, Flemming S. Nielsen, dated Feb. 11, 2019.
EMEA Assessment Report EMEA/379172/2009 for Victoza (liraglutide), 2009.
Goldberg, Michael et al., "Challenges for the Oral Delivery of Macromolecules" Nature Reviews Drug Discovery, 2003, vol. 2, pp. 289-294.

* cited by examiner

A

B

C

SOLID COMPOSITIONS COMPRISING A GLP-1 AGONIST AND A SALT OF N-(8-(2-HYDROXYBENZOYL)AMINO)CAPRYLIC ACID

CROSS-REFERENCE TO RELATED APPLICATIONS

This application is a continuation of U.S. application Ser. No. 16/570,723, filed Sep. 13, 2019, which is continuation of an International Application No. PCT/EP2019/052487 (WO 2019/149880), filed Feb. 1, 2019, which claims priority to European Patent Application No. 18154913.0, filed Feb. 2, 2018; the contents of which are incorporated herein by reference.

TECHNICAL FIELD OF THE INVENTION

The present invention relates to solid compositions comprising a GLP-1 agonist and a salt of N-(8-(2-hydroxybenzoyl)amino)caprylic acid, their method of preparation and their use in medicine.

INCORPORATION-BY-REFERENCE OF THE SEQUENCE LISTING

The instant application contains a Sequence Listing which has been submitted in XML format via the USPTO patent electronic filing system and is hereby incorporated by reference in its entirety. Said XML file, created on Oct. 25, 2023, is named 170097US02. xml and is 11 kilobytes in size.

BACKGROUND

Human GLP-1 and analogues thereof have a low oral bioavailability. Exposure and bioavailability of human GLP-1 and analogues thereof is very low following oral administration. Human GLP-1 (and analogues thereof) can thus only be detected in plasma after oral administration if formulated with certain absorption enhancers in a specific amount.

Steinert et al. (Am J Clin Nutr, October 2010; 92: 810-817) discloses oral administration of a tablet comprising GLP-1(7-36)amide and 150 mg sodium N-(8-(2-hydroxybenzoyl)amino)caprylate (SNAG).

WO 2010/020978 discloses an oral pharmaceutical composition comprising a protein and N-(8-[2-hydroxybenzoyl)amino)caprylate (SNAG). Patent applications disclosing oral dosage forms of GLP-1 analogues containing a salt of N-(8-(2-hydroxybenzoyl)-amino)caprylate include WO2012/080471, WO2013/189988, WO2013/139694, WO2013/139695 and WO2014/177683.

Despite these findings there is still room for a further optimized pharmaceutical composition for oral administration of a GLP-1 agonist such as a GLP-1 analogue comprising a substituent.

SUMMARY

The present invention relates to a composition comprising a GLP-1 agonist and an absorption enhancer or delivery agent. The composition according to the invention in an embodiment includes a very high content of the delivery agent and a minimal content of further excipients as described herein below. The provided compositions display an accelerated absorption, enabling fast and efficient uptake of the active pharmaceutical ingredient.

Oral administration of therapeutic peptides is challenging due to the rapid degradation of such peptides in the gastrointestinal system. Described herein are pharmaceutical compositions providing accelerate absorption of the GLP-1 agonist within 15-30 minutes after administration and thereby improved exposure of the GLP-1 agonist by oral administration. The inventors have surprisingly found that the plasma exposure of GLP-1 agonists increases when compositions are prepared with a very high content of the absorption enhancer and a minimal content of any further excipients.

In an aspect the invention relates to a composition wherein the weight ratio of the delivery agent relative to the total composition, or in particular, relative to the other excipients of the composition, is very high.

In one embodiment, the invention relates to a pharmaceutical composition comprising a GLP-1 agonist, a delivery agent and/or absorption enhancer such as SNAC, wherein the delivery agent/absorption enhancer constitutes at least 90%, such as at least 95% w/w of the excipients of the composition.

In one embodiment, the invention relates to a pharmaceutical composition comprising a GLP-1 agonist, a delivery agent and/or absorption enhancer such as SNAC, wherein the delivery agent/absorption enhancer constitutes at least 90% w/w of the composition.

In additional embodiments, the composition further includes a lubricant.

In an aspect the invention relates to a method of preparing a pharmaceutical composition as described herein such as a method comprising the steps of;
  a) granulating a mixture comprising the delivery agent, the GLP-1 agonist and optionally a lubricant and
  b) compressing the granulate obtained in step a) into tablets and optionally adding further lubricant to the granulate prior to compression.

In a further aspect the invention relates to a composition or a granule as defined herein for use in medicine, such as for treatment of diabetes or obesity, wherein said composition is administered orally.

In a further aspect the invention relates to a method of treating diabetes or obesity comprising administering the composition as defined herein to a patient in need thereof, wherein said composition is a tablet and is administered orally.

DESCRIPTION

Figure 1:
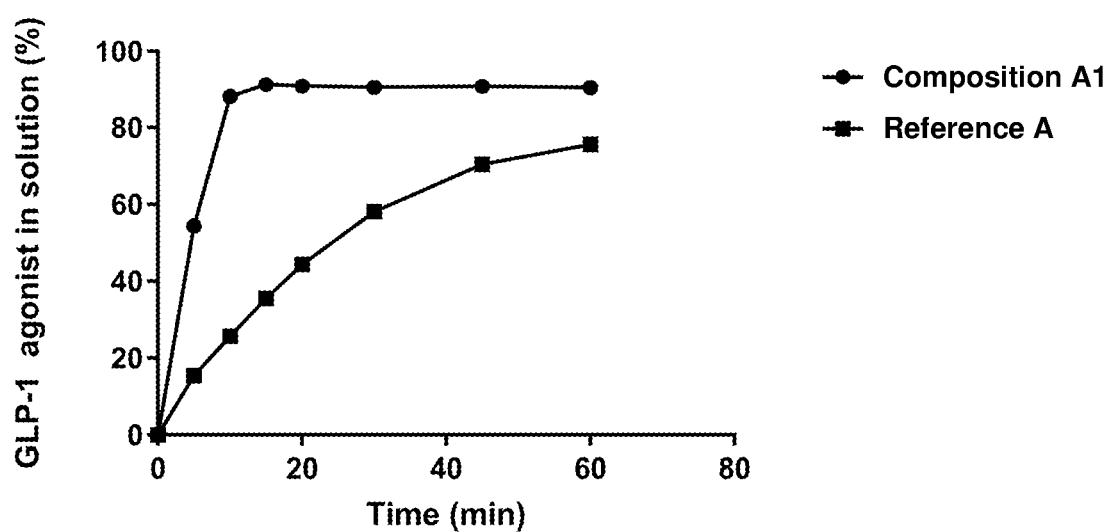
FIG. 1 shows fast dissolution of A1 compared to Reference A.

An aspect of the invention relates to a composition comprising a GLP-1 agonist and an absorption enhancer or delivery agent. The composition may be in the form suitable for oral administration, such as a tablet, sachet or capsule. In an embodiment the composition is an oral composition, or a pharmaceutical composition, such as an oral pharmaceutical composition.

The composition according to the invention in an embodiment includes a high content of the delivery agent and a minimal content of further excipients as described herein below. The provided compositions display an accelerated dissolution and absorption, enabling fast and efficient uptake of the active pharmaceutical ingredient.

GLP-1

The term "GLP-1 agonist" as used herein refers to a compound, which fully or partially activates the human GLP-1 receptor. The term is thus equal to the term "GLP-1 receptor agonist" used in other documents. The term GLP-1 agonist as well as the specific GLP-1 agonists described herein are meant to encompass also salt forms hereof.

It follows that the GLP-1 agonist should display "GLP-1 activity" which refers to the ability of the compound, i.e. a GLP-1 analogue or a compound comprising a GLP-1 analogue, to bind to the GLP-1 receptor and initiate a signal transduction pathway resulting in insulinotropic action or other physiological effects as is known in the art. In some embodiments the "GLP-1 agonist" binds to a GLP-1 receptor, e.g., with an affinity constant ($K_D$) or activate the receptor with a potency ($EC_{50}$) of below 1 μM, e.g. below 100 nM as measured by methods known in the art (see e.g. WO 98/08871) and exhibits insulinotropic activity, where insulinotropic activity may be measured in vivo or in vitro assays known to those of ordinary skill in the art. For example, the GLP-1 agonist may be administered to an animal with increased blood glucose (e.g. obtained using an Intravenous Glucose Tolerance Test (IVGTT). A person skilled in the art will be able to determine a suitable glucose dosage and a suitable blood sampling regime, e.g. depending on the species of the animal, for the IVGTT) and measure the plasma insulin concentration over time.

Suitable assays have been described in such as WO2015/155151.

The term half maximal effective concentration ($EC_{50}$) generally refers to the concentration which induces a response halfway between the baseline and maximum, by reference to the dose response curve. $EC_{50}$ is used as a measure of the potency of a compound and represents the concentration where 50% of its maximal effect is observed. Due to the albumin binding effects of GLP-1 agonists comprising a substituent as described herein, it is important to pay attention to if the assay includes human serum albumin or not.

The in vitro potency of the GLP-1 agonist may be determined as described in 2015/155151, example 29 (without HSA) and the EC50 determined. The lower the $EC_{50}$ value, the better the potency. In one embodiment the potency (EC50) as determined (without HSA) is 5-1000 pM, such as 10-750 pM, 10-500 pM or 10-200 pM. In one embodiment the EC50 (without HSA) is at most 500 pM, such as at most 300 pM, such as at most 200 pM.

In one embodiment the EC50 (without HSA) is comparable to human GLP-1(7-37).

In one embodiment the EC50 (without HSA) is at most 50 pM. In a further such embodiment the EC50 is at most 40 pM, such as at most 30 pM such as at most 20 pM, such as at most 10 pM. In one embodiment the EC50 is around 10 pM.

If desired, the fold variation in relation to a known GLP-1 receptor agonist may be calculated as EC50(test analogue)/EC50(known analogue), and if this ratio is such as 0.5-1.5, or 0.8-1.2 the potencies are considered to be equivalent.

In one embodiment the potency, EC50 (without HSA), is equivalent to the potency of liraglutide.

In one embodiment the potency, EC50 (without HSA), is equivalent to the potency of semaglutide.

In one embodiment the potency, EC50 (without HSA), is equivalent to the potency of Compound B.

In one embodiment the potency, EC50 (without HSA), is equivalent to the potency of Compound C.

In some embodiments the GLP-1 agonist is a GLP-1 analogue, optionally comprising one substituent. The term "analogue" as used herein referring to a GLP-1 peptide (hereafter "peptide") means a peptide wherein at least one amino acid residue of the peptide has been substituted with another amino acid residue and/or wherein at least one amino acid residue has been deleted from the peptide and/or wherein at least one amino acid residue has been added to the peptide and/or wherein at least one amino acid residue of the peptide has been modified. Such addition or deletion of amino acid residues may take place at the N-terminal of the peptide and/or at the C-terminal of the peptide. In some embodiments a simple nomenclature is used to describe the GLP-1 agonist, e.g., [Aib8] GLP-1(7-37) designates an analogue of GLP-1(7-37) wherein the naturally occurring Ala in position 8 has been substituted with Aib. In some embodiments the GLP-1 agonist comprises a maximum of twelve, such as a maximum of 10, 8 or 6, amino acids which have been altered, e.g., by substitution, deletion, insertion and/or modification, compared to e.g. GLP-1(7-37). In some embodiments the analogue comprises up to 10 substitutions, deletions, additions and/or insertions, such as up to 9 substitutions, deletions, additions and/or insertions, up to 8 substitutions, deletions, additions and/or insertions, up to 7 substitutions, deletions, additions and/or insertions, up to 6 substitutions, deletions, additions and/or insertions, up to 5 substitutions, deletions, additions and/or insertions, up to 4 substitutions, deletions, additions and/or insertions or up to 3 substitutions, deletions, additions and/or insertions, compared to e.g. GLP-1(7-37). Unless otherwise stated the GLP-1 comprises only L-amino acids.

In some embodiments the term "GLP-1 analogue" or "analogue of GLP-1" as used herein refers to a peptide, or a compound, which is a variant of the human Glucagon-Like Peptide-1 (GLP-1(7-37)). GLP-1(7-37) has the sequence HAEGTFTSDV SSYLEGQAAKEFIAWLVKGRG (SEQ ID NO: 1). In some embodiments the term "variant" refers to a compound which comprises one or more amino acid substitutions, deletions, additions and/or insertions.

In one embodiment the GLP-1 agonist exhibits at least 60%, 65%, 70%, 80% or 90% sequence identity to GLP-1 (7-37) over the entire length of GLP-1(7-37). As an example of a method for determination of sequence identity between two analogues the two peptides [Aib8]GLP-1(7-37) and GLP-1(7-37) are aligned. The sequence identity of [Aib8] GLP-1(7-37) relative to GLP-1(7-37) is given by the number of aligned identical residues minus the number of different residues divided by the total number of residues in GLP-1 (7-37). Accordingly, in said example the sequence identity is (31-1)/31.

In one embodiment the C-terminal of the GLP-1 agonist is an amide.

In some embodiments the GLP-1 agonist is GLP-1(7-37) or GLP-1(7-36)amide. In some embodiments the GLP-1 agonist is exendin-4, the sequence of which is HGEGTFITSDLSKQMEEEAVRLFIEWLKNGGPSSGAPPPS (SEQ ID NO: 2).

In order to prolong the effect of the GLP-1 agonist it is preferred that the GLP-1 agonist have an extended half-life. The half-life can be determined by method known in the art and in an appropriate model, such as in Male Sprague Dawley rats or minipigs as described in WO2012/140117.

In one embodiment the GLP-1 agonist according to the invention has a half-life above 24 hours in minipig. In one embodiment the GLP-1 agonist according to the invention has a half-life above 30 hours, such as above 36 hours, such as above 42 hours, such as above 48 hours, such as above 54 hours or such as above 60 hours in minipig.

In some embodiments the GLP-1 agonist comprises one substituent which is covalently attached to the peptide. In some embodiments the substituent comprises a fatty acid or a fatty diacid. In some embodiments the substituent comprises a C16, C18 or C20 fatty acid. In some embodiments the substituent comprises a C16, C18 or C20 fatty diacid.

In some embodiments the substituent comprises formula (X)

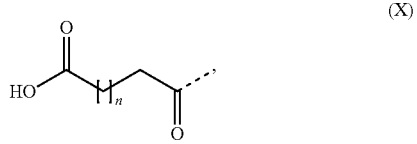

wherein n is at least 13, such as n is 13, 14, 15, 16, 17, 18 or 19. In some embodiments the substituent comprises formula (X), wherein n is in the range of 13 to 19, such as in the range of 13 to 17. In some embodiments the substituent comprises formula (X), wherein n is 13, 15 or 17. In some embodiments the substituent comprises formula (X), wherein n is 13. In some embodiments the substituent comprises formula (X), wherein n is 15. In some embodiments the substituent comprises formula (X), wherein n is 17.

In some embodiments the substituent comprises formula (XIa)   HOOC—(C$_6$H$_4$)—O—(CH$_2$)$_m$—CO—*   (XIa), wherein m is an integer in the range of 6-14.

In some embodiments the substituent comprises formula (XIb)

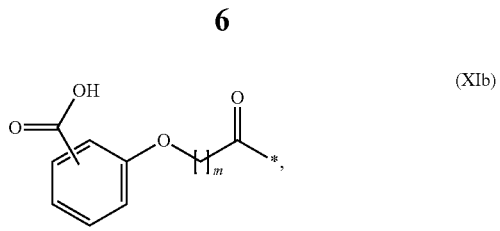

wherein the carboxy group is in position 2, 3 or 4 of the (C$_6$H$_4$) group and wherein m is an integer in the range of 8-11.

In some embodiments the substituent comprises formula (XIa) or formula (XIb), wherein m is in the range of 6 to 14, such as in the range of 8 to 11. In some embodiments the substituent comprises formula (XIa) or formula (XIb), wherein m is 8, 10 or 12. In some embodiments the substituent comprises formula (XIa) or formula (XIb), wherein m is 9. In some embodiments the substituent comprises formula (XIa) or formula (XIb), wherein m is 11.

In some embodiments the substituent comprises one or more 8-amino-3,6-dioxaoctanoic acid (OEG), such as two OEG.

In some embodiments the substituent is [2-(2-{2-[2-(2-{2-[(S)-4-carboxy-4-(17-carboxyheptadecanoylamino) butyrylamino]ethoxy}ethoxy)acetylamino] ethoxy}ethoxy) acetyl].

In some embodiments the substituent is [2-(2-{2-[2-(2-{2-[(S)-4-carboxy-4-({trans-4-[(19-carboxynonadecanoylamino)methyl]cyclohexanecarbonyl} amino)butyrylamino] ethoxy}ethoxy)acetylamino]ethoxy}ethoxy)acetyl].

In some embodiments the GLP-1 agonist is semaglutide, also known as N-epsilon26-[2-(2-{2-[2-(2-{2-[(S)-4-carboxy-4-(17-carboxyheptadecanoylamino) butyrylamino] ethoxy}ethoxy)acetylamino]ethoxy}ethoxy)acetyl][Aib8, Arg34]GLP-1(7-37) (SEQ ID NO: 4) which may be prepared as described in WO2006/097537, Example 4 with the following structure:

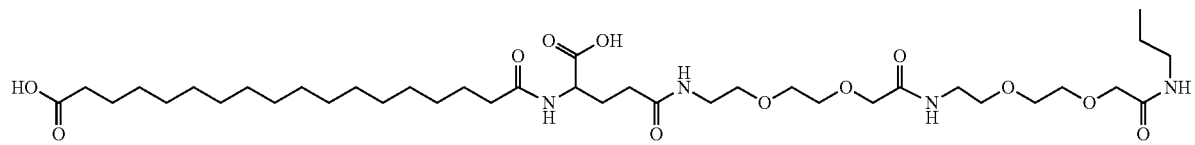

In one embodiment the GLP-1 agonist is GLP-1 agonist B, which is diacylated [Aib8,Arg34,Lys37]GLP-1(7-37) (SEQ ID NO. 5) as shown in Example 2 of WO2011/080103 and named N$^{\varepsilon26}${2-[2-(2-{2-[2-{2{(S)-4-Carboxy-4-[10-(4-carboxyphenoxy)decanoylamino]butyrylamino}-ethoxy) ethoxy]acetylamino}ethoxy)ethoxy]acetyl}, N$^{\varepsilon37}$-{2-[2-(2-{2-[2-(2-{(S)-4-carboxy-4-[10-(4-carboxyphenoxy) decanoylamino]butyrylamino}ethoxy)ethoxy] acetylamino}ethoxy)ethoxy]-acetyl}-[Aib$^8$,Arg$^{34}$,Lys$^{37}$] GLP-1(7-37)-peptide with the following structure.

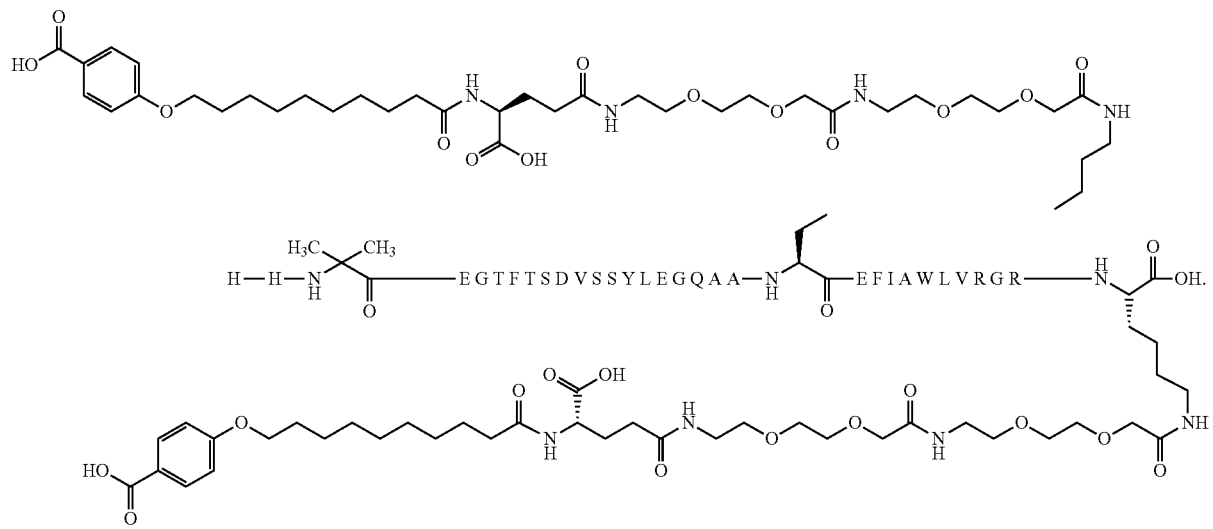

In one embodiment the GLP-1 agonist is GLP-1 agonist C which is Diacylated [Aib8,Glu22,Arg26,Lys27,Glu30, Arg34,Lys36]-GLP-1-(7-37)-peptidyl-Glu-Gly (SEQ ID NO. 6) as shown in Example 31 of WO2012/140117 and named $N^{\epsilon27}$-[2-[2-[2-[[2-[2-[2-[[(4S)-4-carboxy-4-[10-(4-carboxyphenoxy)decanoylamino]butanoyl]amino]ethoxy]ethoxy]acetyl]amino]ethoxy]ethoxy]-acetyl], $N^{\epsilon36}$-[2-[2-[2-[[2-[2-[2-[[(4S)-4-carboxy-4-[10-(4-carboxyphenoxy)decanoylamino]-butanoyl]amino]ethoxy]ethoxy]acetyl]amino]ethoxy]ethoxy]acetyl]-[Aib8,Glu22,Arg26,Lys27,Glu30,Arg34,Lys36]-GLP-1-(7-37)-peptidyl-Glu-Gly with the following structure 19175, WO96/29342, WO98/08871, WO99/43707, WO99/43706, WO99/43341, WO99/43708, WO2005/027978, WO2005/058954, WO2005/058958, WO2006/005667, WO2006/037810, WO2006/037811, WO2006/097537, WO2006/097538, WO2008/023050, WO2009/030738, WO2009/030771 and WO2009/030774.

In some embodiments the GLP-1 agonist is selected from the group consisting of N-epsilon37-{2-[2-(2-{2-[2-((R)-3-carboxy-3-{[1-(19-carboxynonadecanoyl) piperidine-4-carbonyl]amino}propionylamino)ethoxy]ethoxy}acetylamino)ethoxy]ethoxy}acetyl [desaminoHis7,Glu22,Arg26,Arg34,Lys37]GLP-1(7-37)amide; N-epsilon26{2-[2-(2-{2-[2-((R)-

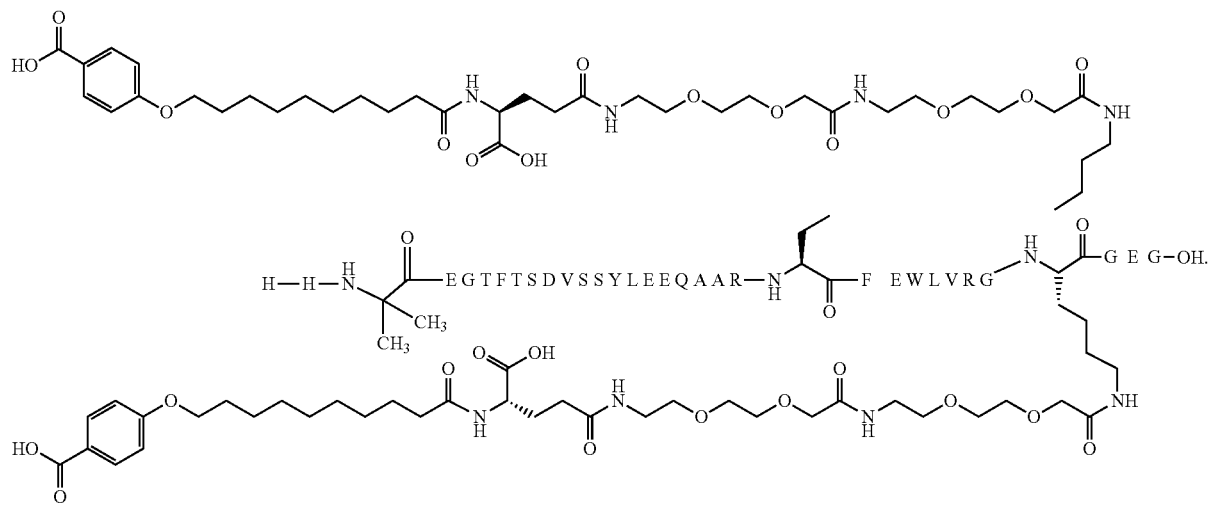

In general the term GLP-1 agonist is meant to encompass the GLP-1 agonist and any pharmaceutically acceptable salt, amide, or ester thereof. In some embodiments the composition comprises the GLP-1 agonist or a pharmaceutically acceptable salt, amide, or ester thereof. In some embodiments the composition comprises the GLP-1 agonist and one or more pharmaceutically acceptable counter ions.

In some embodiments the GLP-1 agonist is selected from one or more of the GLP-1 agonists mentioned in WO93/

3-carboxy-3-{[1-(19-carboxynonadecanoyl) piperidine-4-carbonyl]amino} propionylamino)ethoxy] ethoxy}acetylamino)ethoxy] ethoxy}acetyl [desaminoHis7,Arg34] GLP-1-(7-37); N-epsilon37{2-[2-(2-{2-[2-((S)-3-carboxy-3-{[1-(19-carboxy-nonadecanoyl) piperidine-4-carbonyl]amino}propionylamino)ethoxy] ethoxy}acetylamino)ethoxy] ethoxy}acetyl[Aib8,Glu22,Arg26,Arg34,Lys37]GLP-1-(7-37)amide; N-epsilon37-[2-(2-[2-(2-[2-(2-((R)-3-[1-(17-carboxyheptadecanoyl)piperidin-4-ylcarbonylamino]3-carboxypropionylamino)ethoxy)ethoxy] acetylamino)ethoxy} ethoxy)acetyl][DesaminoHis7,Glu22 Arg26,Arg 34,Phe(m-CF3)28]GLP-1-(7-37)amide; N-epsilon26-[(S)-4-carboxy-4-({trans-4-[(19-carboxynonadecanoylamino)methyl] cyclohexanecarbonyl}amino)butyryl] [Aib8,Arg34]GLP-1-(7-37); N-epsilon26-{4-[(S)-4-carboxy-4-({trans-4-[(19-carboxynonadecanoylamino) methyl]cyclohexanecarbonyl} amino)butyrylamino]butyryl}[Aib8,Arg34]GLP-1-(7-37); N-epsilon26-[2-(2-{2-[(S)-4-carboxy-4-({trans-4-[(19-carboxy- nonadecanoylamino) methyl]cyclohexanecarbonyl} amino) butyrylamino]ethoxy}ethoxy)acetyl][Aib8,Arg34]GLP-1-(7-37); N-epsilon26-[2-(2-{2-[2-(2-{2-[(S)-4-carboxy-4-({trans-4-[(19-carboxy-nonadecanoylamino)methyl] cyclohexanecarbonyl}amino)butyrylamino]ethoxy}ethoxy) acetylamino]ethoxy}ethoxy) acetyl][Aib8,Arg34]GLP-1-(7-37)amide; N-epsilon37-[2-(2-{2-[2-(2-{2-[(S)-4-carboxy-4-({trans-4-[(19-carboxy- nonadecanoylamino) methyl]cyclohexanecarbonyl}amino) butyrylamino] ethoxy}ethoxy)acetylamino]ethoxy}ethoxy)acetyl][Aib8, Glu22,Arg26, Arg34,Lys37]GLP-1-(7-37)amide; N-epsilon37-[2-(2-{2-[2-(2-{2-[(S)-4-carboxy-4-({trans-4-[(19-carboxy- nonadecanoylamino)methyl] cyclohexanecarbonyl}amino) butyrylamino] ethoxy}ethoxy)acetylamino]ethoxy}ethoxy)acetyl][DesaminoHis7,Glu22, Arg26,Arg34,Lys37]GLP-1-(7-37)amide; N-epsilon37-[2-(2-{2-[2-(2-{2-[(S)-4-carboxy-4-({4-[(trans-19-carboxy- nonadecanoylamino)methyl] cyclohexanecarbonyl}amino) butyrylamino]ethoxy}ethoxy) acetylamino]ethoxy}ethoxy)acetyl][DesaminoHis7,Arg26, Arg34,Lys37]GLP-1-(7-37)amide; N-epsilon37-[2-(2-{2-[2-(2-{2-[(S)-4-carboxy-4-({trans-4-[(19-carboxy-nonadecanoylamino)methyl]cyclohexanecarbonyl}amino) butyrylamino]ethoxy}ethoxy)acetylamino]ethoxy}ethoxy) acetyl][DesaminoHis7,Glu22,Arg26,Arg34,Lys37]GLP-1-(7-37); N-epsilon26[2-(2-{2-[2-(2-{2-[(S)-4-carboxy-4-({4-[(19-carboxy-nonadecanoylamino)methyl] cyclohexanecarbonyl}amino)butyrylamino] ethoxy}ethoxy) acetylamino]ethoxy}ethoxy)acetyl[Aib8,Lys 26]GLP-1-(7-37)amide; N-epsilon26 [2-(2-[2-(2-[2-(2-((S)-2-[trans-4-((9-carboxynonadecanoylamino] methyl) cyclohexylcarbonylamino]-4-carboxybutanoylamino)ethoxy)ethoxy] acetylamino) ethoxy]ethoxy)acetyl][Aib8,Lys26]GLP-1 (7-37)amide; N-epsilon37-[2-(2-{2-[2-(2-{2-[(S)-4-carboxy-4-({trans-4-[(19-carboxy-nonadecanoylamino) methyl]cyclohexane-carbonyl} amino)butyrylamino] ethoxy}ethoxy)acetylamino]ethoxy}ethoxy)acetyl] [DesaminoHis7,Arg26,Arg34,Lys37]GLP-1-(7-37); N-epsilon37-[2-(2-{2-[2-(2-{2-[(S)-4-carboxy-4-({trans-4-[(19-carboxy-nonadecanoylamino)methyl]cyclohexanecarbonyl} amino)butyrylamino]ethoxy}ethoxy)acetylamino] ethoxy}ethoxy)acetyl][DesaminoHis7,Glu22, Arg26,Glu30, Arg34,Lys37]GLP-1-(7-37); N-epsilon26-[2-(2-{2-[(S)-4-carboxy-4-((S)-4-carboxy-4-{4-[4-(16-(1H-tetrazol-5-yl)-hexadecanoylsulfamoyl)butyrylamino]-butyrylamino}butyrylamino) butyrylamino]ethoxy} ethoxy)acetyl][Aib8,Arg34]GLP-1-(7-37); N-epsilon26-[2-(2-{2-[(S)-4-carboxy-4-((S)-4-carboxy-4-{12-[4-(16-(1H-tetrazol-5-yl)hexadecanoyl-sulfamoyl)butyrylamino] dodecanoylamino}butyrylamino) butyrylamino] ethoxy}ethoxy)acetyl][Aib8,Arg34]GLP-1-(7-37); N-epsilon26-[2-(2-{2-[(S)-4-carboxy-4-((S)-4-carboxy-4-{6-[4-(16-(1H-tetrazol-5-yl)hexadecanoyl-sulfamoyl)butyrylamino]hexanoylamino} butyrylamino)butyrylamino] ethoxy}ethoxy) acetyl[Aib8,Arg34]GLP-1-(7-37); N-epsilon26-[2-(2-{2-[(S)-4-carboxy-4-((S)-4-carboxy-4-{4-[4-(16-(1H- tetrazol-5-yl)hexadecanoylsulfamoyl)butyrylamino] butyrylamino}butyrylamino)butyrylamino] ethoxy}ethoxy)acetyl][Aib8,Arg34]GLP-1-(7-34); N-epsilon26-[2-(2-{2-[(S)-4-carboxy-4-((S)-4-carboxy-4-{12-[4-(16-(1H-tetrazol-5-yl)hexadecanoylsulfamoyl)butyrylamino]-dodecanoylamino}butyrylamino) butyrylamino] ethoxy}ethoxy)acetyl][Aib8,Arg34]GLP-1-(7-34); N-epsilon26-[2-(2-{2-[(S)-4-carboxy-4-((S)-4-carboxy-4-{6-[4-(16-(1H-tetrazol-5-yl)hexadecanoylsulfamoyl) butyrylamino]hexanoylamino}butyrylamino) butyrylamino]ethoxy}ethoxy)acetyl [Aib8,Arg34]GLP-1-(7-34); N-epsilon26-[2-(2-{12-[(S)-4-carboxy-4-((S)-4-carboxy-4-{12-[4-(16-(1H-tetrazol-5-yl)hexadecanoyl-sulfamoyl)butyrylamino]dodecanoylamino} butyrylamino)butyrylamino] ethoxy}ethoxy)acetyl][Aib8,Arg34]GLP-1-(7-35); N-epsilon26-[2-(2-{2-[(S)-4-carboxy-4-((S)-4-carboxy-4-{6-[4-(16-(1H-tetrazol-5-yl)hexadecanoylsulfamoyl)butyrylamino]hexanoylamino} butyrylamino)butyrylamino] ethoxy}ethoxy)acetyl][Aib8,Arg34]GLP-1-(7-35); N-epsilon26-[2-(2-{2-[(S)-4-carboxy-4-((S)-4-carboxy-4-{6-[4-(16-(1H-tetrazol-5-yl)hexadecanoylsulfamoyl)butyrylamino] hexanoylamino}butyrylamino] ethoxy}ethoxy)acetyl][Aib8,Arg34]GLP-1-(7-36)amide; N-epsilon26-[2-(2-{2-[(S)-4-carboxy-4-((S)-4-carboxy-4-{6-[4-(16-(1H-tetrazol-5-yl)hexadecanoylsulfamoyl) butyrylamino]hexanoylamino}butyrylamino) butyrylamino]ethoxy}ethoxy)acetyl][Aib8,Arg34]GLP-1-(7-35); N-epsilon26-[2-(2-{2-[(S)-4-carboxy-4-((S)-4-carboxy-4-{12-[4-(16-(1H-tetrazol-5-yl)hexadecanoyl-sulfamoyl)butyrylamino]dodecanoylamino}butyryl-amino)butyrylamino]ethoxy} ethoxy)acetyl][Aib8,Lys33,Arg34]GLP-1-(7-34); N-epsilon26-[2-(2-{12-[(S)-4-carboxy-4-((S)-4-carboxy-4-{12-[4-(16-(1H-tetrazol-5-yl) hexadecanoylsulfamoyl)butyrylamino] dodecanoylamino}butyrylamino)butyrylamino] ethoxy}ethoxy)acetyl][Aib8,Arg34]GLP-1-(7-36)amide; N-epsilon26-[2-(2-{2-[2-(2-{2-[2-(2-{2-[2-(2-{2-[2-(2-{2-[(S)-4-carboxy-4-((S)-4-carboxy-4-{12-[4-(16-(1H-tetrazol-5-yl)hexadecanoylsulfamoyl) butyrylamino] dodecanoylamino}butyrylamino) butyrylamino] ethoxy}ethoxy) acetylamino]ethoxy}ethoxy)acetylamino] ethoxy}ethoxy)acetylamino]ethoxy}ethoxy)acetylamino] ethoxy}ethoxy)acetylamino]ethoxy}ethoxy)acetyl][Aib8, Lys26,Arg34]GLP-1-(7-36)amide; N-epsilon37-[2-(2-{2-[(S)-4-carboxy-4-((S)-4-carboxy-4-{12-[4-(16-(1H-tetrazol-5-yl)hexadecanoylsulfamoyl)butyrylamino] dodecanoylamino}butyrylamino) butyrylamino] ethoxy}ethoxy)acetyl][Aib8,Glu22,Arg26,Arg34,Lys37] GLP-1-(7-37)amide; N-epsilon37-[2-(2-{2-[(S)-4-carboxy-4-((S)- 4-carboxy-4-{12-[4-(16-(1H-tetrazol-5-yl) hexadecanoylsulfamoyl)butyrylamino] dodecanoylamino}butyrylamino) butyrylamino] ethoxy}ethoxy)acetyl][DesaminoHis7,Glu22,Arg26,Arg34, Lys37]GLP-1-(7-37)amide; N-epsilon37-{2-[2-(2-{2-[2-((R)-3-carboxy- 3-{[1-(19-carboxy-nonadecanoyl) piperidine-4-carbonyl]amino}propionylamino)ethoxy]ethoxy} acetylamino)ethoxy] ethoxy}acetyl [desaminoHis7,Glu22, Arg26,Arg34,Lys37]GLP-1(7-37)amide; N-epsilon37{2-[2-(2-{2-[2-((S)-3-carboxy-3-{[1-(19-carboxynonadecanoyl) piperidine-4-carbonyl]amino} propionylamino) ethoxy] ethoxy}acetylamino)ethoxy] ethoxy} acetyl [Aib8,Glu22, Arg26,Arg34,Lys37]GLP-1-(7-37)amide; N-epsilon37-[2-(2-[2-(2-[2-((R)-3-[1-(17-carboxyhepta-decanoyl) piperidin-4-ylcarbonylamino]3-carboxy-propionylamino) ethoxy]ethoxy] acetylamino) ethoxy] ethoxy)acetyl] [DesaminoHis7,Glu22,Arg26,Arg34,Phe(m-CF3)28] GLP-1-(7-37)amide; N-epsilon37-[2-(2-{2-[2-(2-{2-[(S)-4-carboxy-4-({trans-4-[(19-carboxy-nonadecanoylamino)methyl]

cyclohexanecarbonyl} amino)butyrylamino]ethoxy} ethoxy)acetylamino] ethoxy}ethoxy)acetyl] [Aib8,Glu22, Arg26,Arg34,Lys37]GLP-1-(7-37)amide; N-epsilon37-[2-(2-{2-[2-(2-{2-[(S)-4-carboxy-4-({trans-4-[(19-carboxy-nonadecanoylamino)methyl]cyclohexane-carbonyl} amino} butyrylamino]ethoxy}ethoxy) acetylamino]ethoxy}ethoxy) acetyl] [DesaminoHis7,Glu22,Arg26,Arg34,Lys37]GLP-1-(7-37)amide; N-epsilon37-[2-(2-{2-[2-(2-{2-[(S)-4-carboxy-4-({trans-4-[(19-carboxy-nonadecanoylamino) methyl] cyclohexanecarbonyl}amino)butyrylamino] ethoxy}ethoxy) acetylamino]ethoxy} ethoxy)acetyl] [DesaminoHis7,Glu22,Arg26,Arg34,Lys37]GLP-1-(7-37); N-epsilon37-[2-(2-{2-[2-(2-{2-[(S)-4-carboxy-4-({trans-4-[(19-carboxy-nonadecanoylamino) methyl]cyclohexane-carbonyl}amino)butyrylamino]ethoxy}ethoxy) acetylamino] ethoxy}ethoxy)acetyl] [DesaminoHis7,Glu22, Arg26,Glu30,Arg34,Lys37]GLP-1-(7-37); N-epsilon37-[2-(2-{2-[(S)-4-carboxy-4-((S)-4-carboxy-4-{12-[4-(16-(1H-tetrazol-5-yl)hexadecanoyl-sulfamoyl) butyrylamino] dodecanoylamino} butyrylamino) butyrylamino] ethoxy}ethoxy)acetyl] [Aib8,Glu22,Arg26,Arg34,Lys37] GLP-1-(7-37)amide; N-epsilon37-[2-(2-{2-[(S)-4-carboxy-4-((S)-4-carboxy-4-{12-[4-(16-(1H-tetrazol-5-yl)hexadecanoylsulfamoyl) butyrylamino] dodecanoylamino}butyrylamino) butyrylamino] ethoxy}ethoxy)acetyl] [DesaminoHis7,Glu22,Arg26, Arg34,Lys37]GLP-1-(7-37)amide; N-epsilon37-(3-((2-(2-(2-(2-(2-Hexadecyloxyethoxy)ethoxy)ethoxy) ethoxy) ethoxy)) propionyl)[DesaminoHis7,Glu22,Arg26,Arg34, Lys37]GLP1(7-37)-amide; N-epsilon37-{2-(2-(2-(2-[2-(2-(4-(hexadecanoylamino)-4-carboxybutyryl-amino)ethoxy) ethoxy] acetyl)ethoxy)ethoxy)acetyl)}-[desaminoHis7, Glu22,Arg26,Glu30,Arg34,Lys37] GLP-1-(7-37)amide; N-epsilon37-{2-(2-(2-(2-[2-(2-(4-(hexadecanoylamino)-4-carboxy-butyryl-amino) ethoxy)ethoxy]acetyl)ethoxy) ethoxy) acetyl)[desaminoHis7,Glu22,Arg26,Arg34,Lys37] GLP-1-(7-37)amide; N-epsilon37-(2-(2-(2-(2-(2-(2-(2-(2-(octadecanoyl-amino)ethoxy)ethoxy) acetylamino) ethoxy) ethoxy)acetylamino) ethoxy)ethoxy) acetyl) [desaminoHis7,Glu22,Arg26,Arg34,Lys37] GLP-1-(7-37) amide; N-epsilon37-[4-(16-(1H-Tetrazol-5-yl) hexadecanoylsulfamoyl) butyryl] [DesaminoHis7,Glu22, Arg34,Lys37]GLP-1-(7-37)amide; N-epsilon37-[2-(2-{2-[2-(2-{2-[(S)-4-carboxy-4-(19-carboxynonadecanoylamino) butyrylamino] ethoxy}ethoxy) acetylamino]ethoxy} ethoxy)acetyl] [DesaminoHis7,Glu22, Arg26,Arg34,Lys37]GLP-1-(7-37); N-epsilon37-(2-{2-[2-((S)-4-carboxy-4-{(S)-4-carboxy-4-[(S)-4-carboxy-4-(19-carboxy-nonadecanoylamino)butyrylamino]butyrylamino} butyrylamino)ethoxy]ethoxy} acetyl)[DesaminoHis7, Glu22,Arg26,Arg34,Lys37]GLP-1-(7-37); N-epsilon37-{2-[2-(2-{(S)-4-[(S)-4-(12-{4-[16-(2-tert-Butyl-2H-tetrazol-5-yl)-hexadecanoylsulfamoyl] butyrylamino}dodecanoylamino)-4-carboxybutyrylamino]-4-carboxybutyrylamino} ethoxy)ethoxy]acetyl}[Desamino-His7,Glu22,Arg26,Arg34,Lys37] GLP-1-(7-37); N-epsilon37-[2-(2-[12-[2-(2-{2-[(S)-4-carboxy-4-(17-carboxy-heptadecanoylamino)-butyrylamino]-ethoxy}-ethoxy)-acetylamino]-ethoxy}-ethoxy)-acetyl] [Aib8,Glu22,Arg26, Arg34,Lys37]GLP-1-(7-37); N-alpha37-[2-(2-{2-[2-(2-{2-[(S)-4-carboxy-4-(17-carboxy-heptadecanoylamino)-butyrylamino]-ethoxy}-ethoxy)-acetylamino]-ethoxy}-ethoxy)-acetyl] [Aib8,Glu22,Arg26,Arg34, epsilon-Lys37] GLP-1-(7-37)peptide; N-epsilon37-[2-(2-{2-[2-(2-{2-[(S)-4-carboxy-4-(17-carboxy-heptadecanoylamino)-butyrylamino]-ethoxy}-ethoxy)-acetylamino]-ethoxy}-ethoxy)-acetyl] [desaminoHis7,Glu22,Arg26,Arg34,Lys37] GLP-1-(7-37); N-epsilon36-[2-(2-{2-[2-(2-{2-[(S)-4-carboxy-4-(15-carboxy-pentadecanoylamino)-butyrylamino]-ethoxy}-ethoxy)-acetylamino]-ethoxy}-ethoxy)-acetyl] [desaminoHis7,Glu22,Arg26,Glu30,Arg34,Lys36] GLP-1-(7-37)-Glu-Lys peptide; N-epsilon37-[2-(2-{2-[2-(2-{2-[(S)-4-carboxy-4-({trans-4-[(19-carboxynonadecanoylamino) methyl]cyclohexanecarbonyl}amino)butyryl-amino] ethoxy}ethoxy)acetylamino]ethoxy}ethoxy)acetyl][Aib8, Glu22,Arg26,Arg34,Lys37]GLP-1-(7-37); N-epsilon37-[2-(2-{2-[2-(2-{2-[(S)-4-carboxy-4-(17-carboxy-heptadecanoylamino)-butyrylamino]-ethoxy}-ethoxy)-acetylamino]-ethoxy}-ethoxy)-acetyl][Aib8,Glu22, Arg26, Arg34,Aib35,Lys37]GLP-1-(7-37); N-epsilon37-[(S)-4-carboxy-4-(2-{2-[2-(2-{2-[2-(17-carboxyheptadecanoylamino) ethoxy] ethoxy} acetylamino) ethoxy] ethoxy} acetylamino) butyryl] [Aib8,Glu22,Arg26, 34,Lys37] GLP-1-(7-37); N-epsilon37-[2-(2-[2-(2-[2-(2-[4-(17-carboxyheptadecanoylamino)- 4(S)-carboxybutyry-lamino]ethoxy)ethoxy]acetylamino)ethoxy]ethoxy)acetyl] [ImPr7,Glu22,Arg26,34,Lys37], GLP-1-(7-37); N-epsilon26-{2-[2-(2-{2-[2-(2-{(S)-4-carboxy-4-[10-(4-carboxy-phenoxy) decanoylamino]butyrylamino}ethoxy)ethoxy] acetylamino}ethoxy) ethoxy]acetyl}, N-epsilon37-{2-[2-(2-{2-[2-(2-{(S)-4-carboxy-4-[10-(4-carboxy-phenoxy) decanoylamino] butyrylamino}ethoxy)ethoxy] acetylamino}ethoxy) ethoxy]acetyl}-[Aib8,Arg34,Lys37] GLP-1(7-37)-OH; N-epsilon26 (17-carboxyhepta-decanoyl)-[Aib8,Arg34]GLP-1-(7-37)-peptide; N-epsilon26-(19-carboxynonadecanoyl)-[Aib8,Arg34]GLP-1-(7-37); N-epsilon26-(4-{[N-(2-carboxyethyl)-N-(15-carboxypenta-decanoyl)amino]methyl}benzoyl[Arg34]GLP-1-(7-37); N-epsilon26-[2-(2-[2-(2-[2-(2-[4-(17-carboxyheptade-canoylamino)-4(S)-carboxybutyrylamino]ethoxy)ethoxy] acetylamino) ethoxy]ethoxy)acetyl][Aib8,Arg34]GLP-1-(7-37); N-epsilon26-[2-(2-[2-(2-[2-(2-[4-(19-carboxynonade-canoylamino)-4(S)-carboxybutyrylamino]ethoxy)ethoxy] acetylamino)ethoxy]ethoxy)acetyl][Aib8, Arg34]GLP-1-(7-37); N-epsilon26-[2-(2-[2-(2-[2-(2-[4-(17-carboxyheptade-canoylamino)-4(S)-carboxybutyrylamino]ethoxy)ethoxy] acetylamino)ethoxy]ethoxy)acetyl][3-(4-Imidazolyl)Pro-pionyl7,Arg34]GLP-1-(7-37); N-epsilon26-[2-(2-[2-(2-[2-(2-[4-(17-carboxyheptadecanoylamino)-(carboxymethyl-amino)acetylamino]ethoxy)ethoxy]acetylamino)ethoxy] ethoxy)acetyl][Aib8,Arg34]GLP-1-(7-37); N-epsilon26-[2-(2-[2-(2-[2-(2-[4-(17-carboxyheptadecanoylamino)-3(S)-Sulfopropionylamino]ethoxy)ethoxy]acetylamino)ethoxy] ethoxy)acetyl][Aib8, Arg34]GLP-1-(7-37); N-epsilon26-[2-(2-[2-(2-[2-(2-[4-(17-carboxyheptadecanoylamino)-4(S)-carboxybutyrylamino]ethoxy)ethoxy]acetylamino)ethoxy] ethoxy)acetyl][Gly8, Arg34] GLP-1-(7-37); N-epsilon26-[2-(2-[2-(2-[2-(2-[4-(17-carboxyheptadecanoylamino)-4 (S)-carboxybutyrylamino]ethoxy)ethoxy]acetylamino) ethoxy]ethoxy)acetyl][Aib8, Arg34]GLP-1-(7-37)-amide; N-epsilon26-[2-(2-[2-(2-[2-(2-[4-(17-carboxyheptade-canoylamino)-4(S)-carboxybutyrylamino]ethoxy)ethoxy] acetylamino)ethoxy]ethoxy)acetyl][Aib8,Arg34,Pro37] GLP-1-(7-37)amide; Aib8,Lys26(N-epsilon26-{2-(2-(2-[2-(2-(4-(pentadecanoylamino)-4-carboxybutyrylamino) ethoxy)ethoxy]acetyl)ethoxy) ethoxy)acetyl)}), Arg34) GLP-1H(7-37)-OH; N-epsilon26-[2-(2-[2-(2-[2-(2-[4-{[N-(2-carboxyethyl)-N-(17-carboxyheptadecanoyl)amino] methyl}benzoyl)amino]ethoxy) ethoxy]acetylamino) ethoxy]ethoxy)acetyl][Aib8,Arg34]GLP-1(7-37); N-alpha7-formyl, N-epsilon26-[2-(2-[2-(2-[2-(2-[4-(17-car-boxyheptadecanoyl-amino)-4(S)-carboxy-butyrylamino) ethoxy]acetylamino)ethoxy]ethoxy)acetyl][Arg34] GLP-1-(7-37); N-epsilon2626-[2-(2-[2-(2-[2-(2-[4-(17- carboxy-heptadecanoylamino)-4(S)-carboxy-butyrylamino] ethoxy)ethoxy]acetylamino)ethoxy]ethoxy]ethoxy)acetyl][Aib8, Glu22,Arg34]GLP-1-(7-37); N-epsilon26{3-[2-(2-{2-[2-(2-{2-[2-(2-[4-(15-(N—((S)-1,3-dicarboxypropyl) carbamoyl) pentadecanoylamino)-(S)-4-carboxybutyrylamino] ethoxy) ethoxy] ethoxy}ethoxy)ethoxy]ethoxy}ethoxy)ethoxy] propionyl}[Aib8,Arg34]GLP-1-(7-37); N-epsilon26-[2-(2-[2-(2-[2-(2-[4-{[N-(2-carboxyethyl)-N-(17-carboxy-heptadecanoyl)amino]methyl}benzoyl)amino)-4(S)-carboxybutyryl-amino)ethoxy) ethoxy]acetylamino)ethoxy] ethoxy)acetyl][Aib8,Arg34] GLP-1(7-37); N-epsilon26-{(S)-4-carboxy-4-((S)-4-carboxy-4-((S)-4-carboxy-4-((S)-4-carboxy-4-(19-carboxy-nonadecanoylamino)butyry-lamino)butyrylamino)butyrylamino) butyrylamino} [Aib8, Arg34]GLP-1-(7-37); N-epsilon26-4-(17-carboxyheptadecanoyl-amino)-4(S)-carboxybutyryl-[Aib8, Arg34]GLP-1-(7-37); N-epsilon26- {3-[2-(2-{2-[2-(2-{2-[2-(2-[4-(17-carboxyheptadecanoylamino)-4(S)-carboxybutyrylamino]ethoxy)ethoxy]ethoxy} ethoxy) ethoxy]ethoxy}ethoxy)ethoxy]propionyl}[Aib8,Arg34] GLP-1-(7-37); N-epsilon26-{2-(2-(2-(2-[2-(2-(4-(17-carboxyheptadecanoylamino)-4-carboxybutyrylamino) ethoxy)ethoxy]acetyl)ethoxy)ethoxy)acetyl)}-Aib8,22,27, 30,35,Arg34,Pro37,Lys26]GLP-1 (7-37)amide; N-epsilon26-[2-(2-[2-[4-(21-carboxyuneicosanoylamino)-4(S)-carboxybutyrylamino]ethoxy]ethoxy)acetyl][Aib8,Arg34] GLP-1-(7-37); and N-epsilon26-[2-(2-[2-(2-[2-(2-[4-(21-carboxyuneicosanoylamino)-4(S)-carboxybutyrylamino] ethoxy)ethoxy]acetylamino)ethoxy]ethoxy)acetyl][Aib8, Arg34]GLP-1-(7-37).

Delivery Agent

Salt of N-(8-(2-Hydroxybenzoyl)Amino)Caprylic Acid

The delivery agent used in the present invention is a salt of N-(8-(2-hydroxybenzoyl)amino)caprylic acid (NAC). The structural formula of N-(8-(2-hydroxybenzoyl)amino) caprylate is shown in formula (I).

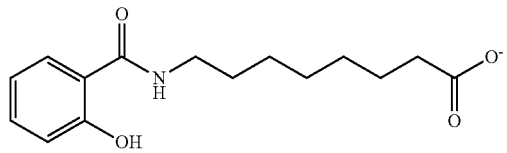

(I)

In some embodiments the salt of N-(8-(2-hydroxybenzoyl)amino)caprylic acid comprises one monovalent cation, two monovalent cations or one divalent cation. In some embodiments the salt of N-(8-(2-hydroxybenzoyl)amino) caprylic acid is selected from the group consisting of the sodium salt, potassium salt and/or calcium salt of N-(8-(2-hydroxybenzoyl)amino)caprylic acid. In one embodiment the salt of N-(8-(2-hydroxybenzoyl)amino)caprylic acid is selected from the group consisting of the sodium salt, potassium salt and/or the ammonium salt. In one embodiment the salt of N-(8-(2-hydroxybenzoyl)amino)caprylic acid is the sodium salt or the potassium salt. Salts of N-(8-(2-hydroxybenzoyl)amino)caprylate may be prepared using the method described in e.g. WO96/030036, WO00/046182, WO01/092206 or WO2008/028859.

The salt of N-(8-(2-hydroxybenzoyl)amino)caprylic acid may be crystalline and/or amorphous. In some embodiments the delivery agent comprises the anhydrate, monohydrate, dihydrate, trihydrate, a solvate or one third of a hydrate of the salt of N-(8-(2-hydroxybenzoyl)amino)caprylic acid as well as combinations thereof. In some embodiments the delivery agent is a salt of N-(8-(2-hydroxybenzoyl)amino) caprylic acid as described in WO2007/121318.

In some embodiments the delivery agent is sodium N-(8-(2-hydroxybenzoyl)amino)caprylate (referred to as "SNAC" herein), also known as sodium 8-(salicyloylamino)octanoate.

Composition

The composition or pharmaceutical composition of the present invention is a solid or dry composition suited for administration by the oral route as described further herein below.

In some embodiments the composition comprises at least one pharmaceutically acceptable excipient. The term "excipient" as used herein broadly refers to any component other than the active therapeutic ingredient(s) or active pharmaceutical ingredient(s) (API(s)). A excipient may be a pharmaceutically inert substance, an inactive substance, and/or a therapeutically or medicinally none active substance.

The excipients may serve various purposes, e.g. as a carrier, vehicle, filler, binder, lubricant, glidant, disintegrant, flow control agent, crystallization inhibitors, solubilizer, stabilizer, colouring agent, flavouring agent, surfactant, emulsifier or combinations of thereof and/or to improve administration, and/or absorption of the therapeutically active substance(s) or active pharmaceutical ingredient(s). The amount of each excipient used may vary within ranges conventional in the art. Techniques and excipients which may be used to formulate oral dosage forms are described in Handbook of Pharmaceutical Excipients, 8th edition, Sheskey et al., Eds., American Pharmaceuticals Association and the Pharmaceutical Press, publications department of the Royal Pharmaceutical Society of Great Britain (2017); and Remington: the Science and Practice of Pharmacy, 22nd edition, Remington and Allen, Eds., Pharmaceutical Press (2013).

In some embodiments the excipients may be selected from binders, such as polyvinyl pyrrolidone (povidone), etc.; fillers such as cellulose powder, microcrystalline cellulose, cellulose derivatives like hydroxymethylcellulose, hydroxyethylcellulose, hydroxypropylcellulose and hydroxy-propylmethylcellulose, dibasic calcium phosphate, corn starch, pregelatinized starch, etc.; lubricants and/or glidants such as stearic acid, magnesium stearate, sodium stearylfumarate, glycerol tribehenate, etc.; flow control agents such as colloidal silica, talc, etc.; crystallization inhibitors such as Povidone, etc.; solubilizers such as Pluronic, Povidone, etc.; colouring agents, including dyes and pigments such as iron oxide red or yellow, titanium dioxide, talc, etc.; pH control agents such as citric acid, tartaric acid, fumaric acid, sodium citrate, dibasic calcium phosphate, dibasic sodium phosphate, etc.; surfactants and emulsifiers such as Pluronic, polyethylene glycols, sodium carboxymethyl cellulose, polyethoxylated and hydrogenated castor oil, etc.; and mixtures of two or more of these excipients and/or adjuvants.

The composition may comprise a binder, such as povidone; starches; celluloses and derivatives thereof, such as microcrystalline cellulose, e.g., Avicel PH from FMC (Philadelphia, PA), hydroxypropyl cellulose hydroxylethyl cellulose and hydroxylpropylmethyl cellulose (METHOCEL) from Dow Chemical Corp. (Midland, MI); sucrose; dextrose; corn syrup; polysaccharides; and gelatine. The binder may be selected from the group consisting of dry binders and/or wet granulation binders. Suitable dry binders are, e.g., cellulose powder and microcrystalline cellulose, such as Avicel PH 102 and Avicel PH 200. In some embodiments the composition comprises Avicel, such as Avicel PH 102. Suitable binders for wet granulation or dry granulation are corn starch, polyvinyl pyrrolidone (povidone), vinylpyrrolidone-vinylacetate copolymer (copovidone) and cellulose derivatives like hydroxymethylcellulose, hydroxyethylcellulose, hydroxypropylcellulose and hydroxyl-propylmethylcellulose. In some embodiments the composition comprises povidone.

In some embodiments the composition comprises a filler, which may be selected from lactose, mannitol, erythritol, sucrose, sorbitol, calcium phosphate, such as calciumhydrogen phosphate, microcrystalline cellulose, powdered cellulose, confectioner's sugar, compressible sugar, dextrates, dextrin and dextrose. In some embodiments the composition comprises microcrystalline cellulose, such as Avicel PH 102 or Avicel PH 200.

In some embodiments the composition comprises a lubricant and/or a glidant. In some embodiments the composition comprises a lubricant and/or a glidant, such as talc, magnesium stearate, calcium stearate, zinc stearate, glyceryl behenate, glyceryl dibehenate, behenoyl polyoxyl-8 glycerides, polyethylene oxide polymers, sodium lauryl sulfate, magnesium lauryl sulfate, sodium oleate, sodium stearyl fumarate, stearic acid, hydrogenated vegetable oils, silicon dioxide and/or polyethylene glycol etc. In some embodiments the composition comprises magnesium stearate or glyceryl dibehenate (such as the product COMPRITOL® 888 ATO which consists of mono-, di- and triesters of behenic acid (C22) with the diester fraction being predominant).

In some embodiments the composition comprises a disintegrant, such as sodium starch glycolate, polacrilin potassium, sodium starch glycolate, crospovidon, croscarmellose, sodium carboxymethylcellulose or dried corn starch.

The composition may comprise one or more surfactants, for example a surfactant, at least one surfactant, or two different surfactants. The term "surfactant" refers to any molecules or ions that are comprised of a water-soluble (hydrophilic) part, and a fat-soluble (lipophilic) part. The surfactant may e.g. be selected from the group consisting of anionic surfactants, cationic surfactants, nonionic surfactants, and/or zwitterionic surfactants.

As shown in the examples herein, the compositions of the invention have a very high content of the delivery agent. This very high content can be defined relative to the full content of the tablets including also the active pharmaceutical ingredient (i.e. the GLP-1 agonist) or alternatively relative to the total content of excipients excluding the active pharmaceutical ingredient. The description here below also refers to compositions consisting of specific ingredients, the GLP-1 agonist and excipients, the term consisting is to be understood to never the less encompass trace amounts of any substance with no effect on the function of the composition, which may also be referred to as consisting essential of. Such substances can be impurities remaining in preparation of the GLP-1 agonist or from the production of the salt of NAC or minimal amounts (below 1%) of any pharmaceutical acceptable excipient that do not affect the quality or absorption of the formulation.

In one embodiment the pharmaceutical composition comprises
a. a GLP-1 agonist and
b. a salt of N-(8-(2-hydroxybenzoyl)amino)caprylic acid (NAC)
wherein said salt of N-(8-(2-hydroxybenzoyl)amino) caprylic acid (NAC) constitutes at least or above 90 w/w % of the composition.

In further such embodiments the salt of NAC constitutes above 91%, such as above 92%, such as above 93, such as above 94%, such as above 95 w/w % of said composition.

In further such embodiments the salt of NAC constitutes at least 91 w/w %, such as at least 92 w/w %, such as at least 93 w/w %, such as at least 94 w/w %, such as at least 95 w/w % of said composition.

In one embodiment the pharmaceutical composition comprises
a) a GLP-1 agonist and
b) a salt of N-(8-(2-hydroxybenzoyl)amino)caprylic acid (NAC),
wherein said salt of N-(8-(2-hydroxybenzoyl)amino) caprylic acid (NAC) constitutes at least 90 w/w % of the excipients of the composition.

In one embodiment the pharmaceutical composition consists of
a) a GLP-1 agonist and
b) excipients, wherein the excipients are
 i. a salt of N-(8-(2-hydroxybenzoyl)amino)caprylic acid (NAC) and
 ii. one or more further excipients
wherein said salt of N-(8-(2-hydroxybenzoyl)amino) caprylic acid (NAC) constitutes at least 90 w/w % of the excipients of the composition.

In further such embodiments the salt of NAC constitutes at least at least 91 w/w %, such as at least 92 w/w %, such as at least 93 w/w %, such as at least 94 w/w %, such as at least 95 w/w % of the excipients of the composition.

In one embodiment the pharmaceutical composition comprises
a) a GLP-1 agonist and
b) a salt of N-(8-(2-hydroxybenzoyl)amino)caprylic acid (NAC),
wherein said salt of N-(8-(2-hydroxybenzoyl)amino) caprylic acid (NAC) constitutes at least 95 w/w % of the excipients of the composition.

In one embodiment the pharmaceutical composition consists of
a) a GLP-1 agonist and
b) excipients, wherein the excipients are
 i. a salt of N-(8-(2-hydroxybenzoyl)amino)caprylic acid (NAC) and
 ii. one or more further excipients
wherein said salt of N-(8-(2-hydroxybenzoyl)amino) caprylic acid (NAC) constitutes at least 95 w/w % of the excipients of the composition.

In further such embodiments the salt of NAC constitutes above 95 w/w %, such as above 96 w/w %, such as above 97 w/w % or such as above 98 w/w % of the composition.

In further such embodiments the salt of NAC constitutes at least 95 w/w %, such as at least 96 w/w %, such as at least 97 w/w % or such as at least 98 w/w % of the excipients of the composition.

As mentioned above, the content of excipients, besides the delivery agent is according to the invention preferably minimal. In one embodiment, the pharmaceutical composition comprises at least one lubricant.

In one embodiment the pharmaceutical composition comprises or consists of:
a) a GLP-1 agonist,
b) a salt of N-(8-(2-hydroxybenzoyl)amino)caprylic acid (NAC) and
c) at least one lubricant.

In such embodiments the lubricant may be magnesium stearate or glyceryl dibehenate. In one embodiment the lubricant is magnesium stearate. In one embodiment the lubricant is glyceryl dibehenate.

A composition as described above wherein said salt of N-(8-(2-hydroxybenzoyl)amino)caprylic acid (NAC) constitutes at least 95 w/w % of the excipients of the composition may further be a composition wherein said salt constitutes at least or above 90 w/w % of the composition.

Likewise the compositions described above wherein said salt constitutes at least or above 90 w/w % of the composition may further be a composition wherein said salt of N-(8-(2-hydroxybenzoyl)amino)caprylic acid (NAC) constitutes at least 95 w/w % of the excipients of the composition.

The pharmaceutical composition may further be a composition wherein the salt of N-(8-(2-hydroxybenzoyl)amino) caprylic acid (NAC) is selected from the group consisting of the sodium salt, potassium salt and/or calcium salt of N-(8-(2-hydroxybenzoyl)amino)caprylic acid (NAC) or alternatively from the group consisting of just the sodium salt and the potassium salt. In one embodiment the salt of N-(8-(2-hydroxybenzoyl)amino)caprylic acid (NAC) is sodium N-(8-(2-hydroxybenzoyl)amino)caprylate.

In embodiments wherein said salt of N-(8-(2-hydroxybenzoyl)amino)caprylic acid (NAC) constitutes at least 90 w/w % of the excipients of the composition, the composition comprises at most 10 w/w % of any further excipients, such as binder, filler, and/or lubricant/glidant. In some embodiments the composition comprises at least or above 90 w/w % delivery agent, and less than 5 w/w % of any further excipients, such as binder, filler, and/or lubricant/glidant. In one embodiment the pharmaceutical composition comprises at least 90 w/w % delivery agent and less than 5 w/w % lubricant. In one embodiment the pharmaceutical composition comprises at least 90 w/w % delivery agent and less than 3 w/w % lubricant.

In some embodiments the composition comprises at least or above 90 w/w % delivery agent and 0.1-5 w/w %, such as 0.5-4 w/w % or 1-3 w/w %, of lubricant. In further such embodiments the composition comprises 2-2.5 w/w % of lubricant.

In embodiments wherein said salt of N-(8-(2-hydroxybenzoyl)amino)caprylic acid (NAC) constitutes at least 95 w/w % of the excipients of the composition, the composition comprises at most 5 w/w % of any further excipients, such as binder, filler, and/or lubricant/glidant. In some embodiments the composition comprises at least 95 w/w % delivery agent and less than 5 w/w % lubricant. In one embodiment the pharmaceutical composition comprises at least 95 w/w % delivery agent and less than 3 w/w % lubricant.

In some embodiments the composition comprises at least 95 w/w % delivery agent and 0.1-5 w/w %, such as 0.5-4 w/w % or 1-3 w/w %, of lubricant. In further such embodiments the composition comprises 2-2.5 w/w % of lubricant.

The pharmaceutical composition according to the invention is preferably produced in a dosage form suitable for oral administration as described herein below. In the following the absolute amounts of the ingredients of the composition of the invention are provided with reference to the content in a dosage unit i.e. per tablet, capsule or sachet.

The pharmaceutical compositions of the invention may in a further embodiment comprise at most 1000 mg of said salt of N-(8-(2-hydroxybenzoyl)amino)caprylic acid per dose unit. In one embodiment the invention relates to a composition wherein a dose unit comprises at most 500 mg of said salt.

In some embodiments the amount of the salt of N-(8-(2-hydroxybenzoyl) amino)caprylic acid per dose unit is at least 0.05 mmol, such as at least 0.075 mmol, such as at least 0.1 mmol, such as at least 0.125 mmol, such as at least 0.15 mmol, such as at least 0.20 mmol, at least 0.25 mmol, at least 0.30 mmol, at least 0.35 mmol, at least 0.40 mmol, at least 0.45 mmol, at least 0.50 mmol, at least 0.55 mmol or at least 0.60 mmol.

In some embodiments the amount of the salt of N-(8-(2-hydroxybenzoyl)amino)caprylic acid per dosage unit of the composition is up to 3 mmol, such as up to 2.75 mmol, such as up to 2.5 mmol, such as up to 2.25 mmol, such as 2 mmol, such as up to 1.5 mmol, up to 1 mmol, up to 0.75 mmol, up to 0.6 mmol, up to 0.5 mmol, up to 0.4 mmol, up to 0.3 mmol and up to 0.2 mmol.

In some embodiments the amount of the salt of N-(8-(2-hydroxybenzoyl) amino)caprylic acid per dose unit of the composition is in the range of 0.05-3 mmol, 0.10-2.5 mmol, 0.15-2.0 mmol, 0.20-1.5 mmol, 0.25-1.0 mmol, 0.30-0.75 mmol or such as 0.45-0.65 mmol.

In some embodiments, where the salt of NAC is SNAC, the amount of SNAC in the composition is at least 20 mg, such as at least 25 mg, such as at least 50 mg, such as at least 75 mg, at least 100 mg, at least 125 mg, at least 150 mg, at least 175 mg, at least 200 mg, at least 225 mg, at least 250 mg, at least 275 mg and at least 300 mg per dose unit.

In some embodiments, where the salt of NAC is SNAC, the amount of SNAC in the composition is up to 800 mg, such as up to 600 mg, such as up to 575 mg, such as up to 550 mg, up to 525 mg, up to 500 mg, up to 475 mg, up to 450 mg, up to 425 mg, up to 400 mg, up to 375 mg, up to 350 mg, up to 325 mg per dose unit, or up to 300 mg per dose unit.

In some embodiments, where the salt of NAC is SNAC, the amount of SNAC in the composition is in the range of 20-800 mg, such as 25-600 mg, such as 50-500 mg, such as 50-400 mg, such as 75-400 mg, such as 80-350 mg or such as from around 100 to around 300 mg per dose unit.

In one embodiment, where the salt of NAC is SNAC, the amount of SNAC is in the range of 20-200 mg, such as 25-175 mg, such as 75-150 mg, such as 80-120 mg such as around 100 mg per dose unit.

In one embodiment, where the salt of NAC is SNAC, the amount of SNAC is in the range of 200-800 mg, such as 250-400 mg, such as 250-350 mg, such as 275-325 mg, such as around 300 mg per dose unit.

In an embodiment, a dose unit of the pharmaceutical compositions of the invention comprises 0.1-100 mg or 0.2 to 100 mg of the GLP-1 agonist.

In some embodiments a dose unit of the composition comprises an amount of GLP-1 agonist is in the range of 0.2 to 50 mg or 1 to 40 mg.

In some embodiments a dose unit comprises 0.5-5 mg of the GLP-1 agonist, such as 0.75-4.5 mg, such as 1, 1.5, 2, 2.5 or 3 mg or 3.5, 4, 4.5 mg, such as 1-3 or 3-5 mg of the GLP-1 agonist per dose unit.

In some embodiments a dose unit comprises 2 to 20 mg of the GLP-1 agonist, such as 2-15 mg, such as 2, 3, 4, 5, 6 or 7 mg, such as 2, 3, 4 or 5 mg, or such as 8, 10, 12 or 14 mg, such as 15 mg or such as 20 mg of the GLP-1 agonist per dose unit.

In some embodiments a dose unit comprises 5 to 50 mg of the GLP-1 agonist, such as 10-45 mg, such as 20, 30 or 40 mg, or such as 25, 35, or 45 mg, or such as 30-50 mg or such as 20-40 mg of the GLP-1 agonist per dose unit.

The amount of GLP-1 agonist may be varied depending on identity of the GLP-1 agonist and the effect desired, i.e. a higher content may be relevant for treating obesity compared to diabetes.

In a preferred embodiment a unit dose of the composition comprises 0.5-25 mg magnesium stearate, such as 1-10 mg, such as 2-8 mg or such as 2-5 mg magnesium stearate.

In a preferred embodiment the amount of magnesium stearate is determined relative to the amount of the salt of NAC, such as SNAC, such that a unit dose of the composition comprises 1-8 mg magnesium stearate or such as 2-5 mg magnesium stearate or 2-3 mg magnesium stearate per 100 mg salt of N-(8-(2-hydroxybenzoyl)amino)caprylic acid, such as SNAC.

In a preferred embodiment a unit dose of the composition comprises 80-120 mg SNAC, 0.5-5 mg GLP-1 agonist and 2-3 mg lubricant.

In a preferred embodiment a unit dose of the composition comprises 80-120 mg SNAC, 1.5-10 mg GLP-1 agonist and 2-3 mg lubricant.

In a preferred embodiment a unit dose of the composition comprises 80-120 mg SNAC, 5-50 mg GLP-1 agonist and 2-3 mg lubricant.

In a preferred embodiment a unit dose of the composition comprises 250-350 mg SNAC, 0.5-5 mg GLP-1 agonist and 3-10 mg lubricant.

In a preferred embodiment a unit dose of the composition comprises 250-350 mg SNAC, 1.5-10 mg GLP-1 agonist and 3-10 mg lubricant.

In a preferred embodiment a unit dose of the composition comprises 250-350 mg SNAC, 5-50 mg GLP-1 agonist and 3-10 mg lubricant.

In one embodiment the pharmaceutical composition of the invention has a fast release in vitro. Release or dissolution may be tested as known in the art and as described here in Assay I. The release may be expressed as the amount of the GLP-1 agonist measured in solution after a given period relative to the total content of the GLP-1 agonist of the composition. The relative amount may be given in percentage. In one embodiment the release of the GLP-1 agonist from the pharmaceutical composition of the invention is at least 85% within 15 minutes or at least 95% within 30 minutes. In one such embodiment the release is measured at pH 6.8.

In one embodiment the pharmaceutical composition comprises
a) a GLP-1 agonist and
b) a salt of N-(8-(2-hydroxybenzoyl)amino)caprylic acid, wherein the release of the GLP-1 agonist reaches 85% within 15 minutes or 95% within 30 minutes. In one embodiment the release is measured at pH 6.8.

In one embodiment the pharmaceutical composition of the invention provides an early exposure in vivo. In one embodiment the pharmaceutical composition of the invention provides an increased exposure in vivo. In one embodiment the pharmaceutical composition of the invention provides an increased early exposure in vivo. Such in vivo exposure may be tested in a relevant model, such as the Assay III described herein. As seen in table 3.1 the compositions disclosed herein demonstrate an increased early dose corrected exposure in beagle dogs within the first 30 minutes after oral dosing. The exposure may also be measured over a predetermined time period and the accumulative dose corrected exposure (AUC) calculated, such as for t=0-30 minutes as also provided in table 3.1 for the compositions described herein.

In one embodiment the invention relates to a pharmaceutical composition wherein the dose corrected exposure at t=30 min is increased relative to the composition described in WO2013/139694, which comprise the additional excipients microcrystalline cellulose and povidone. The Reference composition for a given GLP-1 agonist should preferable be prepared with two granules as disclosed for type F and H in WO2013/139694, and prepared by substituting semaglutide/Compound A with the GLP-1 agonist of interest.

In one embodiment the pharmaceutical composition comprises
a) a GLP-1 agonist and
b) a salt of N-(8-(2-hydroxybenzoyl)amino)caprylic acid, wherein the dose corrected exposure at t=30 min is increased relative to a composition of type F/H of WO2013/139694.

In one embodiment the pharmaceutical composition comprises
a) a GLP-1 agonist and
b) a salt of N-(8-(2-hydroxybenzoyl)amino)caprylic acid, wherein the dose corrected exposure (AUC) for t=0-30 min is increased relative to a composition of type F/H of WO2013/139694.

In one embodiment the dose corrected exposure (AUC) for t=0-30 min is increased at least 1.5 fold, such as 2 fold compared to a composition of type F/H of WO2013/139694.

Dosage Form

The composition may be administered in several dosage forms, for example as a tablet; a coated tablet; a sachet or a capsule such as hard or soft shell capsules.

The composition may further be compounded in a drug carrier or drug delivery system, e.g. in order to improve stability and/or solubility or further improve bioavailability. The composition may be a freeze-dried or spray-dried composition.

The composition may be in the form of a dose unit, such as a tablet. In some embodiments the weight of the unit dose is in the range of 50 mg to 1000 mg, such as in the range of 50-750 mg, or such as in the range of 100-500 mg.

In some embodiments the weight of the dose unit is in the range of 75 mg to 350 mg, such as in the range of 100-300 mg or such as in the range of 200-350 mg.

In some embodiments the weight of the dose unit is in the range of 100 mg to 400 mg, such as in the range of 50-300 mg or such as in the range of 200-400 mg.

In some embodiments the composition may be granulated prior to being compacted. The composition may comprise an intragranular part and/or an extragranular part, wherein the intragranular part has been granulated and the extragranular part has been added after granulation.

The intragranular part may comprise the GLP-1 agonist, the delivery agent and/or an excipient, such as a lubricant and/or glidant. In some embodiments the intragranular part comprises the delivery agent and a lubricant and/or a glidant.

The extragranular part may comprise a GLP-1 agonist, and/or a lubricant and/or a glidant, such as magnesium stearate. In some embodiments the extragranular part comprises the GLP-1 agonist. In some embodiments the extragranular part comprises an excipient, such as a lubricant and/or glidant, such as magnesium stearate.

In further embodiments the intragranular part comprises the GLP-1 agonist, the delivery agent and the lubricant and/or a glidant. In such embodiments the granulate may be directly compressed into tablets and the tablets have no extragranular part.

Preparation of Composition

Preparation of a composition according to the invention may be performed according to methods known in the art.

To prepare a dry blend of tabletting material, the various components are weighed, optionally delumped or sieved and then combined. The mixing of the components may be carried out until a homogeneous blend is obtained.

If granules are to be used in the tabletting material, granules may be produced in a manner known to a person skilled in the art, for example using wet granulation methods known for the production of "built-up" granules or "broken-down" granules. Methods for the formation of built-up granules may operate continuously and comprise, for example simultaneously spraying the granulation mass with granulation solution and drying, for example in a drum granulator, in pan granulators, on disc granulators, in a fluidized bed, by spray-drying, spray-granulation or spray-solidifying, or operate discontinuously, for example in a fluidized bed, in a rotary fluid bed, in a batch mixer, such as a high shear mixer or a low shear mixer, or in a spray-drying drum. Methods for the production of broken-down granules, which may be carried out discontinuously and in which the granulation mass first forms a wet aggregate with the granulation solution, which is subsequently comminuted or by other means formed into granules of the desired size and the granules may then be dried. Suitable equipment for the wet granulation step are planetary mixers, low shear mixers, high shear mixers, extruders and spheronizers, such as an apparatus from the companies Loedige, Glatt, Diosna, Fielder, Collette, Aeschbach, Alexanderwerk, Ytron, Wyss & Probst, Werner & Pfleiderer, HKD, Loser, Fuji, Nica, Caleva and Gabler. Granules may also be formed by dry granulation techniques in which one or more of the excipient (s) and/or the active pharmaceutical ingredient is compressed to form relatively large moldings, for example slugs or ribbons, which are comminuted by grinding, and the ground material serves as the tabletting material to be later compacted. Suitable equipment for dry granulation is, but not limited to, roller compaction equipment from Gerteis such as Gerteis MICRO-PACTOR, MINI-PACTOR and MACRO-PACTOR.

The terms "granulate" and "granules" are used interchangeably herein to refer to particles of composition material which may be prepared as described above.

To compact the tabletting material into a solid oral dosage form, for example a tablet, a tablet press may be used. In a tablet press, the tabletting material is filled (e.g. force fed or gravity fed) into a die cavity. The tabletting material is then compacted by a set of punches applying pressure. Subsequently, the resulting compact, or tablet is ejected from the tablet press. The above mentioned tabletting process is subsequently referred to herein as the "compaction process". Suitable tablet presses include, but are not limited to, rotary tablet presses and eccentric tablet presses. Examples of tablet presses include, but are not limited to, the Fette 102i (Fette GmbH), the Korsch XL100, the Korsch PH 106 rotary tablet press (Korsch AG, Germany), the Korsch EK-O eccentric tabletting press (Korsch AG, Germany) and the Manesty F-Press (Manesty Machines Ltd., United Kingdom).

In one embodiment the composition comprises at least one granulate. In one embodiment the composition comprises one type of granulate. The composition may alternatively comprise two types of granulates.

In some embodiments the method of preparation of the tablet comprises; a) granulating a mixture comprising the delivery agent and optionally a lubricant; b) blending the granulate of a) with a GLP-1 agonist and optionally additional lubricant, and then c) compressing the blend of b) into tablets.

In some embodiments the method of preparation of the tablet comprises; a) granulating a mixture comprising the delivery agent, the GLP-1 agonist and optionally a lubricant and b) compressing the granulate of a) into tablets and optionally including additional lubricant.

In general, granulates may be prepared by wet, melt or dry granulation, preferably dry granulation.

Pharmaceutical Indications

The present invention also relates to a composition of the invention for use as a medicament. In particular embodiments the composition of the invention may be used for the following medical treatments, all preferably relating one way or the other to diabetes and/or obesity:

(i) prevention and/or treatment of all forms of diabetes, such as hyperglycemia, type 2 diabetes, impaired glucose tolerance, type 1 diabetes, non-insulin dependent diabetes, MODY (maturity onset diabetes of the young), gestational diabetes, and/or for reduction of HbA1C;

(ii) delaying or preventing diabetic disease progression, such as progression in type 2 diabetes, delaying the progression of impaired glucose tolerance (IGT) to insulin requiring type 2 diabetes, and/or delaying the progression of non-insulin requiring type 2 diabetes to insulin requiring type 2 diabetes;

(iii) improving β-cell function, such as decreasing β-cell apoptosis, increasing β-cell function and/or β-cell mass, and/or for restoring glucose sensitivity to β-cells;

(iv) prevention and/or treatment of cognitive disorders;

(v) prevention and/or treatment of eating disorders, such as obesity, e.g. by decreasing food intake, reducing body weight, suppressing appetite, inducing satiety; treating or preventing binge eating disorder, bulimia nervosa, and/or obesity induced by administration of an antipsychotic or a steroid; reduction of gastric motility; and/or delaying gastric emptying;

(vi) prevention and/or treatment of diabetic complications, such as neuropathy, including peripheral neuropathy; nephropathy; or retinopathy;

(vii) improving lipid parameters, such as prevention and/or treatment of dyslipidemia, lowering total serum lipids; lowering HDL; lowering small, dense LDL; lowering VLDL: lowering triglycerides; lowering cholesterol; increasing HDL; lowering plasma levels of lipoprotein a (Lp(a)) in a human; inhibiting generation of apolipoprotein a (apo(a)) in vitro and/or in vivo;

(iix) prevention and/or treatment of cardiovascular diseases, such as syndrome X; atherosclerosis; myocardial infarction; coronary heart disease; stroke, cerebral ischemia; an early cardiac or early cardiovascular disease, such as left ventricular hypertrophy; coronary artery disease; essential hypertension; acute hypertensive emergency; cardiomyopathy; heart insufficiency; exercise tolerance; chronic heart failure; arrhythmia; cardiac dysrhythmia; syncopy; atheroschlerosis; mild chronic heart failure; angina pectoris; cardiac bypass reocclusion; intermittent claudication (atheroschlerosis oblitterens); diastolic dysfunction; and/or systolic dysfunction;

(ix) prevention and/or treatment of gastrointestinal diseases, such as inflammatory bowel syndrome; small bowel syndrome, or Crohn's disease; dyspepsia; and/or gastric ulcers;

(x) prevention and/or treatment of critical illness, such as treatment of a critically ill patient, a critical illness poly-nephropathy (CIPNP) patient, and/or a potential CIPNP patient; prevention of critical illness or development of CIPNP; prevention, treatment and/or cure of systemic inflammatory response syndrome (SIRS) in a patient; and/or for the prevention or reduction of the likelihood of a patient suffering from bacteraemia, septicaemia, and/or septic shock during hospitalisation; and/or (xi) prevention and/or treatment of polycystic ovary syndrome (PCOS).

In a particular embodiment, the indication is selected from the group consisting of (i)-(iii) and (v)-(iix), such as indications (i), (ii), and/or (iii); or indication (v), indication (vi), indication (vii), and/or indication (iix). In another particular embodiment, the indication is (i). In a further particular embodiment the indication is (v). In a still further particular embodiment the indication is (iix). In some embodiments the indications are type 2 diabetes and/or obesity.

Method of Treatment

The invention further relates to a method of treating a subject in need thereof, comprising administering a therapeutically effective amount of a composition according to the present invention to said subject. In one embodiment the method of treatment is for treatment of diabetes or obesity and/or the further indications specified above.

In some embodiments, a method for treating diabetes is described comprising administering to a subject in need thereof a therapeutically effective amount of a pharmaceutical composition comprising a GLP-1 agonist, a salt of N-(8-(2-hydroxybenzoyl)amino)caprylic acid (NAC), and optionally, a lubricant.

In some embodiments, a method for treating diabetes is described comprising administering to a subject in need thereof a therapeutically effective amount of a pharmaceutical composition comprising 0.5-50 mg of a GLP-1 agonist, 50-500 mg of salt of N-(8-(2-hydroxybenzoyl)amino) caprylic acid (NAC), and 1-10 mg lubricant. In a preferred embodiment, the salt of N-(8-(2-hydroxybenzoyl)amino) caprylic acid constitutes at least 90% (w/w) of the composition.

In a preferred embodiment, the salt of N-(8-(2-hydroxybenzoyl)amino)caprylic acid constitutes at least 95% (w/w) of the excipients of the composition.

In an alternative embodiment, a method for treating diabetes is described comprising administering to a subject in need thereof a therapeutically effective amount of a pharmaceutical composition comprising about 1-14 mg of a GLP-1 agonist, about 100-300 mg of salt of N-(8-(2-hydroxybenzoyl)amino)caprylic acid (NAC), and about 2-8 mg of magnesium stearate.

In some embodiments, the GLP-1 agonist is semaglutide having a formula of N-epsilon26-[2-(2-{2-[2-(2-{2-[(S)-4-carboxy-4-(17-carboxy-heptadecanoylamino)butyrylamino]ethoxy}ethoxy)acetylamino]ethoxy}ethoxy)acetyl][Aib8,Arg34]GLP-1(7-37) and the salt of N-(8-(2-hydroxybenzoyl)amino)caprylic acid (NAC) is sodium N-(8-(2-hydroxybenzoyl)amino)caprylic acid (SNAC). Various examples of a lubricant are described, including magnesium stearate. The composition is administered orally and is in a form of a table, capsule or a sachet.

In a further such embodiments one or more dose units may be administered to said subject in need.

Combination Treatment

The treatment with a composition according to the present invention may also be combined with one or more additional active pharmaceutical ingredient(s), e.g. selected from antidiabetic agents, antiobesity agents, appetite regulating agents, antihypertensive agents, agents for the treatment and/or prevention of complications resulting from or associated with diabetes and agents for the treatment and/or prevention of complications and disorders resulting from or associated with obesity. Examples of these pharmacologically active substances are: Insulin, sulphonylureas, biguanides, meglitinides, glucosidase inhibitors, glucagon antagonists, DPP-IV (dipeptidyl peptidase-IV) inhibitors, sodium glucose linked transporter 2 (SGLT2) inhibitors; canagliflozin, dapagliflozin, empagliflozin, ertugliflozin, ipragliflozin, tofogliflozin, luseogliflozin, bexagliflozin, remogliflozin etabonate and sotagliflozin, particularly dapagliflozin and empagliflozin, inhibitors of hepatic enzymes involved in stimulation of gluconeogenesis and/or glycogenolysis, glucose uptake modulators, compounds modifying the lipid metabolism such as antihyperlipidemic agents as HMG CoA inhibitors (statins), Gastric Inhibitory Polypeptides (GIP analogues), compounds lowering food intake, RXR agonists and agents acting on the ATP-dependent potassium channel of the β-cells; Cholestyramine, colestipol, clofibrate, gemfibrozil, lovastatin, pravastatin, simvastatin, probucol, dextrothyroxine, neteglinide, repaglinide; β-blockers such as alprenolol, atenolol, timolol, pindolol, propranolol and metoprolol, ACE (angiotensin converting enzyme) inhibitors such as benazepril, captopril, enalapril, fosinopril, lisinopril, alatriopril, quinapril and ramipril, calcium channel blockers such as nifedipine, felodipine, nicardipine, isradipine, nimodipine, diltiazem and verapamil, and α-blockers such as doxazosin, urapidil, prazosin and terazosin; CART (cocaine amphetamine regulated transcript) agonists, NPY (neuropeptide Y) antagonists, PYY agonists, Y2 receptor agonists, Y4 receptor agonists, mixed Y2/Y4 receptor agonists, MC4 (melanocortin 4) agonists, orexin antagonists, TNF (tumour necrosis factor) agonists, CRF (corticotropin releasing factor) agonists, CRF BP (corticotropin releasing factor binding protein) antagonists, urocortin agonists, β3 agonists, oxyntomodulin and analogues, MSH (melanocyte-stimulating hormone) agonists, MCH (melanocyte-concentrating hormone) antagonists, CCK (cholecystokinin) agonists, serotonin re-uptake inhibitors, serotonin and noradrenaline re-uptake inhibitors, mixed serotonin and noradrenergic compounds, 5HT (serotonin) agonists, bombesin agonists, galanin antagonists, growth hormone, growth hormone releasing compounds, TRH (thyreotropin releasing hormone) agonists, UCP 2 or 3 (uncoupling protein 2 or 3) modulators, leptin agonists, DA agonists (bromocriptin, doprexin), lipase/amylase inhibitors, RXR (retinoid X receptor) modulators, TR β agonists; histamine H3 antagonists, Gastric Inhibitory Polypeptide agonists or antagonists (GIP analogues), gastrin and gastrin analogues.

The invention as described herein is, without limitation hereto, further defined by the embodiments described here below and the claims of the document.

EMBODIMENTS

1. A pharmaceutical composition comprising
   a) a GLP-1 agonist and
   b) a salt of N-(8-(2-hydroxybenzoyl)amino)caprylic acid
   wherein said salt of N-(8-(2-hydroxybenzoyl)amino) caprylic acid constitutes at least 90 w/w % of the composition.

2. A pharmaceutical composition comprising
   a) a GLP-1 agonist and
   b) a salt of N-(8-(2-hydroxybenzoyl)amino)caprylic acid wherein said salt of N-(8-(2-hydroxybenzoyl)amino) caprylic acid constitutes at least 90 w/w %, such as at least 95 w/w % of the excipients of the composition.
3. A pharmaceutical composition consisting of
    a) a GLP-1 agonist and
    b) excipients, wherein the excipients are
        i. a salt of N-(8-(2-hydroxybenzoyl)amino)caprylic acid and
        ii. one or more further excipients
    wherein said salt of N-(8-(2-hydroxybenzoyl)amino) caprylic acid constitutes at least 90 w/w %, such as at least 95 w/w % of the excipients of the composition.
4. The pharmaceutical composition according to any of the previous embodiments 1-3, wherein the composition comprises at least one lubricant.
5. A pharmaceutical composition consisting of:
    a) a GLP-1 agonist,
    b) a salt of N-(8-(2-hydroxybenzoyl)amino)caprylic acid and
    c) at least one lubricant
6. The pharmaceutical composition according to any of the previous embodiments 4 and 5, wherein the lubricant is magnesium stearate.
7. The pharmaceutical composition according any of the previous embodiments, wherein the composition comprises 1-8 mg, such as 2-5 mg or such as 2-3 mg magnesium stearate per 100 mg salt of N-(8-(2-hydroxybenzoyl)amino)caprylic acid.
8. The pharmaceutical composition according to any of the previous embodiments 2-7, wherein said salt of N-(8-(2-hydroxybenzoyl)amino)caprylic acid constitutes at least 90 w/w % of the composition.
9. The pharmaceutical composition according to any of the previous embodiments 1, 5-8, wherein said salt of N-(8-(2-hydroxybenzoyl)amino)caprylic acid constitutes at least 95 w/w % of the excipients of the composition.
10. The pharmaceutical composition according to any of the previous embodiments, wherein the salt of N-(8-(2-hydroxybenzoyl)amino)caprylic acid is selected from the group consisting of the sodium salt, potassium salt and/or calcium salt of N-(8-(2-hydroxybenzoyl) amino)caprylic acid.
11. The pharmaceutical composition according to any of the previous embodiments, wherein the salt of N-(8-(2-hydroxybenzoyl)amino)caprylic acid is sodium N-(8-(2-hydroxybenzoyl)amino)caprylate (SNAC).
12. The pharmaceutical composition according to any of the previous embodiments, wherein a dose unit comprises at most 1000 mg of said salt of N-(8-(2-hydroxybenzoyl)amino)caprylic acid.
13. The pharmaceutical composition according to any of the previous embodiments, wherein a dose unit comprises 0.5-50 mg of the GLP-1 agonist.
14. The pharmaceutical composition according to any of the previous embodiments, wherein the GLP-1 agonist has T ½ of at least 24 hours in minpigs.
15. The pharmaceutical composition according to any of the previous embodiments, wherein the GLP-1 agonist has an EC50 (without HSA) of at most 100 pM, such as at most 50.
16. The pharmaceutical composition according to any of the previous embodiments, wherein the GLP-1 agonist is selected from the group consisting of: liraglutide, semaglutide, GLP-1 agonist B and GLP-1 agonist C.
17. The pharmaceutical composition according to any of the previous embodiments, wherein the GLP-1 agonist is selected from the group consisting of: semaglutide and GLP-1 agonist C.
18. The pharmaceutical composition according to any of the previous embodiments, wherein the composition comprises at least one granulate.
19. The pharmaceutical composition according to previous embodiment 18, wherein the at least one granulate comprises the salt of N-(8-(2-hydroxybenzoyl)amino) caprylic acid.
20. The pharmaceutical composition according to any of the previous embodiments 18-19, wherein the at least one granulate further comprises a lubricant, such as magnesium stearate.
21. The pharmaceutical composition according to any of the previous embodiments 18-20, wherein the at least one granulate further comprises the GLP-1 agonist.
22. The pharmaceutical composition according to any of the previous embodiment 18-21, wherein the at least one granulate is prepared by dry granulation, such as by roller compaction.
23. The pharmaceutical composition according to any of the previous embodiment 18-22, wherein the composition comprises an extragranular part.
24. The pharmaceutical composition according to any of the previous embodiment 18-23, wherein the extragranular part of the composition comprises a lubricant or glidant, such as magnesium stearate and/or the GLP-1 agonist.
25. A pharmaceutical composition comprising
    a) 0.5-50 mg of a GLP-1 agonist and
    b) 20-800 mg, such as 25-600, such as 50-500 mg of a salt of N-(8-(2-hydroxybenzoyl)amino)caprylic acid,
    wherein said salt of N-(8-(2-hydroxybenzoyl)amino) caprylic acid constitutes at least 90 w/w %, such as at least 95 w/w % of the excipients of the composition and wherein the GLP-1 agonist is semaglutide.
26. A pharmaceutical composition comprising
    a) 1-25 mg of a GLP-1 agonist and
    b) 50-400 mg of a salt of N-(8-(2-hydroxybenzoyl) amino)caprylic acid,
    wherein said salt of N-(8-(2-hydroxybenzoyl)amino) caprylic acid constitutes at least 90 w/w %, such as at least 95 w/w % of the excipients of the composition and wherein the GLP-1 agonist is semaglutide.
27. A pharmaceutical composition comprising
    a) 1-15 mg of a GLP-1 agonist and
    b) 75-150 mg of a salt of N-(8-(2-hydroxybenzoyl) amino)caprylic acid,
    wherein said salt of N-(8-(2-hydroxybenzoyl)amino) caprylic acid constitutes at least 90 w/w %, such as at least 95 w/w % of the excipients of the composition and wherein the GLP-1 agonist is semaglutide.
28. A pharmaceutical composition comprising
    a) 1-15 mg of a GLP-1 agonist and
    b) 75-125 mg of a salt of N-(8-(2-hydroxybenzoyl) amino)caprylic acid,
    wherein said salt of N-(8-(2-hydroxybenzoyl)amino) caprylic acid constitutes at least 90 w/w %, such as at least 95 w/w % of the excipients of the composition and wherein the GLP-1 agonist is semaglutide.
29. A pharmaceutical composition comprising
    a) 1-15 mg of a GLP-1 agonist and
    b) 80-120 mg of a salt of N-(8-(2-hydroxybenzoyl) amino)caprylic acid, wherein said salt of N-(8-(2-hydroxybenzoyl)amino) caprylic acid constitutes at least 90 w/w %, such as at least 95 w/w % of the excipients of the composition and wherein the GLP-1 agonist is semaglutide.

30. A pharmaceutical composition comprising
    a) 1-15 mg of a GLP-1 agonist and
    b) 200-400 mg of a salt of N-(8-(2-hydroxybenzoyl)amino)caprylic acid,
    wherein said salt of N-(8-(2-hydroxybenzoyl)amino) caprylic acid constitutes at least 90 w/w %, such as at least 95 w/w % of the excipients of the composition and wherein the GLP-1 agonist is semaglutide.

31. A pharmaceutical composition comprising
    a) 1-15 mg of a GLP-1 agonist and
    b) 250-350 mg of a salt of N-(8-(2-hydroxybenzoyl)amino)caprylic acid,
    wherein said salt of N-(8-(2-hydroxybenzoyl)amino) caprylic acid constitutes at least 90 w/w %, such as at least 95 w/w % of the excipients of the composition and wherein the GLP-1 agonist is semaglutide.

32. A pharmaceutical composition comprising
    a) 0.1-25 mg of a GLP-1 agonist and
    b) 20-800 mg, such as 25-600, 50-500 mg of a salt of N-(8-(2-hydroxybenzoyl)amino)caprylic acid,
    wherein said salt of N-(8-(2-hydroxybenzoyl)amino) caprylic acid constitutes at least 90 w/w %, such as at least 95 w/w % of the excipients of the composition and wherein the GLP-1 agonist is GLP-1 agonist C.

33. A pharmaceutical composition comprising
    a) 1-25 mg of a GLP-1 agonist and
    b) 50-400 mg of a salt of N-(8-(2-hydroxybenzoyl)amino)caprylic acid,
    wherein said salt of N-(8-(2-hydroxybenzoyl)amino) caprylic acid constitutes at least 90 w/w %, such as at least 95 w/w % of the excipients of the composition and wherein the GLP-1 agonist is GLP-1 agonist C.

34. A pharmaceutical composition comprising
    a) 1-15 mg of a GLP-1 agonist and
    b) 75-150 mg of a salt of N-(8-(2-hydroxybenzoyl)amino)caprylic acid,
    wherein said salt of N-(8-(2-hydroxybenzoyl)amino) caprylic acid constitutes at least 90 w/w %, such as at least 95 w/w % of the excipients of the composition and wherein the GLP-1 agonist is GLP-1 agonist C.

35. A pharmaceutical composition comprising
    c) 1-15 mg of a GLP-1 agonist and
    d) 75-125 mg of a salt of N-(8-(2-hydroxybenzoyl)amino)caprylic acid,
    wherein said salt of N-(8-(2-hydroxybenzoyl)amino) caprylic acid constitutes at least 90 w/w %, such as at least 95 w/w % of the excipients of the composition and wherein the GLP-1 agonist is GLP-1 agonist C.

36. A pharmaceutical composition comprising
    c) 1-15 mg of a GLP-1 agonist and
    d) 80-120 mg of a salt of N-(8-(2-hydroxybenzoyl)amino)caprylic acid,
    wherein said salt of N-(8-(2-hydroxybenzoyl)amino) caprylic acid constitutes at least 90 w/w %, such as at least 95 w/w % of the excipients of the composition and wherein the GLP-1 agonist is GLP-1 agonist C.

37. A pharmaceutical composition comprising
    a) 1-15 mg of a GLP-1 agonist and
    b) 200-400 mg of a salt of N-(8-(2-hydroxybenzoyl)amino)caprylic acid,
    wherein said salt of N-(8-(2-hydroxybenzoyl)amino) caprylic acid constitutes at least 90 w/w %, such as at least 95 w/w % of the excipients of the composition and wherein the GLP-1 agonist is GLP-1 agonist C.

38. A pharmaceutical composition comprising
    a) 1-15 mg of a GLP-1 agonist and
    b) 250-350 mg of a salt of N-(8-(2-hydroxybenzoyl)amino)caprylic acid,
    wherein said salt of N-(8-(2-hydroxybenzoyl)amino) caprylic acid constitutes at least 95 w/w % of the excipients of the composition and wherein the GLP-1 agonist is GLP-1 agonist C.

39. The pharmaceutical composition according to any of the embodiments 25-38, further comprising 1-10 mg lubricant, such as magnesium stearate.

40. The pharmaceutical composition according to any of the embodiments 25-38, further comprising 1-8 mg, such as 2-5 mg or such as 2-3 mg magnesium stearate per 100 mg salt of N-(8-(2-hydroxybenzoyl)amino) caprylic acid.

41. The pharmaceutical composition according to any of the previous embodiment, wherein the composition is for oral administration.

42. The pharmaceutical composition according to any of the previous embodiments, wherein the composition is a solid composition.

43. The pharmaceutical composition according to the previous embodiments, wherein the composition is a solid composition, such as a tablet, a capsule or a sachet.

44. A pharmaceutical composition comprising
    a) a GLP-1 agonist and
    b) a salt of N-(8-(2-hydroxybenzoyl)amino)caprylic acid,
    wherein the release of the GLP-1 agonist reaches 85% within 15 minutes or 95% within minutes.

45. A pharmaceutical composition comprising
    a) a GLP-1 agonist and
    b) a salt of N-(8-(2-hydroxybenzoyl)amino)caprylic acid,
    wherein the dose corrected exposure at t=30 min is increased relative to a reference composition of type F/H of WO2013/139694.

46. A pharmaceutical composition comprising
    a) a GLP-1 agonist and
    b) a salt of N-(8-(2-hydroxybenzoyl)amino)caprylic acid,
    wherein the dose corrected exposure (AUC) for t=0-30 min is increased relative to a reference composition of type F/H of WO2013/139694.

47. The pharmaceutical composition according to previous embodiment 46, wherein the dose corrected exposure (AUC) for T=0-30 min is increased at least 1.5 fold, such as at least 2 fold.

48. The pharmaceutical composition according to any of the embodiments 25-40 further defined by the features of one or more of the embodiments 8, 10, 11, 18-24 and 41-47.

49. The pharmaceutical composition according to embodiments 44, 45, 46 or 47 further defined by the features of one or more of the embodiments 4, 6-24 and 41-43.

50. A pharmaceutical composition according to any of the previous embodiments for use in medicine.

51. A pharmaceutical composition according to any of the previous embodiments for use in a method of treatment of diabetes and/or obesity.
52. A method of treatment of a subject in need thereof, wherein the method comprises administering a therapeutically active amount of a composition according to any of the previous embodiments to said subject.

Further Embodiments

1. A pharmaceutical composition comprising
   a) a GLP-1 agonist and
   b) a salt of N-(8-(2-hydroxybenzoyl)amino)caprylic acid,
   wherein said salt of N-(8-(2-hydroxybenzoyl)amino) caprylic acid constitutes at least 95 w/w % of the excipients of the composition.
2. The pharmaceutical composition according to embodiment 1, further comprising at least one lubricant.
3. A pharmaceutical composition consisting of:
   a) a GLP-1 agonist,
   b) a salt of N-(8-(2-hydroxybenzoyl)amino)caprylic acid and
   c) at least one lubricant.
4. The pharmaceutical composition according to any of the previous embodiments, wherein said salt of N-(8-(2-hydroxybenzoyl)amino)caprylic acid constitutes above 90 w/w % of the composition.
5. The pharmaceutical composition according to any of the previous embodiments 2-4, wherein the lubricant is magnesium stearate.
6. The pharmaceutical composition according to any of the previous embodiments, wherein a dose unit comprises
   a) 0.5-50 mg of the GLP-1 agonist and/or
   b) 50-500 mg of said salt of N-(8-(2-hydroxybenzoyl) amino)caprylic acid.
7. The pharmaceutical composition according to any of the previous embodiments, wherein a dose unit comprises;
   a) 0.5-50 mg of the GLP-1 agonist,
   b) 50-500 mg of said salt of N-(8-(2-hydroxybenzoyl) amino)caprylic acid and
   c) 1-10 mg lubricant, such as magnesium stearate.
8. The pharmaceutical composition according to any of the previous embodiments wherein the GLP-1 agonist is selected from the group consisting of: liraglutide, semaglutide, GLP-1 agonist B and GLP-1 agonist C.
9. The pharmaceutical composition according to any of the previous embodiments, wherein the composition is a solid composition, such as a tablet for oral administration.
10. A pharmaceutical composition comprising
    a) a GLP-1 agonist and
    b) a salt of N-(8-(2-hydroxybenzoyl)amino)caprylic acid, wherein
       i. the release of the GLP-1 agonist reaches 85% within 15 minutes and/or
       ii. the dose corrected exposure (AUC) from t=0-30 min is increased relative to a reference composition of type F/H of WO2013/139694 and/or
       iii. the dose corrected exposure at 30 min (AUC) is increased relative to a reference composition of type F/H of WO2013/139694.
11. The pharmaceutical composition according to embodiment 10, wherein the composition has one or more of the features of any of the embodiments 1-9.
12. A pharmaceutical composition according to any of the previous embodiments for use in medicine.
13. A pharmaceutical composition according to any of the previous embodiments for use in a method of treatment of diabetes and/or obesity.
14. A method of treatment of an individual in need thereof, comprising administering a therapeutically active amount of a composition according to any of the previous embodiments to said individual.

METHODS AND EXAMPLES

General Methods of Detection and Characterisation
Assay I: Dissolution Test

A dissolution test is performed in an appropriate dissolution apparatus e.g. USP dissolution apparatus 2, and a standard dissolution test according to the European Pharmacopeia (Ph Eur 2.9.3) may be performed to measure the release of the GLP-1 agonist and SNAC in vitro.

Data described herein is obtained using apparatus 2 in accordance with United States Pharmacopoeia 35 using a paddle rotation speed of 50 rpm. For testing at pH 6.8, the 500 mL dissolution medium of 0.05 M phosphate buffer is used at a temperature of 37±0.5° C. Dissolution media has a content of 0.1% Brij®35. Samples are removed at appropriate intervals. Sample content is determined using a RP-HPLC method for dual detection of SNAC and GLP-1 agonist. The sample content is calculated based on the peak area of the SNAC and GLP-1 agonist peaks in the chromatogram relative to the peak areas of the SNAC and GLP-1 agonist references, respectively. The released amount of SNAC and GLP-1 agonist is calculated as percentages of the actual content in the tablets i.e. 100/200/300 mg/tablet SNAC and 3/5/4 mg/tablet GLP-1 agonist (e.g. analogue A, B or C). The actual content in the tablets is determined using Assay (II). The released amount of GLP-1 agonist is reported as average of 3 tablets.

Assay II: Analysis of Amount of GLP-1 Agonist and SNAC

Tablets are weighed before extraction of the GLP-1 agonist and SNAC. Tablets are dissolved in a relevant amount of 0.05 M phosphate buffer, pH 7.4, with 20% acetonitrile. Extraction time of two hours is used. Samples are centrifuged and a suitable volume is transferred to HPLC vial. Standards of relevant GLP-1 agonist and SNAC are prepared by using the same diluent as for the samples. HPLC with an UV-detector is used for determining the GLP-1 agonist and SNAC content. The sample content is calculated based on the peak area of the SNAC and GLP-1 agonist peaks in the chromatogram relative to the peak areas of the SNAC and GLP-1 agonist references, respectively.

The content is reported as average of 3 tablets.

Assay III: Pharmacokinetic Studies in Beagle Dogs

Pharmacokinetic (PK) studies in Beagle dogs are conducted to determine the exposure of the GLP-1 agonists after peroral administration of different dosage forms.

For the pharmacokinetic studies male Beagle dogs are used, 1 to 5 years of age and weighing approximately 10-12 kg at the start of the studies. The dogs are group housed in pens (12 hours light: 12 hours dark), and fed individually and restrictedly once daily with Royal Canin Medium Adult dog (Royal Canin Products, China Branch, or Brogaarden A/S, Denmark). Exercise and group social are permitted daily, whenever possible. The dogs are used for repeated pharmacokinetic studies with a suitable wash-out period between successive dosings. An appropriate acclimatization period is given prior to initiation of the first pharmacokinetic study. All handling, dosing and blood sampling of the animals are performed by trained and skilled staff. Before the studies the dogs are fasted overnight and from 0 to 4 h after dosing. Besides, the dogs are restricted to water 1 hour before dosing until 4 hours after dosing, but otherwise have ad libitum access to water during the whole period.

The GLP-1 agonist tablets used for the p.o. studies described herein are immediate release SNAC-based tablets dosed orally.

The tablets containing the GLP-1 agonist are administered in the following manner: 10 min prior to tablet administration the dogs are dosed subcutaneously with approximately 3 nmol/kg of SEQ ID NO: 3). The GLP-1 tablets are placed in the back of the mouth of the dog to prevent chewing. The mouth is then closed and 10 mL or 50 mL of tap water is given by a syringe or gavage to facilitate swallowing of the tablet.

Blood Sampling

Blood is sampled at predefined time points for up till 10 hr post dosing to adequately cover the full plasma concentration-time absorption profile of the GLP-1 agonist. For each blood sampling time point approximately 0.8 mL of whole blood is collected in a 1.5 mL EDTA coated tube, and the tube is gently turned to allowing mixing of the sample with the EDTA. Blood samples (for example 0.8 mL) are collected in EDTA buffer (8 mM) and then centrifuged at 4° C. and 2000G for 10 minutes. Plasma is pipetted into Micronic tubes on dry ice, and kept at −20° C. until analysis.

Blood samples are taken as appropriate, for example from a venflon in the cephalic vein in the front leg for the first 2 hours and then with syringe from the jugular vein for the rest of the time points (the first few drops are allowed to drain from the venflon to avoid heparin saline from the venflon in the sample).

General Methods for Tablet Preparation

Method 1: Dry Granulation

Dry granulation is carried out by roller compaction on a Gerteis MICRO-PACTOR. The roller speed is set at 1 rpm and roller compaction force at 6 kN/cm, fill depth is 8 mm. Subsequent to dry granulation hand sieving of ribbons into granules by using a 0.8 mm wire mesh screen is carried out. Optionally second sieving step on Retch oscillating sieve is applied in order to remove fines, a 90 µm screen is used.

Method 2: Tablet Preparation

Tablets are produced on a Kilian Style One or a Fette 102I mounted with a single or 4 sets of punches, resulting in 4 mm round, 7 mm round or 5.75×10 mm, 7.2×12 mm, 7.5×12.5 mm or 9×18 mm oval tablets having no score. Punch size is chosen according to the total tablet weight. For the Kilian Style One, the press speed is set to 10% and for Fette 102I the press speed is set at 20 rpm. The fill volume is adjusted to obtain tablets having target weights from 28.6 mg to 823.5 mg. Compression forces around 2 to 15 kN are applied to obtain tablets with a crushing strength of around 20-160 N respective to the tablet size.

EXAMPLES

Example 1—Preparation of Compositions

Tablets with different amounts of GLP-1 agonist, SNAC and further excipients were prepared. The content of the prepared compositions is provided in Table 1 (Table 1.1, Table 1.2 and Table 1.3). GLP-1 agonist A is semaglutide, GLP-1 agonist B is Diacylated [Aib8,Arg34,Lys37]GLP-1(7-37) (Example 2 of WO2011/080103) and GLP-1 agonist C is Diacylated[Aib8,Glu22,Arg26,Lys27,Glu30,Arg34, Lys36]-GLP-1-(7-37)-peptidyl-Glu-Gly (Example 31 of WO2012/140117). Semaglutide can be prepared according to the method described in WO2006/097537, Example 4. GLP-1 agonists B and C can be prepared as described in WO2011/080103 and WO2012/140117, respectively. SNAC was prepared according to the method described in WO2008/028859.

Reference compositions A, B and C were generally prepared as described in WO2013/139694. The test compositions (A1, A2, B1-134, C1 and C2 were generally prepared as described in method 1 and 2 above, with minor variations in the process prior to roller compaction and tablet preparation as specified below.

Table 1. Tablet Compositions Expressed as Mg Per Tablet

TABLE 1.1

| Overview of compositions with GLP-1 agonist A | | | |
|---|---|---|---|
| Composition | Reference A | A1 | A2 |
| GLP-1 agonist A (mg) | 3 | 3 | 3 |
| SNAC (mg) | 300 | 100 | 300 |
| Magnesium stearate (mg) | 9.7 | 2.6 | 7.7 |
| Povidone (mg) | 8 | — | — |
| MCC (mg) | 80 | — | — |

TABLE 1.2

| Overview of compositions with GLP-1 agonist B | | | | | |
|---|---|---|---|---|---|
| Composition | Reference B | B1 | B2 | B3 | B4 |
| GLP-1 agonist B (mg) | 5 | 5 | 5 | 5 | 5 |
| SNAC (mg) | 300 | 100 | 200 | 300 | 300 |
| Magnesium stearate (mg) | 9.7 | 2.6 | 5.1 | 7.7 | — |
| Glyceryl dibehenate (mg) | — | — | — | — | 2.2 |
| Povidone (mg) | 8 | — | — | — | — |
| MCC (mg) | 80 | — | — | — | — |

TABLE 1.3

| Overview of compositions with GLP-1 agonist C | | | |
|---|---|---|---|
| Ingredients Composition | Reference C | C1 | C2 |
| GLP-1 agonist C (mg) | 4 | 4 | 4 |
| SNAC (mg) | 300 | 100 | 300 |
| Magnesium stearate (mg) | 9.7 | 2.6 | 7.7 |
| Povidone (mg) | 8 | — | — |
| MCC (mg) | 80 | — | — |

To prepare test compositions A1, A2, B1, B3, C1 and C2 the following procedure was followed; magnesium stearate for the granules was passed through a 355 µm or finer sieve. The correct amount of magnesium stearate and SNAC were weighed. Magnesium stearate was manually mixed with SNAC according to the geometric mixing principle. Two cycles of geometric dilution were applied. The remaining quantity of SNAC was transferred to a blending container and mixed with the SNAC and magnesium stearate pre-mix for 30 min at 25 rpm in a Turbula mixer. The blend was roller compacted as described in Method 1.

The correct amount of GLP-1 agonist and SNAC and magnesium stearate granules were weighed. Granules of SNAC and magnesium stearate were added to the blending container and manually mixed with GLP-1 agonist according to the geometric mixing principle. Two cycles of geometric dilution were applied. The remaining quantity of SNAC and magnesium stearate granules was transferred to the blending container. The final mixing of GLP-1 agonist and granules was done for 7 min at 25 rpm or for 20 min at 25 rpm in a Turbula mixer. Tablets were prepared from this composition according to Method 2.

B2 was prepared as follows; the magnesium stearate and SNAC granules were prepared as described for previous test compositions. The correct amount of SNAC and magnesium stearate granules and GLP-1 agonist were weighed. The ⅓ of the granules of SNAC and magnesium stearate were mixed with GLP-1 agonist by addition of the granules to a blending container according to the geometric mixing principle. Mixing for 7 min at 25 rpm in a Turbula mixer was applied. Two cycles of geometric dilution were applied. The remaining quantity of SNAC and magnesium stearate granules was transferred to the blending container and mixed according to geometric mixing principle. The final mixing of GLP-1 agonist and granules was done for 7 min at 25 rpm in a Turbula mixer. Tablets were prepared from this composition according to Method 2.

B4 was prepared as follows; SNAC granules (without magnesium stearate) were prepared as described for previous test compositions and in Method 1. The correct amount of GLP-1 agonist, and SNAC granules were weighed. SNAC granules were added to a blending container and mixed with GLP-1 agonist according to the geometric mixing principle. Two cycles of geometric dilution were applied. The remaining quantity of SNAC granules was added to the blending container. Mechanical mixing of GLP-1 agonist and granules was done for 7 min at 25 rpm in a Turbula mixer. Glyceryl dibehenate (Compritol 888 ATO) was passed through a 350 µm or below sieve. The correct amount of Glyceryl dibehenate was weighed. Glyceryl dibehenate was manually mixed with the mixture of SNAC granules and GLP-1 agonist according to the geometric mixing principle. Three cycles of geometric dilution were applied. The obtained mixture was transferred to a blending container with remaining SNAC granules and GLP-1 agonist mixture. The final mixing with Compritol 888 ATO was done for 2 min at 25 rpm in a Turbula mixer. Tablets were prepared from this composition according to Method 2.

Example 2—Dissolution Testing

The objective of the present study was to evaluate the dissolution of the series of the tablet compositions described in Example 1.

Dissolution was measured according to Assay I. Table 2 shows the results for tablets prepared according to Example 1 above, wherein the release is presented as "GLP-1 agonist in solution (%)" describing the amount of GLP-1 agonist in solution after 15, 30 and 60 min relative to the total amount of GLP-1 agonist in the tablet at the start of the experiment. The total amount of GLP-1 agonist and SNAC in the tablets was determined according to Assay

TABLE 2

| Composition/ | GLP-1 agonist in solution (%) | | |
|---|---|---|---|
| Dosage form | 15 min | 30 min | 60 min |
| A1 | 91.3 | 90.5 | 90.5 |
| A2 | 89.0 | 96.8 | 95.8 |
| B1 | 96.9 | 97.1 | 96.7 |
| B2 | 89.3 | 89.7 | 90.0 |
| B3 | full release | full release | full release |

TABLE 2-continued

| Composition/ | GLP-1 agonist in solution (%) | | |
|---|---|---|---|
| Dosage form | 15 min | 30 min | 60 min |
| B4 | 92.4 | 95.3 | 94.3 |
| C1 | 98.2 | 97.6 | 97.5 |
| C2 | 97.7 | full release | full release |
| Reference A | 35.5 | 58.1 | 75.6 |
| Reference B | 44.0 | 69.2 | 83.5 |
| Reference C | 44.9 | 71.4 | 93.1 |

The results obtained show that the test compositions display a faster release of the GLP-1 agonist compared to what was observed for the reference compositions. A significantly faster release of the GLP-1 agonist is observed for the early time points, i.e. at 15 and 30 minutes. The difference in release is less significant after 60 minutes. The amount of SNAC in the tablets did not influence the release of the GLP-1 agonist i.e. that tablets comprising 100 mg SNAC dissolve as fast as tablets comprising 300 mg SNAC when measured after 15 minutes or later.

Further data obtained after 5, 10, 15, 20, 30, 45 and 60 minutes for composition A1 and Reference A, is shown in FIG. 1, demonstrating increased release at every time point.

Example 3—Oral Exposure

The objective of the present study was to evaluate the oral exposure in beagle dogs of the series of compositions described in Example 1 above using 10 ml water for dosing to the dogs. The number of tests performed for each formulation is indicated by n.

Analysis and Results

The plasma concentration of the respective GLP-1 agonist was analysed using ELISA or a similar antibody based assay such as LOCI. Individual plasma concentration-time profiles were analysed by a non-compartmental model in WinNonlin v. 5.0 or Phoenix v. 6.2 or 6.3 (Pharsight Inc., Mountain View, CA, USA), or other relevant software for PK analysis.

The compound exposure measured at t=30 min was determined and normalized by dose/kg bodyweight.

The area under the plasma concentration versus time curve for the first 30 min (AUC, [time×concentration]) was calculated (by the Pharsight programme) after oral administration and normalized by ((dose/kg bodyweight)*100) to obtain the dose corrected exposure. The average values obtained are provided in table 3.1.

Figure 2:
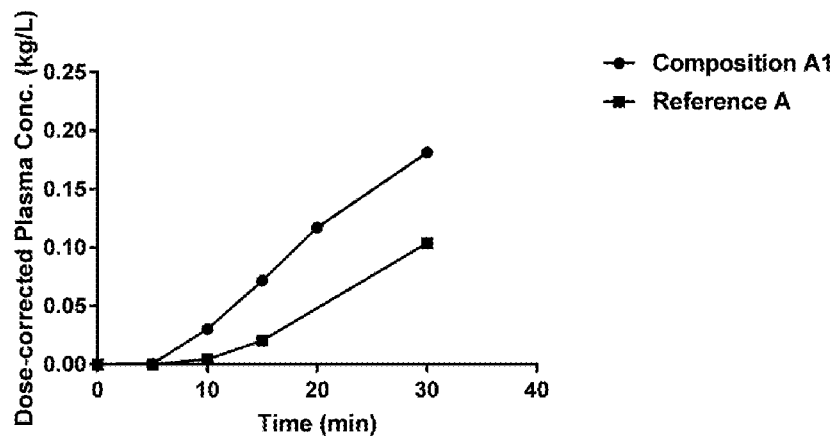
FIG. 2 shows increased dose-corrected exposure following oral tablet dosing to beagle dogs of analogues A, B and C when formulated according to the invention. Data are given as mean. Compositions A1, B1 and C1 all demonstrate an increased dose-corrected exposure relative to the reference compositions.
Figure 2:
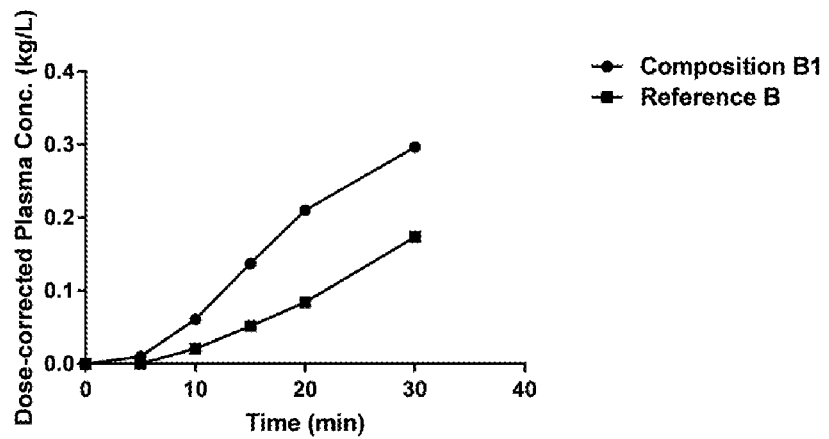
Figure 2:
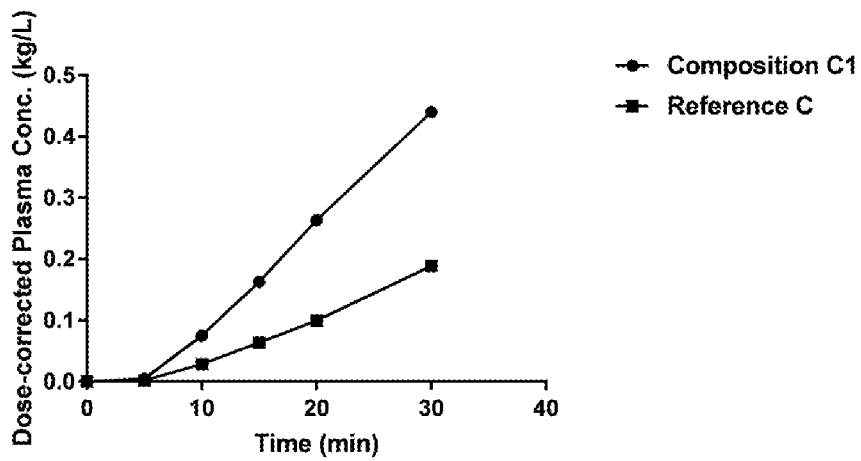

The mean dose-corrected exposure of analogues A, B and C for t=0, 5, 10, 15, 20 and 30 min, obtained with the formulations A1, Reference A, B1 and Reference B, C1 and Reference C are shown in FIG. 2.

Since individual GLP-1 agonists behave differently, i.e. may have a higher or lower general bioavailability, it may be relevant also to compare the relative exposure, to understand the effect of a specific dosage form/dose unit compared to the effect of a different dosage form/dose unit comprising the same GLP-1 agonist. Such results are included in table 3.2, showing that a 2 fold increase in exposure during the first 30 minutes was obtained using the dosage form disclosed herein compared to the reference dosage form for each GLP-1 agonist.

TABLE 3.1

Dose corrected exposure - average values

| GLP-1 agonist | Formulation/ dosage form | SNAC amount | Dose corrected AUC 0-30 min (arbitrary unit) | Dose corrected exposure t = 30 min (kg/L) |
|---|---|---|---|---|
| A (n = 24) | Reference A | 300 | 1.68 | 0.104 |
| A (n = 16) | A1 | 100 | 3.84 | 0.181 |
| A (n = 16) | A2 | 300 | 2.63 | 0.153 |
| B (n = 24) | Reference B | 300 | 3.16 | 0.173 |
| B (n = 16) | B1 | 100 | 6.86 | 0.297 |
| B (n = 16) | B3 | 300 | 6.80 | 0.390 |
| B (n = 16) | B4 | 300 | 6.71 | 0.385 |
| C (n = 12) | Reference C | 300 | 3.63 | 0.189 |
| C (n = 12) | C1 | 100 | 9.02 | 0.442 |

TABLE 3.2

Dose corrected exposure - relative exposure

| GLP-1 agonist | Formulation | SNAC amount | Fold change of Dose corrected AUC 0-30 min normalized to reference | Fold change of Dose corrected exposure t = 30 min normalized to reference |
|---|---|---|---|---|
| A (n = 24) | Reference A | 300 | 1.00 | 1.00 |
| A (n = 16) | A1 | 100 | 2.29 | 1.74 |
| A (n = 16) | A2 | 300 | 1.57 | 1.47 |
| B (n = 24) | Reference B | 300 | 1.00 | 1.00 |
| B (n = 16) | B1 | 100 | 2.17 | 1.72 |
| B (n = 16) | B3 | 300 | 2.15 | 2.25 |
| B (n = 16) | B4 | 300 | 2.12 | 2.22 |
| C (n = 12) | Reference C | 300 | 1.00 | 1.00 |
| C (n = 12) | C1 | 100 | 2.49 | 2.33 |

Example 4—Oral Exposure for 25-800 mg SNAC Tablets

Further tablets, with decreasing and increasing amounts of SNAC, were manufactured as described above for A1 and A2.

A5 has the same composition as A2 above. The granules were here manufactured by dry granulation using a MINI-PACTOR® followed by removal of fines using a 90 µm sieve screen. SNAC and magnesium stearate were mixed for 50 min at 25 rpm in a V-shell prior to dry granulation. The SNAC and magnesium stearate granules were mixed with GLP-1 agonist for 10 min at 25 rpm in a V-shell prior to compression of tablets according to Method 2. For composition A7, the GLP-1 agonist A was dry granulated together with SNAC and magnesium stearate using a MINI-PACTOR® followed by removal of fines using a 90 µm sieve screen. SNAC and magnesium stearate were mixed for 50 min at 25 rpm in a V-shell and then GLP-1 was added and mixed for 20 min at 25 rpm prior to dry granulation. The granules were subsequently compressed into tablets according to Method 2. For both compositions A5 and A7, the MINI-PACTOR was operated at a compaction force of 6 kN/cm, a gap of 1 mm, a roll speed of 3 rpm and with a 0.63 µm wire mesh screen.

TABLE 4.1

Tablet compositions expressed as mg per tablet

| Composition | Reference A | A3 | A4 | A5 | A6 | A7 |
|---|---|---|---|---|---|---|
| GLP-1 agonist A (mg) | 3 | 3 | 3 | 3 | 3 | 3 |
| SNAC (mg) | 300 | 25 | 100 | 300 | 800 | 300 |
| Magnesium stearate (mg) | 9.7 | 0.6 | 2.6 | 7.7 | 20.5 | 7.7 |
| Povidone (mg) | 8 | — | — | — | — | — |
| MCC (mg) | 80 | — | — | — | — | — |

The objective of the present study was to evaluate the oral exposure in beagle dogs of the series of compositions described in Table 4. The oral exposure was evaluated in beagle dogs as described in Example 1 above using 50 ml water for dosing to the dogs. The number of tests performed for each formulation is indicated by n.

Results was analysed as described in example 3 and the average values obtained are provided in table 4.2 and the relative values are provided in table 4.3 below.

TABLE 4.2

Dose corrected exposure - average values

| GLP-1 agonist | Formulation/ dosage form | SNAC amount | Dose corrected AUC 0-30 min (arbitrary units) | Dose corrected exposure t = 30 min (kg/L) |
|---|---|---|---|---|
| A (n = 19) | Reference A | 300 | 0.82 | 0.048 |
| A (n = 16) | A3 | 25 | 4.30 | 0.168 |
| A (n = 34) | A4 | 100 | 3.30 | 0.151 |
| A (n = 16) | A5 | 300 | 3.27 | 0.173 |
| A (n = 16) | A6 | 800 | 2.48 | 0.147 |
| A (n = 16) | A7 | 300 | 2.60 | 0.141 |

TABLE 4.3

Dose corrected exposure - relative exposure

| GLP-1 agonist | Formulation/ dosage form | SNAC amount | Fold change of Dose corrected AUC 0-30 min normalized to reference | Fold change of Dose corrected exposure t = 30 min normalized to reference |
|---|---|---|---|---|
| A (n = 19) | Reference A | 300 | 1.00 | 1.00 |
| A (n = 16) | A3 | 25 | 5.24 | 3.50 |
| A (n = 34) | A4 | 100 | 4.02 | 3.15 |
| A (n = 16) | A5 | 300 | 3.99 | 3.60 |
| A (n = 16) | A6 | 800 | 3.02 | 3.06 |
| A (n = 16) | A7 | 300 | 3.17 | 2.94 |

The data confirmed that an increase in exposure during the first 30 minutes was obtained using the dosage form disclosed herein compared to the reference dosage form.

The invention claimed is:

1. A pharmaceutical composition comprising semaglutide, sodium N-(8-(2-hydroxybenzoyl)amino)caprylic acid (SNAC), and magnesium stearate, P1 wherein the semaglutide is in an amount of 0.2 to 100 mg,
   wherein the pharmaceutical composition comprises 2-5 mg of the magnesium stearate per 100 mg of the SNAC; and
   wherein the SNAC constitutes at least 95% (w/w) of the excipients of the composition.

2. The pharmaceutical composition according to claim 1, wherein the pharmaceutical composition comprises 1.5 mg of the semaglutide.

3. The pharmaceutical composition according to claim 1, wherein the pharmaceutical composition comprises 4 mg of the semaglutide.

4. The pharmaceutical composition according to claim 1, wherein the pharmaceutical composition comprises 2 to 20 mg of the semaglutide.

5. The pharmaceutical composition according to claim 1, wherein the pharmaceutical composition comprises 25 mg of the semaglutide.

6. The pharmaceutical composition according to claim 1, wherein the pharmaceutical composition comprises 50 mg of the semaglutide.

7. The pharmaceutical composition according to claim 1, wherein the pharmaceutical composition comprises 100 mg of the SNAC.

8. The pharmaceutical composition according to claim 1, wherein the pharmaceutical composition comprises 300 mg of the SNAC.

9. The pharmaceutical composition according to claim 1, wherein the pharmaceutical composition comprises 1.5 mg of the semaglutide and 100 mg of the SNAC.

10. The pharmaceutical composition according to claim 1, wherein the pharmaceutical composition comprises 1.5 mg of the semaglutide and 2-3 mg of the magnesium stearate.

11. The pharmaceutical composition according to claim 1, wherein the pharmaceutical composition comprises 1.5 mg of the semaglutide, 100 mg of the SNAC, and 2-3 mg of the magnesium stearate.

12. The pharmaceutical composition according to claim 1, wherein the pharmaceutical composition comprises 1.5 mg of the semaglutide, 100 mg of the SNAC, and 2.6 mg of the magnesium stearate.

13. The pharmaceutical composition according to claim 1, wherein the pharmaceutical composition comprises 4 mg of the semaglutide and 100 mg of the SNAC.

14. The pharmaceutical composition according to claim 1, wherein the pharmaceutical composition comprises 4 mg of the semaglutide and 2-3 mg of the magnesium stearate.

15. The pharmaceutical composition according to claim 1, wherein the pharmaceutical composition comprises 4 mg of the semaglutide, 100 mg of the SNAC, and 2-3 mg of the magnesium stearate.

16. The pharmaceutical composition according to claim 1, wherein the pharmaceutical composition comprises 4 mg of the semaglutide, 100 mg of the SNAC, and 2.6 mg of the magnesium stearate.

17. The pharmaceutical composition according to claim 1, wherein the pharmaceutical composition comprises 2 to 20 mg of the semaglutide and 100 mg of the SNAC.

18. The pharmaceutical composition according to claim 1, wherein the pharmaceutical composition comprises 2 to 20 mg of the semaglutide and 2-3 mg of the magnesium stearate.

19. The pharmaceutical composition according to claim 1, wherein the pharmaceutical composition comprises 2 to 20 mg of the semaglutide, 100 mg of the SNAC, and 2-3 mg of the magnesium stearate.

20. The pharmaceutical composition according to claim 1, wherein the pharmaceutical composition comprises 2 to 20 mg of the semaglutide, 100 mg of the SNAC, and 2.6 mg of the magnesium stearate.

21. The pharmaceutical composition according to claim 1, wherein the pharmaceutical composition comprises 25 mg of the semaglutide and 300 mg of the SNAC.

22. The pharmaceutical composition according to claim 1, wherein the pharmaceutical composition comprises 25 mg of the semaglutide 100 to 300 mg of SNAC, and 2-8 mg of the magnesium stearate.

23. The pharmaceutical composition according to claim 1, wherein the pharmaceutical composition comprises 25 mg of the semaglutide, 300 mg of the SNAC, and 7.7 mg of the magnesium stearate.

24. The pharmaceutical composition according to claim 1, wherein the pharmaceutical composition comprises 50 mg of the semaglutide and 300 mg of the SNAC.

25. The pharmaceutical composition according to claim 1, wherein the pharmaceutical composition comprises 50 mg of the semaglutide 100 to 300 mg of SNAC, and 2-8 mg of the magnesium stearate.

26. The pharmaceutical composition according to claim 1, wherein the pharmaceutical composition comprises 50 mg of the semaglutide, 300 mg of the SNAC, and 7.7 mg of the magnesium stearate.

27. A method of treating type 2 diabetes, comprising administering to a subject in need thereof the pharmaceutical composition according to claim 1.

28. The method according to claim 27, wherein the composition comprises 1.5 mg of the semaglutide.

29. The method according to claim 27, wherein the composition comprises 4 mg of the semaglutide.

30. The method according to claim 27, wherein the composition comprises 2-20 mg of the semaglutide.

31. The method according to claim 27, wherein the composition comprises 25 mg of the semaglutide.

32. The method according to claim 27, wherein the composition comprises 50 mg of the semaglutide.

33. The method according to claim 27, wherein the composition comprises 100 mg of the SNAC.

34. The method according to claim 27, wherein the composition comprises 300 mg of the SNAC.

35. The method according to claim 27, wherein the composition comprises 2.6 mg of the magnesium stearate.

36. The method according to claim 27, wherein the composition comprises 7.7 mg of the magnesium stearate.

37. The method according to claim 27, wherein the composition comprises 1.5 mg of the semaglutide, 100 mg of the SNAC, and 2.6 mg of the magnesium stearate.

38. The method according to claim 27, wherein the composition comprises 4 mg of the semaglutide, 100 mg of the SNAC, and 2.6 mg of the magnesium stearate.

39. The method according to claim 27, wherein the composition comprises 2-20 mg of the semaglutide, 100 mg of the SNAC, and 2.6 mg of the magnesium stearate.

40. The method according to claim 27, wherein the composition comprises 25 mg of the semaglutide, 300 mg of the SNAC, and 7.7 mg of the magnesium stearate.

41. The method according to claim 27, wherein the composition comprises 50 mg of the semaglutide, 300 mg of the SNAC, and 7.7 mg of the magnesium stearate.

42. A method of reducing body weight, comprising administering to a subject in need thereof the pharmaceutical composition according to claim 1.

43. The method according to claim 42, wherein the composition comprises 1.5 mg of the semaglutide.

44. The method according to claim 42, wherein the composition comprises 4 mg of the semaglutide.

45. The method according to claim 42, wherein the composition comprises 2-20 mg of the semaglutide.

46. The method according to claim 42, wherein the composition comprises 25 mg of the semaglutide.

47. The method according to claim 42, wherein the composition comprises 50 mg of the semaglutide.

48. The method according to claim 42, wherein the composition comprises 100 mg of the SNAC.

49. The method according to claim 42, wherein the composition comprises 300 mg of the SNAC.

50. The method according to claim 42, wherein the composition comprises 2.6 mg of the magnesium stearate.

51. The method according to claim 42, wherein the composition comprises 7.7 mg of the magnesium stearate.

52. The method according to claim 42, wherein the composition comprises 1.5 mg of the semaglutide, 100 mg of the SNAC, and 2.6 mg of the magnesium stearate.

53. The method according to claim 42, wherein the composition comprises 4 mg of the semaglutide, 100 mg of the SNAC, and 2.6 mg of the magnesium stearate.

54. The method according to claim 42, wherein the composition comprises 2-20 mg of the semaglutide, 100 mg of the SNAC, and 2.6 mg of the magnesium stearate.

55. The method according to claim 42, wherein the composition comprises 25 mg of the semaglutide, 300 mg of the SNAC, and 7.7 mg of the magnesium stearate.

56. The method according to claim 42, wherein the composition comprises 50 mg of the semaglutide, 300 mg of the SNAC, and 7.7 mg of the magnesium stearate.

* * * * *

UNITED STATES PATENT AND TRADEMARK OFFICE
CERTIFICATE OF CORRECTION

PATENT NO. : 12,396,953 B2  
APPLICATION NO. : 18/386839  
DATED : August 26, 2025  
INVENTOR(S) : Betty Lomstein Pedersen et al.

Page 1 of 1

It is certified that error appears in the above-identified patent and that said Letters Patent is hereby corrected as shown below:

In the Claims

At Column 39, Claim number 1, Line number 3, please replace as follows:
sodium N-(8-(2-hydroxybenzoyl)amino)caprylate At Column 39, Claim number 1, Line numbers 4-5, please replace as follows:
(SNAC), and magnesium stearate, wherein the semaglutide is in an amount of 0.2 to 100 mg, At Column 40, Claim number 22, Line 14, please replace as follows:
of the semaglutide, 100 to 300 mg of SNAC, and 2-8 mg of Signed and Sealed this  
Fourteenth Day of October, 2025

John A. Squires  
*Director of the United States Patent and Trademark Office*

SEQUENCE LISTING

Sequence total quantity: 6
SEQ ID NO: 1    moltype = AA  length = 31
FEATURE         Location/Qualifiers

```
                        -continued source                  1..31
                        mol_type = protein
                        organism = Homo sapiens
SEQUENCE: 1
HAEGTFTSDV SSYLEGQAAK EFIAWLVKGR G                              31

SEQ ID NO: 2            moltype = AA  length = 40
FEATURE                 Location/Qualifiers
source                  1..40
                        mol_type = protein
                        organism = Heloderma suspectum
SEQUENCE: 2
HGEGTFITSD LSKQMEEEAV RLFIEWLKNG GPSSGAPPPS                     40

SEQ ID NO: 3            moltype = AA  length = 29
FEATURE                 Location/Qualifiers
source                  1..29
                        mol_type = protein
                        organism = Homo sapiens
SEQUENCE: 3
HSQGTFTSDY SKYLDSRRAQ DFVQWLMNT                                 29

SEQ ID NO: 4            moltype = AA  length = 31
FEATURE                 Location/Qualifiers
REGION                  1..31
                        note = Synthetic
MOD_RES                 2
                        note = Aib
MOD_RES                 20
                        note = The amino acid residue is modified with a
                         substituent.
source                  1..31
                        mol_type = protein
                        organism = synthetic construct
SEQUENCE: 4
HXEGTFTSDV SSYLEGQAAK EFIAWLVRGR G                              31

SEQ ID NO: 5            moltype = AA  length = 31
FEATURE                 Location/Qualifiers
REGION                  1..31
                        note = Synthetic
MOD_RES                 2
                        note = Aib
MOD_RES                 20
                        note = The amino acid residue is modified with a
                         substituent.
MOD_RES                 31
                        note = The amino acid residue is modified with a
                         substituent.
source                  1..31
                        mol_type = protein
                        organism = synthetic construct
SEQUENCE: 5
HXEGTFTSDV SSYLEGQAAK EFIAWLVRGR K                              31

SEQ ID NO: 6            moltype = AA  length = 33
FEATURE                 Location/Qualifiers
REGION                  1..33
                        note = Synthetic
MOD_RES                 2
                        note = Aib
MOD_RES                 21
                        note = The amino acid residue is modified with a substituent
MOD_RES                 30
                        note = The amino acid residue is modified with a substituent
source                  1..33
                        mol_type = protein
                        organism = synthetic construct
SEQUENCE: 6
HXEGTFTSDV SSYLEEQAAR KFIEWLVRGK GEG                            33
```